(12) United States Patent
Skands et al.

(10) Patent No.: US 12,403,182 B2
(45) Date of Patent: Sep. 2, 2025

(54) LIQUID PHARMACEUTICAL FORMULATIONS OF PTH CONJUGATES

(71) Applicant: Ascendis Pharma Bone Diseases A/S, Hellerup (DK)

(72) Inventors: Anja R. H. Skands, Hellerup (DK); Felix Cleemann, Heidelberg (DE); Michael Duelund Sørensen, Hellerup (DK); Julia Baron, Heidelberg (DE); Eric Hoffmann, Heidelberg (DE); Kennett Sprogøe, Hellerup (DK)

(73) Assignee: ASCENDIS PHARMA BONE DISEASES A/S, Hellerup (DK)

(*) Notice: Subject to any disclaimer, the term of this patent is extended or adjusted under 35 U.S.C. 154(b) by 1006 days.

(21) Appl. No.: 17/428,608

(22) PCT Filed: Feb. 10, 2020

(86) PCT No.: PCT/EP2020/053316
§ 371 (c)(1),
(2) Date: Aug. 4, 2021

(87) PCT Pub. No.: WO2020/165087
PCT Pub. Date: Aug. 20, 2020

(65) Prior Publication Data
US 2022/0088149 A1   Mar. 24, 2022

(30) Foreign Application Priority Data

Feb. 11, 2019  (EP) .................................... 19156485
Apr. 12, 2019  (EP) .................................... 19168857

(51) Int. Cl.
| | | |
|---|---|---|
| A61K 38/29 | (2006.01) | |
| A61K 47/10 | (2017.01) | |
| A61K 47/12 | (2006.01) | |
| A61K 47/18 | (2017.01) | |
| A61K 47/26 | (2006.01) | |
| A61K 47/54 | (2017.01) | |
| A61K 47/60 | (2017.01) | |

(52) U.S. Cl.
CPC ............ *A61K 38/29* (2013.01); *A61K 47/10* (2013.01); *A61K 47/12* (2013.01); *A61K 47/183* (2013.01); *A61K 47/26* (2013.01); *A61K 47/545* (2017.08); *A61K 47/60* (2017.08)

(58) Field of Classification Search
None
See application file for complete search history.

(56) References Cited

U.S. PATENT DOCUMENTS

| | | |
|---|---|---|
| 5,567,439 A | 10/1996 | Myers et al. |
| 5,744,444 A | 4/1998 | Forssmann et al. |
| 7,585,837 B2 | 9/2009 | Schechter et al. |
| 7,820,179 B2 | 10/2010 | Brown-Augsburger et al. |
| 8,101,729 B2 | 1/2012 | Niemczyk et al. |
| 8,618,124 B2 | 12/2013 | Greenwald et al. |
| 8,754,190 B2 | 6/2014 | Ashley et al. |
| 8,865,220 B2 | 10/2014 | Ho et al. |
| 8,906,847 B2 | 12/2014 | Cleemann et al. |
| 8,946,405 B2 | 2/2015 | Ashley et al. |
| 10,980,860 B2 | 4/2021 | Vetter et al. |
| 11,590,207 B2 | 2/2023 | Holten-Andersen et al. |
| 11,759,504 B2 | 9/2023 | Sprogøe et al. |
| 11,793,861 B2 | 10/2023 | Sprogøe et al. |
| 11,857,603 B2 | 1/2024 | Sprogøe et al. |
| 11,890,326 B2 | 2/2024 | Inventor et al. |
| 11,918,628 B2 | 3/2024 | Sprogøe et al. |
| 2003/0166581 A1 | 9/2003 | Almarsson et al. |
| 2005/0124537 A1 | 6/2005 | Kostenuik et al. |
| 2005/0148763 A1 | 7/2005 | Sekimori et al. |
| 2006/0045912 A1 | 3/2006 | Truog |
| 2006/0069021 A1 | 3/2006 | Costantino et al. |
| 2008/0176787 A1* | 7/2008 | Morley .................. A61K 38/29 514/18.3 |
| 2009/0305965 A1* | 12/2009 | Kang ................... A61K 9/0019 514/1.1 |
| 2010/0129341 A1 | 5/2010 | Sakon et al. |
| 2011/0112021 A1 | 5/2011 | Rau et al. |
| 2011/0195900 A1 | 8/2011 | Schteingart et al. |
| 2011/0229580 A1 | 9/2011 | Srivastava et al. |
| 2011/0305766 A1 | 12/2011 | Ho et al. |
| 2012/0035101 A1 | 2/2012 | Fares et al. |
| 2012/0040320 A1 | 2/2012 | Nadeau |

(Continued)

FOREIGN PATENT DOCUMENTS

| | | |
|---|---|---|
| CN | 1597697 A | 3/2005 |
| CN | 1739795 A | 3/2006 |

(Continued)

OTHER PUBLICATIONS

National Center for Biotechnology Information. "PubChem Compound Summary for CID 1110, Succinic Acid" PubChem, https://pubchem.ncbi.nlm.nih.gov/compound/Succinic-Acid. Accessed Sep. 24, 2024 (Year: 2024).*

(Continued)

*Primary Examiner* — Christina Bradley
(74) *Attorney, Agent, or Firm* — Alston & Bird LLP

(57) ABSTRACT

A liquid pharmaceutical formulation, wherein the pharmaceutical formulation comprises a PTH conjugate, a buffering agent, an isotonicity agent, a preservative and optionally an antioxidant and wherein the PTH conjugate comprises a PTH moiety that is covalently and reversibly conjugated to a water-soluble carrier moiety.

8 Claims, No Drawings

Specification includes a Sequence Listing.

(56) References Cited

U.S. PATENT DOCUMENTS

| | | |
|---|---|---|
| 2012/0322721 A1 | 12/2012 | Rasmussen et al. |
| 2013/0116180 A1 | 5/2013 | Gardella et al. |
| 2013/0183349 A1 | 7/2013 | Ho et al. |
| 2014/0011739 A1 | 1/2014 | Klatzmann et al. |
| 2014/0248365 A1 | 9/2014 | Rademacher et al. |
| 2015/0065423 A1 | 3/2015 | Laulicht et al. |
| 2015/0290337 A1 | 10/2015 | Vetter et al. |
| 2016/0264636 A1 | 9/2016 | Rebollo Garcia |
| 2019/0224329 A1 | 7/2019 | Sprogøe et al. |
| 2019/0282668 A1 | 9/2019 | Sprogøe et al. |
| 2020/0023041 A1 | 1/2020 | Holten-Andersen et al. |
| 2020/0046725 A1 | 2/2020 | Cleeman et al. |
| 2020/0276270 A1 | 9/2020 | Holten-Anderson et al. |
| 2020/0276276 A1 | 9/2020 | Sprogøe et al. |
| 2020/0360487 A1 | 11/2020 | Sprogøe et al. |
| 2020/0360488 A1 | 11/2020 | Sprogøe et al. |
| 2020/0376089 A1 | 12/2020 | Sprogøe et al. |
| 2021/0196801 A1 | 7/2021 | Sprogøe t al. |
| 2022/0008516 A1 | 1/2022 | Cleemann et al. |
| 2022/0088149 A1 | 3/2022 | Skands et al. |
| 2023/0042670 A1 | 2/2023 | Sprogøe et al. |
| 2023/0121525 A1 | 4/2023 | Sprogøe et al. |
| 2023/0218722 A1 | 7/2023 | Sprogøe et al. |
| 2023/0248836 A1 | 8/2023 | Sprogøe et al. |
| 2023/0321198 A1 | 10/2023 | Sprogøe et al. |
| 2023/0381284 A1 | 11/2023 | Sprogøe et al. |
| 2024/0173385 A1 | 5/2024 | Sprogøe et al. |
| 2024/0245755 A1 | 7/2024 | Sprogøe et al. |

FOREIGN PATENT DOCUMENTS

| | | |
|---|---|---|
| EP | 0920873 A2 | 6/1999 |
| EP | 1 477 496 A1 | 11/2001 |
| EP | 1534334 B1 | 6/2014 |
| WO | WO 02/089789 | 11/2002 |
| WO | WO 2003/064462 A1 | 8/2003 |
| WO | WO 2005/027978 | 3/2005 |
| WO | WO 2005/099768 | 10/2005 |
| WO | WO 2005/099768 A2 | 10/2005 |
| WO | WO 2005/115441 A2 | 12/2005 |
| WO | WO 2006/003014 | 1/2006 |
| WO | WO 2006/136586 | 12/2006 |
| WO | WO 2006/136586 A2 | 12/2006 |
| WO | WO 2007/106597 A3 | 9/2007 |
| WO | WO 2008/034122 | 3/2008 |
| WO | WO 2008/048784 A1 | 4/2008 |
| WO | WO 2008/155134 | 12/2008 |
| WO | WO 2009/009712 | 1/2009 |
| WO | WO 2009/009712 A1 | 1/2009 |
| WO | WO 2009/053106 A1 | 4/2009 |
| WO | WO 2009/095479 | 8/2009 |
| WO | WO 2009/095479 A1 | 8/2009 |
| WO | WO 2009/143412 | 11/2009 |
| WO | WO 2009/156481 A1 | 12/2009 |
| WO | WO 2010/091122 A1 | 8/2010 |
| WO | WO 2011/012715 | 2/2011 |
| WO | WO 2011/012715 A1 | 2/2011 |
| WO | WO 2011/012718 A1 | 2/2011 |
| WO | WO 2011/012719 A1 | 2/2011 |
| WO | WO 2011/012721 A1 | 2/2011 |
| WO | WO 2011/012722 | 2/2011 |
| WO | WO 2011/012722 A1 | 2/2011 |
| WO | WO 2011/012723 A1 | 2/2011 |
| WO | WO 2011/042450 A1 | 4/2011 |
| WO | WO 2011/082368 | 7/2011 |
| WO | WO 2011/082368 A2 | 7/2011 |
| WO | WO 2011/089214 | 7/2011 |
| WO | WO 2011/089215 | 7/2011 |
| WO | WO 2011/089215 A1 | 7/2011 |
| WO | WO 2011/089216 | 7/2011 |
| WO | WO 2011/089216 A1 | 7/2011 |
| WO | WO 2011/123813 | 10/2011 |
| WO | WO 2011/144756 | 11/2011 |
| WO | WO 2012/035139 A1 | 3/2012 |
| WO | WO 2012/002047 | 5/2012 |
| WO | WO 2013/024048 | 2/2013 |
| WO | WO 2013/024049 | 2/2013 |
| WO | WO 2013/024051 A1 | 2/2013 |
| WO | WO 2013/024052 | 2/2013 |
| WO | WO 2013/024053 | 2/2013 |
| WO | WO 2013/024053 A1 | 2/2013 |
| WO | WO 2013/036857 | 3/2013 |
| WO | WO 2013/053856 A1 | 4/2013 |
| WO | WO 2013/108235 A1 | 7/2013 |
| WO | WO 2013/160340 | 10/2013 |
| WO | WO 2014/033540 | 3/2014 |
| WO | WO 2014/056915 A1 | 4/2014 |
| WO | WO 2014/056923 A1 | 4/2014 |
| WO | WO 2014/056926 | 4/2014 |
| WO | WO 2014/056926 A1 | 4/2014 |
| WO | WO 2014/060512 | 4/2014 |
| WO | WO 2014/086961 A1 | 6/2014 |
| WO | WO 2014/173759 A1 | 10/2014 |
| WO | WO 2015/052155 A1 | 4/2015 |
| WO | WO 2016/020373 | 2/2016 |
| WO | WO 2016/020373 A1 | 2/2016 |
| WO | WO 2016/065042 A1 | 4/2016 |
| WO | WO 2016/110577 A1 | 7/2016 |
| WO | WO 2016/193371 A1 | 12/2016 |
| WO | WO-2017148883 A1 * | 9/2017 ......... A61K 38/1709 |
| WO | WO 2018/060310 A1 | 4/2018 |
| WO | WO 2018/060311 A1 | 4/2018 |
| WO | WO 2018/060312 A1 | 4/2018 |
| WO | WO 2018/100174 A1 | 6/2018 |
| WO | WO 2019/219896 A1 | 11/2019 |
| WO | WO 2020/165087 A1 | 8/2020 |

OTHER PUBLICATIONS

U.S. Appl. No. 17/488,137, filed Sep. 28, 2021, Sprogøe et al.
U.S. Appl. No. 18/028,989, filed Mar. 28, 2023, Sprogøe et al.
U.S. Appl. No. 18/053,701, filed Nov. 8, 2022, Sprogøe et al.
U.S. Appl. No. 18/176,372, filed Feb. 28, 2023, Sprogøe et al.
U.S. Appl. No. 18/355,223, filed Jul. 19, 2023, Sprogøe et al.
Abate, et al., "Review of Hypoparathyroidism," Frontiers Endocrimolgy, vol. 7, Art. 172, (Jan. 2017).
Aouchiche, et al., "Teriparatide administration by the Omnipod pump: preliminary experience from two cases with refractory hypoparathyroidism," Endocrine, 76:179-188, (Jan. 2022).
Arrighi, et al., "Bone healing induced by local delivery of an engineered parathyroid hormone prodrug", Biomaterials, Mar. 1, 2009. 1763-1771, 30(9), Elsevier Science Publishers BV., Barking, GB, XP025928044.
Beauchamp, et al., "A New Procedure for the Synthesis of Polyethylene Glycol-Protein Aducts; Effects on Functin Receptor Recognition, and clearance of Superoxide Dismutase, Lactoferrin, and α2-Macroglobulin," Analytical Biochemistry, 131, 25-33, (1983).
Belikov, "2.6 Relation between chemical structure, properties of substances and their effect on the organism," Pharmaceutical chemistry: study guide, fourth edition, revised and enlarged edition, M.: MEDpress-inform, p. 27-28, (2007), English translation only.
Bilezikean, et al., "Management of Hypoparathyroidism: Present and Future," J Clin Endocrinol Metab, 101(6):2313-2324, (Jun. 2016).
Bowie, et al., Deciphering the Message in Protein Sequences: Tolerance to Amino Acid Substitutions, Science, 1990, 1306-1310, 247.
Chamow, et al., "Modification of CD4 Immunoadhesin with Monomethoxypoly(ethylene glycol) Aldehyde via Reductive Alkylation," Bioconjugate Chem. 5, 133-140, (1994).
Cheng, et al., "Teriparatide—Indications beyond osteoporosis," Indian Journal of Endocrinology and Metabolisum, vol. 16, Issue 3, pp. 343-348, (May-Jun. 2012).
Cuchert, et al., "Summary Report: Indirect comparisons Mehtods and validity," HAS Department of Medecines Assessment, 66 pages, (Jul. 2009).
Cusano et al., "Use of parathyroid hormone in hypoparathyroidism," J Endocrinol Invest., 36(11): 1121-1127, (Dec. 2013).
Dyson, et al., "May's Chemistry of Synthetic Drugs," Longmans, Greens and Co., Ltd., 5th edition, May 1959, 1-20.

(56) References Cited

OTHER PUBLICATIONS

Filpula, et al., "Releasable PEGylation of proteins with customized linkers", Nov. 30, 2007, 29-49, 60(1), Advanced drug delivery reviews, Elsevier, Amsterdam, NL.

Finkelstein, et al., "Effects of Teriparatide Retreatment in Osteoporotic Men and Women," J. Clin Endocrinol Metab, 94(7), 2495-2501, (Jul. 2009).

Florence, et al., Attwood D. Physicochemical principles of pharmacy. 3rd ed.—1998—Easton, Bristol: Aarontype Limited, pp. 18-21, paragraph 1.4.1.

Forteo (teriparatide injection) Label, Highlights of Prescribing Information, Lilly USA, LLC, Initial U.S. Approval: 1987, updated Nov. 2020, revised Sep. 2021.

Gafni, et al., "Daily Parathyroid Hormone 1-34 Replacement Therapy for Hypoparathyroidism Induces Marked Changes in Bone Turnover and Structure," Journal of Bone and Mineral Research, vol. 27, No. 8, pp. 1811-1820, (Aug. 2012).

Harkevic, "Dependence of the Pharmacotherapeutic Effect on the Properties of Drugs and Conditions of their Use," Pharmacology: textbook, tenth edition, revised, enlarged and corrected edition, M.: GEOTARMedia, p. 72-74, (2010), English translation only.

Hohenstein, et al., "Development and validation of a novel cell-based assay for potency determination of human parathyroid honnone (PM)", Journal of Pharmaceutical and Biomedical Analysis, Sep. 2014, 345¬350, 98.

Holten-Anderson, et al, "Design and Preclinical Development of TransCon PTH, an Investigational Sustained-Release PTH Replacement Therapy for Hypoparathyroidism," J Bone Miner Res, doi: 10.1002/jbmr.3824, (Nov. 2019).

Horwitz, et al., "A 7-Day Continuous Infusion of PTH or PTHrP Suppresses Bone Fromation and Uncouples Bone Turnover," Journal of Bone and Mineral Research, vol. 26, No. 9, pp. 2287-2297, (Sep. 2011).

Jakubke, et al., "Amioacids, peptides and proteins," M. Mir Publishers, p. 456 (partial English translation of D6) (1985).

JenKem Technology, USA (accessed by download from http://www,,w.jenkerusa.com/Pages,PEGProducts.aspx on Dec. 18, 2014).

Kahn, et al., Efficacy and Safety of Parathyroid Hormone Replacement With TransCon PTH in Hypoparathyroidism: 26 Week Results From the Phase 3 PaTHway Trial, Journal of Bone and Mineral Research, 38(1):14-25. doi: 10.1002/jbmr.4726 (Jan. 2023).

Karpf, et al., "A Randomized Double-Blind Placebo-Controled First-In-Human Phase 1 Trial of TransCon PTH in Healthy Adults," Journal of Bone and Mineral Research, Vo. 35, No. 8, pp. 1430-1440, (Aug. 2020).

Khan, et al., "Path Forward: A Randomized, Double-Blind Placebo-Controlled Phase 2 Trial of TransCon PTH in Adult Hypoparathyroidism," The Journal of Clinical Endocrinology & Metabolism, vol. 107: e372-e385 (Aug. 2021).

Kostenuik, et al., "Infrequent Delivery of a Long-Acting PTH-Fc Fusion Protein Has Potent Anabolic Effects on Cortical and Cancellous Bone", Journal of Bone and Mineral Research, 2007, 1534-1547, 22(10).

Levine, et al., "Intrinsic bioconjugation for site-specific protein PEGylation at N-terminal serine", Chemical Communications—Chemcom, Jan. 1, 2014, 6909-6912, 50 (52), XP055305086.

Liu, et al., "PEGylation Site-Dependent Structural Heterogeneity Study of MonoPEGylated Human Parathyroid Hormone Fragment hPTH(1-34)" Langmuir, Sep. 30, 2014, 11421-11427, 30(38), XP05505083.

Lui, et al., "PEGylation Site-Dependent Structura Heterogeneity Study of MonoPEGylated Human Parathyroid hormone Fragment hPTH(1-34)," Langmuir, 30, 11421-11427, (2014).

Mannstadt, et al., "Efficacy and safety of recombinant human parthyroid hormone (1-84) in hypoparathyroidism (Replace): a double-blind, placebo-controlled, randomised, phase 3 study," Lancet Diabetes Endocrinol, 1: 275-283, (2013).

Mannstadt, et al., "Safety and Efficacy of 5 Years of Treatment with Recombinant Human Parathyroid Hormone in Adults with Hypoparathyroidism," J Clin Endocrinol Metab, 104(11):5136-5147, (Aug. 2019).

Marx, et al., "Solution Structures of Human Parathyroid Hormone Fragments hPTH(1-34) and hPTH(1-39) and Bovine Parathyroid Hormone Fragment bPTH(1-37)," Biochemical and Biophysical Research Communications, 267, 213-220, (2000).

Maschkowskij, et al., "Maschkowskij M.D. Drugs," M. New Wave Publishers, The Sixteenth Edition, p. 1216, (2012) (Partial English Translation of D5 cited in RU 17038 on Mar. 22, 2021).

Mills, et al., "Estimating the power of indirect Comparisons: A Simulation Study," PLoS ONE, vol. 6, Issue 1, e16237, (Jan. 2011).

Mirza, et al., "Secondary Osteoporosis: Pathophysilolgy and Management," Eur J. Endocrinol. 173(3): R131-R151, doi: 10/.1530/EJE-15-0118, (Sep. 2015). Part 1.

Mirza, et al., "Secondary Osteoporosis: Pathophysilolgy and Management," Eur J. Endocrinol. 173(3): R131-R151, doi: 10/.1530/EJE-15-0118, (Sep. 2015). Part 2.

Mitchell, et al., "Long-Term Follow-Up of Patients with Hypoparathyroidism," J Clin Endocrinol Metab, 97: 4507-4514, (2012).

Na, et al., "Capillary electrophoretic characterization of PEGylated human parathyroid hormone with matrix-assisted laser desorption/ionization time-of-flight mass spectrometry", Analytical Biochemistry, Aug. 15, 2004, 322-328, 331(2), Elsevier, Amsterdam, NL.

Nair, et al., "A simple practice guide for dose conversion between animals and human," J Basicc Clin Pharma, 7:27-31, (Mar. 2016).

NOF Corporation Catalog, NOF Corporation, Drug Delivery Systems Catalogue, Ver. 8, 60 pages, (Apr. 2006).

Pan, et al., "Research progress in hormone replacement therapy for hypoparathyroidism after thyroid surgery," Chinese Journal of General Surgery, vol. 24, No. 5, pp. 728-732, (May 2015).

Pekkolay, et al., "Alternative treatment of resistant hypoparathyroidism by intermittent infusion of teriparatide using an insulin pump: A case report," Turk J Phys Med Rehab, 65(2):198-201, (May 2019).

Ponnapakkam, et al., "Treating osteoporosis by targeting parathyroid hormone to bone" Drug Discov Today, Mar. 2014, 204-208, 19(3).

Rejnmark, et al., "PTH replacement therapy of hypoparathyroidism", Bone, Dept. of Endocrinology and Internal Medicine, Aarhus University Hospital, Aarhus, Denmark, May 1, 2012, 50, XP028922570.

Shah, et al., "Teriparatide Therapy and Reduced Postoperative Hospitalization for Postsurgical Hypoparathyroidism," JAMA Otoaryngol Head Neck Surg., 141(9):822-827, (Aug. 2015).

Sikjaer, et al., "Effects of PTH(1-84) therapy on muscle function and quality of life in hypoparathyroidism: results from a randomized controlled trial," Osteoporos Int, 25:1717-1726, (2014).

Sikjaer, et al., "The Effect of Adding PTH(1-84) to onventional Treatment of Hypoparathyroidism: A Randomized, Placebo-Controlled Study," Journal of Bone and Mineral Research, vol. 26, No. 10, pp. 2358-2370, (Oct. 2011).

Smith, et al., "Relevance of Half-Life in Drug Design," J. Med. Chem., 61, 4273-4282, (May 2018).

Smith, et al., "The pH-Rate Profile for the Hydrosysis of a Peptide Bond," J. Am. Chem. Soc., 120, 8910-8913, (1998).

Song, et al., "Validity of indirect comparison for estimating efficancy of competing interventions: empirical evidence from published meta-analyses," BMJ, vol. 326, (Mar. 2003).

Starkova, "Clinical endocrinology: Guidance", edited by N. T. Starkova, third edition, revised and enlarged edition, SPb: Piter, p. 182 , (2002), English translation only.

Thiruchelvam, et al., "Teriparatide Induced Delayed Persistent Hypecalcemia," Case Reports in Endocrinology, vol. 2014, Article IDS 802473, (2014).

Vilardaga, "Molecular basis of parathyroid hormone receptor signaling and trafficking: a family B GPCR paradigm," Cell Mol. Life, Sci., 68(1): 1-13, (2011).

Vokes, et al., "Reombinant Human Parthyroid Hormone Effect on Health-Related Quality of Life in Adults With Chronic Hypoparathyroidism," J Clin Endocrinol Metab, 103: 722-731, (Nov. 2018).

(56) References Cited

OTHER PUBLICATIONS

Watchorn, "CCLV. The Normal Serum-Calcium and Magnesium of the Rat: Their Relation to Sex and Age," Biochemical Laboratory, Cambridge, 1875-1878, (Nov. 1, 1933).

Wei, et al., The release profiles and bioactivity of parathyroid hormone from poly(lactic-co-glycolic acid) microspheres, Biomaterials, 25, 345-352, (2004).

Winer, et al., "Effects of Pump versus Twice-Daily Injection Delivery of Synthetic Parathyroid Hormone 1-34 in Children with Severe congenital Hypoparathyroidism", J Pediatr., 2014, 556-563, 165(3), NIH, Bethesda, Maryland.

Winer, et al., "Long-Term Treatment of Hypoparathyroidism: A Randomized Controlled Study Comparing Parthyroid Hormone-(1-34) versus Calcitroil and Calcium," The Journal of Clinical Endocrinology & Metabolism, 88(9): 4214-4220, (Sep. 2003).

Winer, et al., "Synthetic Human Parathyroid Hormone 1-34 Replacement Therapy: A Randomized Crossover Trial Comparing Pumb Versus Injections in the Treatment of Chronic Hypoparathyroidism," J Clin Endocrinol Metab, 97(2):391-399, (2012).

Winer, et al., Synthetic Human Parathyroid Hormone 1-34 vs Calcitriol and Calcium in the Treatment of Hypoparathyroidism, JAMA, 276:631-636, (1996).

Wu, et al., "Disruption of YPS1 and PEP4 genes reduces proteolytic degration of secreted HSA/PTH in Pichia pastoris GS115," J. Ind Microbiol Biotechnol., 40:589-599, (2013).

Zhang, et al., "Molecular-Target-Based Anticancer Photosensitizer: Synthesis and in vitro Photodynamic Activity of Erlotinib-Zinc(II) Phthalocyanine Conjugates," ChemMedChem, 10. 312-320, (Feb. 2015).

Zulenko, et al., "2.3 Dosage of Drugs," Pharmacology. M .: Kolos S, p. 34-35, (2008), English translation only.

New Zealand 751745 Patent examination report 2 dated Jan. 26, 2023.

U.S. Appl. No. 16/118,155, Non-Final Office Action mailed Feb. 11, 2021.
U.S. Appl. No. 16/118,155, Requirement for Restriction/Election mailed Oct. 7, 2020.
U.S. Appl. No. 16/337,713, Final Office Action mailed Aug. 23, 2021.
U.S. Appl. No. 16/337,713, Final Office Action mailed Sep. 1, 2020.
U.S. Appl. No. 16/337,713, Final Office Action mailed Sep. 1, 2022.
U.S. Appl. No. 16/337,713, Non-Final Office Action mailed Feb. 22, 2021.
U.S. Appl. No. 16/337,713, Non-Final Office Action mailed Mar. 25, 2020.
U.S. Appl. No. 16/337,713, Non-Final Office Action mailed May 27, 2022.
U.S. Appl. No. 16/337,713, Notice of Allowance mailed Oct. 26, 2022.
U.S. Appl. No. 16/337,803, Final Office Action mailed Feb. 28, 2023.
U.S. Appl. No. 16/337,803, Final Office Action mailed May 3, 2021.
U.S. Appl. No. 16/337,803, Final Office Action mailed Sep. 21, 2022.
U.S. Appl. No. 16/337,803, Non-Final Office Action mailed Feb. 15, 2024.
U.S. Appl. No. 16/337,803, Non-Final Office Action mailed Jan. 12, 2021.
U.S. Appl. No. 16/337,803, Non-Final Office Action mailed Mar. 7, 2022.
U.S. Appl. No. 16/337,803, Requirement for Restriction/Election mailed Jun. 10, 2020.
U.S. Appl. No. 16/337,955, Corrected Notice of Allowance mailed Dec. 5, 2022.
U.S. Appl. No. 16/337,955, Final Office Action mailed Jan. 7, 2022.
U.S. Appl. No. 16/337,955, Final Office Action mailed Apr. 15, 2022.
U.S. Appl. No. 16/337,955, Final Office Action mailed Jul. 14, 2022.
U.S. Appl. No. 16/337,955, Non-Final Office Action mailed Jul. 16, 2020.
U.S. Appl. No. 16/337,955, Non-Final Office Action mailed Sep. 7, 2021.
U.S. Appl. No. 16/337,955, Notice of Allowability mailed Apr. 19, 2023.
U.S. Appl. No. 16/337,955, Notice of Allowance mailed Mar. 3, 2023.
U.S. Appl. No. 16/337,955, Notice of Allowance mailed Sep. 6, 2022.
U.S. Appl. No. 16/337,955, Notice of Allowance mailed Oct. 19, 2022.
U.S. Appl. No. 16/988,302, Final Office Action mailed Apr. 27, 2023.
U.S. Appl. No. 16/988,302, Requirement for Restriction/Election mailed Jan. 14, 2022.
U.S. Appl. No. 16/988,386, Requirement for Restriction/Election mailed Jul. 6, 2022.
U.S. Appl. No. 16/989,225, Non-Final Office Action mailed Sep. 7, 2021.
U.S. Appl. No. 16/989,225, Requirement for Restriction/Election mailed May 14, 2021.
U.S. Appl. No. 17/055,695, Advisory Action mailed Jun. 24, 2024.
U.S. Appl. No. 17/055,695, Final Office Action mailed Feb. 7, 2024.
U.S. Appl. No. 17/055,695, Final Office Action mailed May 19, 2023.
U.S. Appl. No. 17/055,695, Non-Final Office Action mailed Aug. 25, 2023.
U.S. Appl. No. 17/055,695, Requirement for Restriction/Election mailed Jul. 21, 2022.
U.S. Appl. No. 17/488,137, Final Office Action mailed May 13, 2022.
U.S. Appl. No. 17/488,137, Non-Final Office Action mailed Feb. 4, 2022.
U.S. Appl. No. 17/488,137, Requirement for Restriction/Election mailed Nov. 9, 2021.
U.S. Appl. No. 18/053,693, Non-Final Office Action mailed Mar. 20, 2023.
U.S. Appl. No. 18/053,693, Notice of Allowance and Interview Summary mailed Jul. 19, 2023.
U.S. Appl. No. 18/053,693, Requirement for Restriction/Election mailed Jan. 27, 2023.
U.S. Appl. No. 18/053,701, Non-Final Office Action mailed Jun. 22, 2023.
U.S. Appl. No. 18/053,701, Notice of Allowance mailed Oct. 2, 2023.
U.S. Appl. No. 18/063,294, Corrected Notice of Allowance mailed Oct. 2, 2023.
U.S. Appl. No. 18/063,294, Non-Final Office Action mailed Aug. 23, 2023.
U.S. Appl. No. 18/063,294, Notice of Allowance mailed Jun. 20, 2023.
U.S. Appl. No. 18/063,294, Notice of Allowance mailed Sep. 11, 2023.
U.S. Appl. No. 18/355,223, Non-Final Office Action mailed Sep. 21, 2023.
U.S. Appl. No. 18/355,223, Notice of Allowance mailed Nov. 2, 2023.
U.S. Appl. No. 18/421,786, Non-Final Office Action mailed Sep. 5, 2024.
U.S. Appl. No. 18/464,0-46, Non-Final Office Action mailed Apr. 8, 2024.
Corrected U.S. Appl. No. 18/053,701, Notice of Allowance mailed Oct. 5, 2023.
U.S. Appl. No. 16/118,155, Final Office Action mailed Sep. 28, 2018.
U.S. Appl. No. 16/988,302, Non-Final Office Action mailed Oct. 3, 2022.
U.S. Appl. No. 16/988,386, Final Office Action mailed May 2, 2023.
U.S. Appl. No. 17/055,695, Non-Final Office Action mailed Nov. 21, 2022.
U.S. Appl. No. 18/063,294, Non-Final Office Action mailed Apr. 28, 2023.

(56) References Cited

OTHER PUBLICATIONS

U.S. Appl. No. 18/176,372, Non-Final Office Action mailed Apr. 5, 2024.
U.S. Appl. No. 16/337,955 Advisory Action mailed Feb. 16, 2021.
U.S. Appl. No. 16/337,955 Final Office Action mailed Dec. 3, 2020.
WIPO Application No. PCT/EP2017/054550, PCT International Preliminary Report on Patentability mailed Sep. 4, 2018.
WIPO Application No. PCT/EP2017/054550, PCT International Search Report and Written Opinion of the International Searching Authority mailed Sep. 8, 2017.
WIPO Application No. PCT/EP2017/074592, PCT International Preliminary Report on Patentability mailed Apr. 2, 2019.
WIPO Application No. PCT/EP2017/074592, PCT International Search Report and Written Opinion of the International Searching Authority mailed Apr. 5, 2018.
WIPO Application No. PCT/EP2017/074594, PCT International Preliminary Report on Patentability mailed Apr. 2, 2019.
WIPO Application No. PCT/EP2017/074594, PCT International Search Report and Written Opinion of the International Searching Authority mailed Apr. 5, 2018.
WIPO Application No. PCT/EP2019/062773, PCT International Preliminary Report on Patentability mailed Nov. 24, 2020.
WIPO Application No. PCT/EP2019/062773, PCT International Search Report and Written Opinion of the International Searching Authority mailed Nov. 21, 2019.
WIPO Application No. PCT/EP2020/053316, PCT International Search Report and Written Opinion of the International Searching Authority mailed Sep. 4, 2020.
U.S. Appl. No. 16/337,803, Non-Final Office Action mailed Oct. 23, 2024.
U.S. Appl. No. 18/464,046, Notice of Allowance mailed Sep. 9, 2024.
Daugherty et al., "Formulation and delivery issues for monoclonal antibody therapeutics," Advanced Drug Delivery Reviews 58, 686-706, (May 2006).
Patro et al., "Protein formulation and fill-finish operations," Biotechnology Annual Review, vol. 8, 55-84, (2002).
Wang, "Instability, stabilization, and formulation of liquid protein pharmaceuticals," International Journal of Pharmaceutics, 185, 129-188, (1999).

\* cited by examiner

LIQUID PHARMACEUTICAL FORMULATIONS OF PTH CONJUGATES

CROSS-REFERENCE TO RELATED APPLICATIONS

This application is the US national stage entry of PCT/EP2020/053316 filed Feb. 10, 2020, which claims the benefit of EP Application Serial No. 19156485.5 filed Feb. 11, 2019 and EP Application Serial No. 19168857.1 filed Apr. 12, 2019.

REFERENCE TO SEQUENCE LISTING

This application includes an electronic sequence listing in a file named 562997SEQLST.TXT, created on Aug. 2, 2021 and containing 75,397 bytes, which is incorporated by reference.

The present invention relates to liquid pharmaceutical formulations comprising a PTH conjugate, a buffering agent, an isotonicity agent, a preservative and optionally an antioxidant.

Hypoparathyroidism is a rare endocrine disease with low serum calcium and inappropriately low (insufficient) circulating parathyroid hormone levels, most often in adults secondary to thyroid surgery. Patients who underwent immunotherapy targeting immune checkpoint molecules such as cytotoxic T lymphocyte antigen-4 (CTLA-4), programmed cell death protein 1 (PD-1) and its ligand PD-L1 may also develop hypoparathyroidism as an immune-related adverse event on the parathyroid glands. Standard treatment for hypoparathyroidism includes activated vitamin D analogues and calcium supplementation, which increases calcium and phosphorus absorption and serum levels at the expense of abnormally increased urinary calcium excretion.

PTH is an endocrine hormone which is secreted from the parathyroid gland in response to decreased calcium levels. In 2015, Natpara, PTH (1-84), was approved for once-daily subcutaneous injection as an adjunct to vitamin D and calcium in patients with hypoparathyroidism. While this represents an important advance in the treatment of the disease, Natpara has not demonstrated an ability to reduce incidences of hypercalcemia (elevated serum calcium levels), hypocalcemia (low serum calcium), or hypercalciuria (elevated urinary calcium) relative to conventional therapy in treated patients.

PTH is rapidly absorbed and metabolized when given by subcutaneous route as it is degraded by proteases. As such, there is a high need for improved PTH based therapies for hypoparathyroidism.

The conjugation of PTH to PEG by PEGylation is one approach for improving the biological stability. WO 2003/064462 A1 discloses pharmaceutical formulations comprising stable conjugates of PTH (1-34) and Cys-PTH (1-35) and PEG derivatives. Although this application also suggests that PTH variants and water-soluble polymers may be connected via a hydrolysable linkage obtained by reaction of an aldehyde-PEG and the amine groups on PTH, it does not provide any details as how to obtain or store such conjugates until administration.

An expansion of the scope of increasing the in vivo half-life of PTH based on conjugation to water-soluble carrier moieties such as PEG, via reversible prodrug linkers was explored in WO 2017/148883 A1, WO 2018/060310 A1, WO 2018/060311 A1 and WO 2018/060312 A1. However, no information regarding liquid pharmaceutical formulations that allows for stable storage of these reversible conjugates is provided.

Pharmaceutical formulations of such PTH conjugates, wherein the water-soluble carrier is attached to PTH via a reversible linkage, have to provide for sufficient stability of the PTH conjugate in order to avoid premature PTH release during storage. In case the reversible linkage between the carrier and PTH is degraded during storage, the concentration of the readily available drug is increased. This could result in the administration of supraphysiological levels of PTH leading to risk of overdosage upon administration, which may result in hypercalcemia or osteopenia. Therefore, achieving a sustained release of PTH that will maintain calcium homeostasis and normal rates of turnover is important for the treatment of hypoparathyroidism.

In addition, any drug released during storage is subject to rapid renal clearance upon application to a patient, and consequently the time for which the long-acting formulation provides therapeutically relevant amounts of drug is reduced.

Furthermore, it is known that PTH or its variants, conjugates or derivatives may undergo degradation reactions during storage which may result in the formation of impurities/peptide damage within the corresponding formulation, such as:
  degradation products resulted from the oxidation of methionine (Met/M) residues to methionine sulfoxide and methionine sulfone;
  degradation products resulted from the oxidation of tryptophan (Trp/T) residues to oxindole-3-alanine, 5-hydroxytryptophan or via dioxidation to N-formylkynurenine and kynurenine;
  degradation products resulted from the isomerization of aspartic acid (Asp/D) or aspartate residues to isoaspartic acid or isoaspartate such as via a succinimide intermediate;
  degradation products such as C-terminal Asp truncated peptides resulted from the peptide bond cleavage at the aspartic acid or aspartate residue;
  degradation products resulted from the deamidation of asparagine residues (Asn/N), to aspartic acid or aspartate and/or to isoaspartic acid or isoaspartate such as via a succinimide intermediate;
  degradation products such as C-terminal Asn or Asp truncated peptides resulted from the peptide bond cleavage at the asparagine residue;
  degradation products resulted from the deamidation of glutamine residues (Gln/Q), to glutamic acid or isoglutamic acid such as via a glutarimide intermediate; and
  aggregates resulted from the aggregation of the peptide.

As the aforementioned degradation products or aggregates that may form during storage may impair the bioactivity of the PTH moiety, it is thus desirable to minimize their formation during storage. Moreover, the reversible linkage between the PTH moiety and the water-soluble carrier makes the storage of the liquid pharmaceutical formulation comprising the PTH conjugates challenging.

It is thus important to identify suitable liquid pharmaceutical formulations of PTH conjugates comprising PTH covalently linked via a reversible linker to a water-soluble carrier, wherein the peptide will exhibit an acceptable impurity profile and limited premature PTH-release even after extended storage.

It is thus an object of the present invention to at least partially overcome the shortcomings described above.

This object is achieved with a liquid pharmaceutical formulation, wherein the liquid pharmaceutical formulation comprises a PTH conjugate, a buffering agent, an isotonicity agent, a preservative and optionally an antioxidant and wherein the PTH conjugate comprises a PTH moiety that is covalently and reversibly conjugated to a water-soluble carrier moiety.

It was surprisingly found that the liquid pharmaceutical formulation of the present invention allows for stable long-term storage. Moreover, it was surprisingly found that the aggregation of the PTH conjugate in the liquid pharmaceutical formulation was reduced in the liquid pharmaceutical formulation of the present invention.

Within the meaning of the present invention the terms are used as follows.

As used herein, the term "PTH" refers to all PTH polypeptides, in certain embodiments from mammalian species, such as from human and mammalian species, in particular from human and murine species, as well as their variants, analogs, orthologs, homologs, and derivatives and fragments thereof, that are characterized by raising serum calcium and renal phosphorus excretion and lowering serum phosphorus and renal calcium excretion.

The term "PTH" also refers to all PTHrP polypeptides that bind to and activate the common PTH/PTHrP1 receptor. In certain embodiments, the term "PTH" refers to the PTH polypeptide as well as its variants, homologs and derivatives exhibiting essentially the same biological activity, i.e. raising serum calcium and renal phosphorus excretion, and lowering serum phosphorus and renal calcium excretion.

As used herein, the term "PTH polypeptide variant" refers to a polypeptide from the same species that differs from a reference PTH or PTHrP polypeptide. In certain embodiments, such reference is a PTH polypeptide sequence. Generally, differences are limited so that the amino acid sequence of the reference and the variant are closely similar overall and, in many regions, identical. In certain embodiments, PTH polypeptide variants are at least 70%, 80%, 90%, or 95% identical to a reference PTH or PTHrP polypeptide. By a polypeptide having an amino acid sequence at least, for example, 95% "identical" to a query amino acid sequence, it is intended that the amino acid sequence of the subject polypeptide is identical to the query sequence except that the subject polypeptide sequence may include up to five amino acid alterations per each 100 amino acids of the query amino acid sequence. These alterations of the reference sequence may occur at the amino (N-terminal) or carboxy terminal (C-terminal) positions of the reference amino acid sequence or anywhere between those terminal positions, interspersed either individually among residues in the reference sequence or in one or more contiguous groups within the reference sequence. The query sequence may be an entire amino acid sequence of the reference sequence or any fragment specified as described herein.

Such PTH polypeptide variants may be naturally occurring variants, such as naturally occurring allelic variants encoded by one of several alternate forms of a PTH or PTHrP occupying a given locus on a chromosome or an organism, or isoforms encoded by naturally occurring splice variants originating from a single primary transcript. Alternatively, a PTH polypeptide variant may be a variant that is not known to occur naturally and that can be made by mutagenesis techniques known in the art.

It is known in the art that one or more amino acids may be deleted from the N-terminus or C-terminus of a bioactive polypeptide without substantial loss of biological function. Such N- and/or C-terminal deletions are also encompassed by the term PTH polypeptide variant.

It is also recognized by one of ordinary skill in the art that some amino acid sequences of PTH or PTHrP polypeptides can be varied without significant effect of the structure or function of the polypeptide. Such mutants include deletions, insertions, inversions, repeats, and substitutions selected according to general rules known in the art so as to have little effect on activity. For example, guidance concerning how to make phenotypically silent amino acid substitutions is provided in Bowie et al. (1990), Science 247:1306-1310, which is hereby incorporated by reference in its entirety, wherein the authors indicate that there are two main approaches for studying the tolerance of the amino acid sequence to change.

PTH variants may also be peptides in which any one or more, up to all, residues susceptible to deamidation or a deamidation-like reaction (e.g., isomerization) are intentionally converted to other residues prior to storage via deamidation or a deamidation-like reaction to any extent, up to 100% conversion per converted residue. PTH variants may also be peptides in which any one or more, up to all, residues susceptible to oxidation are intentionally converted to other residues prior to storage to any extent, up to 100% conversion per converted residue.

In certain embodiments, the term "PTH" refers to the following polypeptide sequences:

```
SEQ ID NO: 1 (PTH 1-84):
SVSEIQLMHNLGKHLNSMERVEWLRKKLQDVHNFVALGAPLAPRDAGSQRPRKK

EDNVLVESHEKSLGEADKADVNVLTKAKSQ

SEQ ID NO: 2 (PTH 1-83):
SVSEIQLMHNLGKHLNSMERVEWLRKKLQDVHNFVALGAPLAPRDAGSQRPRKK

EDNVLVESHEKSLGEADKADVNVLTKAKS

SEQ ID NO: 3 (PTH 1-82):
SVSEIQLMHNLGKHLNSMERVEWLRKKLQDVHNFVALGAPLAPRDAGSQRPRKK

EDNVLVESHEKSLGEADKADVNVLTKAK

SEQ ID NO: 4 (PTH 1-81):
SVSEIQLMHNLGKHLNSMERVEWLRKKLQDVHNFVALGAPLAPRDAGSQRPRKK

EDNVLVESHEKSLGEADKADVNVLTKA

SEQ ID NO: 5 (PTH 1-80):
SVSEIQLMHNLGKHLNSMERVEWLRKKLQDVHNFVALGAPLAPRDAGSQRPRKK
```

-continued

EDNVLVESHEKSLGEADKADVNVLTK

SEQ ID NO: 6 (PTH 1-79):
SVSEIQLMHNLGKHLNSMERVEWLRKKLQDVHNFVALGAPLAPRDAGSQRPRKK

EDNVLVESHEKSLGEADKADVNVLT

SEQ ID NO: 7 (PTH 1-78):
SVSEIQLMHNLGKHLNSMERVEWLRKKLQDVHNFVALGAPLAPRDAGSQRPRKK

EDNVLVESHEKSLGEADKADVNVL

SEQ ID NO: 8 (PTH 1-77):
SVSEIQLMHNLGKHLNSMERVEWLRKKLQDVHNFVALGAPLAPRDAGSQRPRKK

EDNVLVESHEKSLGEADKADVNV

SEQ ID NO: 9 (PTH 1-76):
SVSEIQLMHNLGKHLNSMERVEWLRKKLQDVHNFVALGAPLAPRDAGSQRPRKK

EDNVLVESHEKSLGEADKADVN

SEQ ID NO: 10 (PTH 1-75):
SVSEIQLMHNLGKHLNSMERVEWLRKKLQDVHNFVALGAPLAPRDAGSQRPRKK

EDNVLVESHEKSLGEADKADV

SEQ ID NO: 11 (PTH 1-74):
SVSEIQLMHNLGKHLNSMERVEWLRKKLQDVHNFVALGAPLAPRDAGSQRPRKK

EDNVLVESHEKSLGEADKAD

SEQ ID NO: 12 (PTH 1-73):
SVSEIQLMHNLGKHLNSMERVEWLRKKLQDVHNFVALGAPLAPRDAGSQRPRKK

EDNVLVESHEKSLGEADKA

SEQ ID NO: 13 (PTH 1-72):
SVSEIQLMHNLGKHLNSMERVEWLRKKLQDVHNFVALGAPLAPRDAGSQRPRKK

EDNVLVESHEKSLGEADK

SEQ ID NO: 14 (PTH 1-71):
SVSEIQLMHNLGKHLNSMERVEWLRKKLQDVHNFVALGAPLAPRDAGSQRPRKK

EDNVLVESHEKSLGEAD

SEQ ID NO: 15 (PTH 1-70):
SVSEIQLMHNLGKHLNSMERVEWLRKKLQDVHNFVALGAPLAPRDAGSQRPRKK

EDNVLVESHEKSLGEA

SEQ ID NO: 16 (PTH 1-69):
SVSEIQLMHNLGKHLNSMERVEWLRKKLQDVHNFVALGAPLAPRDAGSQRPRKK

EDNVLVESHEKSLGE

SEQ ID NO: 17 (PTH 1-68):
SVSEIQLMHNLGKHLNSMERVEWLRKKLQDVHNFVALGAPLAPRDAGSQRPRKK

EDNVLVESHEKSLG

SEQ ID NO: 18 (PTH 1-67):
SVSEIQLMHNLGKHLNSMERVEWLRKKLQDVHNFVALGAPLAPRDAGSQRPRKK

EDNVLVESHEKSL

SEQ ID NO: 19 (PTH 1-66):
SVSEIQLMHNLGKHLNSMERVEWLRKKLQDVHNFVALGAPLAPRDAGSQRPRKK

EDNVLVESHEKS

SEQ ID NO: 20 (PTH 1-65):
SVSEIQLMHNLGKHLNSMERVEWLRKKLQDVHNFVALGAPLAPRDAGSQRPRKK

EDNVLVESHEK

SEQ ID NO: 21 (PTH 1-64):
SVSEIQLMHNLGKHLNSMERVEWLRKKLQDVHNFVALGAPLAPRDAGSQRPRKK

EDNVLVESHE

-continued

SEQ ID NO: 22 (PTH 1-63):
SVSEIQLMHNLGKHLNSMERVEWLRKKLQDVHNFVALGAPLAPRDAGSQRPRKK
EDNVLVESH

SEQ ID NO: 23 (PTH 1-62):
SVSEIQLMHNLGKHLNSMERVEWLRKKLQDVHNFVALGAPLAPRDAGSQRPRKK
EDNVLVES

SEQ ID NO: 24 (PTH 1-61):
SVSEIQLMHNLGKHLNSMERVEWLRKKLQDVHNFVALGAPLAPRDAGSQRPRKK
EDNVLVE

SEQ ID NO: 25 (PTH 1-60):
SVSEIQLMHNLGKHLNSMERVEWLRKKLQDVHNFVALGAPLAPRDAGSQRPRKK
EDNVLV

SEQ ID NO: 26 (PTH 1-59):
SVSEIQLMHNLGKHLNSMERVEWLRKKLQDVHNFVALGAPLAPRDAGSQRPRKK
EDNVL

SEQ ID NO: 27 (PTH 1-58):
SVSEIQLMHNLGKHLNSMERVEWLRKKLQDVHNFVALGAPLAPRDAGSQRPRKK
EDNV

SEQ ID NO: 28 (PTH 1-57):
SVSEIQLMHNLGKHLNSMERVEWLRKKLQDVHNFVALGAPLAPRDAGSQRPRKK
EDN

SEQ ID NO: 29 (PTH 1-56):
SVSEIQLMHNLGKHLNSMERVEWLRKKLQDVHNFVALGAPLAPRDAGSQRPRKK
ED

SEQ ID NO: 30 (PTH 1-55):
SVSEIQLMHNLGKHLNSMERVEWLRKKLQDVHNFVALGAPLAPRDAGSQRPRKK
E

SEQ ID NO: 31 (PTH 1-54):
SVSEIQLMHNLGKHLNSMERVEWLRKKLQDVHNFVALGAPLAPRDAGSQRPRKK

SEQ ID NO: 32 (PTH 1-53):
SVSEIQLMHNLGKHLNSMERVEWLRKKLQDVHNFVALGAPLAPRDAGSQRPRK

SEQ ID NO: 33 (PTH 1-52):
SVSEIQLMHNLGKHLNSMERVEWLRKKLQDVHNFVALGAPLAPRDAGSQRPR

SEQ ID NO: 34 (PTH 1-51):
SVSEIQLMHNLGKHLNSMERVEWLRKKLQDVHNFVALGAPLAPRDAGSQRP

SEQ ID NO: 35 (PTH 1-50):
SVSEIQLMHNLGKHLNSMERVEWLRKKLQDVHNFVALGAPLAPRDAGSQR

SEQ ID NO: 36 (PTH 1-49):
SVSEIQLMHNLGKHLNSMERVEWLRKKLQDVHNFVALGAPLAPRDAGSQ

SEQ ID NO: 37 (PTH 1-48):
SVSEIQLMHNLGKHLNSMERVEWLRKKLQDVHNFVALGAPLAPRDAGS

SEQ ID NO: 38 (PTH 1-47):
SVSEIQLMHNLGKHLNSMERVEWLRKKLQDVHNFVALGAPLAPRDAG

SEQ ID NO: 39 (PTH 1-46):
SVSEIQLMHNLGKHLNSMERVEWLRKKLQDVHNFVALGAPLAPRDA

SEQ ID NO: 40 (PTH 1-45):
SVSEIQLMHNLGKHLNSMERVEWLRKKLQDVHNFVALGAPLAPRD

SEQ ID NO: 41 (PTH 1-44):
SVSEIQLMHNLGKHLNSMERVEWLRKKLQDVHNFVALGAPLAPR

SEQ ID NO: 42 (PTH 1-43):
SVSEIQLMIHNLGKHLNSMERVEWLRKKLQDVHNFVALGAPLAP

SEQ ID NO: 43 (PTH 1-42):
SVSEIQLMHNLGKHLNSMERVEWLRKKLQDVHNFVALGAPLA

SEQ ID NO: 44 (PTH 1-41):
SVSEIQLMHNLGKHLNSMERVEWLRKKLQDVHNFVALGAPL

SEQ ID NO: 45 (PTH 1-40):
SVSEIQLMHNLGKHLNSMERVEWLRKKLQDVHNFVALGAP

SEQ ID NO: 46 (PTH 1-39):
SVSEIQLMHNLGKHLNSMERVEWLRKKLQDVHNFVALGA

SEQ ID NO: 47 (PTH 1-38):
SVSEIQLMHNLGKHLNSMERVEWLRKKLQDVHNFVALG

SEQ ID NO: 48 (PTH 1-37):
SVSEIQLMHNLGKHLNSMERVEWLRKKLQDVHNFVAL

SEQ ID NO: 49 (PTH 1-36):
SVSEIQLMHNLGKHLNSMERVEWLRKKLQDVHNFVA

SEQ ID NO: 50 (PTH 1-35):
SVSEIQLMHNLGKHLNSMERVEWLRKKLQDVHNFV

SEQ ID NO: 51 (PTH 1-34):
SVSEIQLMHNLGKHLNSMERVEWLRKKLQDVHNF

SEQ ID NO: 52 (PTH 1-33):
SVSEIQLMHNLGKHLNSMERVEWLRKKLQDVHN

SEQ ID NO: 53 (PTH 1-32):
SVSEIQLMHNLGKHLNSMERVEWLRKKLQDVH

SEQ ID NO: 54 (PTH 1-31):
SVSEIQLMHNLGKHLNSMERVEWLRKKLQDV

SEQ ID NO: 55 (PTH 1-30):
SVSEIQLMHNLGKHLNSMERVEWLRKKLQD

SEQ ID NO: 56 (PTH 1-29):
SVSEIQLMHNLGKHLNSMERVEWLRKKLQ

SEQ ID NO: 57 (PTH 1-28):
SVSEIQLMHNLGKHLNSMERVEWLRKKL

SEQ ID NO: 58 (PTH 1-27):
SVSEIQLMHNLGKHLNSMERVEWLRKK

SEQ ID NO: 59 (PTH 1-26):
SVSEIQLMHNLGKHLNSMERVEWLRK

SEQ ID NO: 60 (PTH 1-25):
SVSEIQLMHNLGKHLNSMERVEWLR

SEQ ID NO: 61 (amidated PTH 1-84):
SVSEIQLMHNLGKHLNSMERVEWLRKKLQDVHNFVALGAPLAPRDAGSQRPRKK EDNVLVESHEKSLGEADKADVNVLTKAKSQ; wherein the C-terminus is amidated SEQ ID NO: 62 (amidated PTH 1-83):
SVSEIQLMHNLGKHLNSMERVEWLRKKLQDVHNFVALGAPLAPRDAGSQRPRKK EDNVLVESHEKSLGEADKADVNVLTKAKS; wherein the C-terminus is amidated SEQ ID NO: 63 (amidated PTH 1-82):
SVSEIQLMHNLGKHLNSMERVEWLRKKLQDVHNFVALGAPLAPRDAGSQRPRKK EDNVLVESHEKSLGEADKADVNVLTKAK; wherein the C-terminus is amidated SEQ ID NO: 64 (amidated PTH 1-81):
SVSEIQLMHNLGKHLNSMERVEWLRKKLQDVHNFVALGAPLAPRDAGSQRPRKK EDNVLVESHEKSLGEADKADVNVLTKA; wherein the C-terminus is amidated SEQ ID NO: 65 (amidated PTH 1-80):
SVSEIQLMHNLGKHLNSMERVEWLRKKLQDVHNFVALGAPLAPRDAGSQRPRKK EDNVLVESHEKSLGEADKADVNVLTK; wherein the C-terminus is amidated SEQ ID NO: 66 (amidated PTH 1-79):
SVSEIQLMHNLGKHLNSMERVEWLRKKLQDVHNFVALGAPLAPRDAGSQRPRKK
EDNVLVESHEKSLGEADKADVNVLT; wherein the C-terminus is amidated SEQ ID NO: 67 (amidated PTH 1-78):
SVSEIQLMHNLGKHLNSMERVEWLRKKLQDVHNFVALGAPLAPRDAGSQRPRKK
EDNVLVESHEKSLGEADKADVNVL; wherein the C-terminus is amidated SEQ ID NO: 68 (amidated PTH 1-77):
SVSEIQLMHNLGKHLNSMERVEWLRKKLQDVHNFVALGAPLAPRDAGSQRPRKK
EDNVLVESHEKSLGEADKADVNV; wherein the C-terminus is amidated SEQ ID NO: 69 (amidated PTH 1-76):
SVSEIQLMHNLGKHLNSMERVEWLRKKLQDVHNFVALGAPLAPRDAGSQRPRKK
EDNVLVESHEKSLGEADKADVN; wherein the C-terminus is amidated SEQ ID NO: 70 (amidated PTH 1-75):
SVSEIQLMHNLGKHLNSMERVEWLRKKLQDVHNFVALGAPLAPRDAGSQRPRKK
EDNVLVESHEKSLGEADKADV; wherein the C-terminus is amidated SEQ ID NO: 71 (amidated PTH 1-74):
SVSEIQLMHNLGKHLNSMERVEWLRKKLQDVHNFVALGAPLAPRDAGSQRPRKK
EDNVLVESHEKSLGEADKAD; wherein the C-terminus is amidated SEQ ID NO: 72 (amidated PTH 1-73):
SVSEIQLMHNLGKHLNSMERVEWLRKKLQDVHNFVALGAPLAPRDAGSQRPRKK
EDNVLVESHEKSLGEADKA; wherein the C-terminus is amidated SEQ ID NO: 73 (amidated PTH 1-72):
SVSEIQLMHNLGKHLNSMERVEWLRKKLQDVHNFVALGAPLAPRDAGSQRPRKK
EDNVLVESHEKSLGEADK; wherein the C-terminus is amidated SEQ ID NO: 74 (amidated PTH 1-71):
SVSEIQLMHNLGKHLNSMERVEWLRKKLQDVHNFVALGAPLAPRDAGSQRPRKK
EDNVLVESHEKSLGEAD; wherein the C-terminus is amidated SEQ ID NO: 75 (amidated PTH 1-70):
SVSEIQLMHNLGKHLNSMERVEWLRKKLQDVHNFVALGAPLAPRDAGSQRPRKK
EDNVLVESHEKSLGEA; wherein the C-terminus is amidated SEQ ID NO: 76 (amidated PTH 1-69):
SVSEIQLMHNLGKHLNSMERVEWLRKKLQDVHNFVALGAPLAPRDAGSQRPRKK
EDNVLVESHEKSLGE; wherein the C-terminus is amidated SEQ ID NO: 77 (amidated PTH 1-68):
SVSEIQLMHNLGKHLNSMERVEWLRKKLQDVHNFVALGAPLAPRDAGSQRPRKK
EDNVLVESHEKSLG; wherein the C-terminus is amidated SEQ ID NO: 78 (amidated PTH 1-67):
SVSEIQLMHNLGKHLNSMERVEWLRKKLQDVHNFVALGAPLAPRDAGSQRPRKK
EDNVLVESHEKSL; wherein the C-terminus is amidated SEQ ID NO: 79 (amidated PTH 1-66):
SVSEIQLMHNLGKHLNSMERVEWLRKKLQDVHNFVALGAPLAPRDAGSQRPRKK
EDNVLVESHEKS; wherein the C-terminus is amidated SEQ ID NO: 80 (amidated PTH 1-65):
SVSEIQLMHNLGKHLNSMERVEWLRKKLQDVHNFVALGAPLAPRDAGSQRPRKK
EDNVLVESHEK; wherein the C-terminus is amidated SEQ ID NO: 81 (amidated PTH 1-64):
SVSEIQLMHNLGKHLNSMERVEWLRKKLQDVHNFVALGAPLAPRDAGSQRPRKK
EDNVLVESHE; wherein the C-terminus is amidated -continued SEQ ID NO: 82 (amidated PTH 1-63):
SVSEIQLMHNLGKHLNSMERVEWLRKKLQDVHNFVALGAPLAPRDAGSQRPRKK
EDNVLVESH; wherein the C-terminus is amidated SEQ ID NO: 83 (amidated PTH 1-62):
SVSEIQLMHNLGKHLNSMERVEWLRKKLQDVHNFVALGAPLAPRDAGSQRPRKK
EDNVLVES; wherein the C-terminus is amidated SEQ ID NO: 84 (amidated PTH 1-61):
SVSEIQLMHNLGKHLNSMERVEWLRKKLQDVHNFVALGAPLAPRDAGSQRPRKK
EDNVLVE; wherein the C-terminus is amidated SEQ ID NO: 85 (amidated PTH 1-60):
SVSEIQLMHNLGKHLNSMERVEWLRKKLQDVHNFVALGAPLAPRDAGSQRPRKK
EDNVLV; wherein the C-terminus is amidated SEQ ID NO: 86 (amidated PTH 1-59):
SVSEIQLMHNLGKHLNSMERVEWLRKKLQDVHNFVALGAPLAPRDAGSQRPRKK
EDNVL; wherein the C-terminus is amidated SEQ ID NO: 87 (amidated PTH 1-58):
SVSEIQLMHNLGKHLNSMERVEWLRKKLQDVHNFVALGAPLAPRDAGSQRPRKK
EDNV; wherein the C-terminus is amidated SEQ ID NO: 88 (amidated PTH 1-57):
SVSEIQLMHNLGKHLNSMERVEWLRKKLQDVHNFVALGAPLAPRDAGSQRPRKK
EDN; wherein the C-terminus is amidated SEQ ID NO: 89 (amidated PTH 1-56):
SVSEIQLMHNLGKHLNSMERVEWLRKKLQDVHNFVALGAPLAPRDAGSQRPRKK
E; wherein the C-terminus is amidated SEQ ID NO: 90 (amidated PTH 1-55):
SVSEIQLMHNLGKHLNSMERVEWLRKKLQDVHNFVALGAPLAPRDAGSQRPRKK
E; wherein the C-terminus is amidated SEQ ID NO: 91 (amidated PTH 1-54):
SVSEIQLMHNLGKHLNSMERVEWLRKKLQDVHNFVALGAPLAPRDAGSQRPRKK;
wherein the C-terminus is amidated SEQ ID NO: 92 (amidated PTH 1-53):
SVSEIQLMHNLGKHLNSMERVEWLRKKLQDVHNFVALGAPLAPRDAGSQRPRK;
wherein the C-terminus is amidated SEQ ID NO: 93 (amidated PTH 1-52):
SVSEIQLMHNLGKHLNSMERVEWLRKKLQDVHNFVALGAPLAPRDAGSQRPR;
wherein the C-terminus is amidated SEQ ID NO: 94 (amidated PTH 1-51):
SVSEIQLMIHNLGKHLNSMERVEWLRKKLQDVHNFVALGAPLAPRDAGSQRP;
wherein the C-terminus is amidated SEQ ID NO: 95 (amidated PTH 1-50):
SVSEIQLMHNLGKHLNSMERVEWLRKKLQDVHNFVALGAPLAPRDAGSQR;
wherein the C-terminus is amidated SEQ ID NO: 96 (amidated PTH 1-49):
SVSEIQLMHNLGKHLNSMERVEWLRKKLQDVHNFVALGAPLAPRDAGSQ;
wherein the C-terminus is amidated SEQ ID NO: 97 (amidated PTH 1-48):
SVSEIQLMHNLGKHLNSMERVEWLRKKLQDVHNFVALGAPLAPRDAGS; wherein
the C-terminus is amidated -continued SEQ ID NO: 98 (amidated PTH 1-47):
SVSEIQLMHNLGKHLNSMERVEWLRKKLQDVHNFVALGAPLAPRDAG; wherein the C-terminus is amidated SEQ ID NO: 99 (amidated PTH 1-46):
SVSEIQLMHNLGKHLNSMERVEWLRKKLQDVHNFVALGAPLAPRDA; wherein the C-terminus is amidated SEQ ID NO: 100 (amidated PTH 1-45):
SVSEIQLMHNLGKHLNSMERVEWLRKKLQDVHNFVALGAPLAPRD; wherein the C-terminus is amidated SEQ ID NO: 101 (amidated PTH 1-44):
SVSEIQLMHNLGKHLNSMERVEWLRKKLQDVHNFVALGAPLAPR; wherein the C-terminus is amidated SEQ ID NO: 102 (amidated PTH 1-43):
SVSEIQLMHNLGKHLNSMERVEWLRKKLQDVHNFVALGAPLAP; wherein the C-terminus is amidated SEQ ID NO: 103 (amidated PTH 1-42):
SVSEIQLMHNLGKHLNSMERVEWLRKKLQDVHNFVALGAPLA; wherein the C-terminus is amidated SEQ ID NO: 104 (amidated PTH 1-41):
SVSEIQLMHNLGKHLNSMERVEWLRKKLQDVHNFVALGAPL; wherein the C-terminus is amidated SEQ ID NO: 105 (amidated PTH 1-40):
SVSEIQLMHNLGKHLNSMERVEWLRKKLQDVHNFVALGAP; wherein the C-terminus is amidated SEQ ID NO: 106 (amidated PTH 1-39):
SVSEIQLMHNLGKHLNSMERVEWLRKKLQDVHNFVALGA; wherein the C-terminus is amidated SEQ ID NO: 107 (amidated PTH 1-38):
SVSEIQLMIHNLGKHLNSMERVEWLRKKLQDVHNFVALG; wherein the C-terminus is amidated SEQ ID NO: 108 (amidated PTH 1-37):
SVSEIQLMHNLGKHLNSMERVEWLRKKLQDVHNFVAL; wherein the C-terminus is amidated SEQ ID NO: 109 (amidated PTH 1-36):
SVSEIQLMHNLGKHLNSMERVEWLRKKLQDVHNFVA; wherein the C-terminus is amidated SEQ ID NO: 110 (amidated PTH 1-35):
SVSEIQLMHNLGKHLNSMERVEWLRKKLQDVHNFV; wherein the C-terminus is amidated SEQ ID NO: 111 (amidated PTH 1-34):
SVSEIQLMHNLGKHLNSMERVEWLRKKLQDVHNF; wherein the C-terminus is amidated SEQ ID NO: 112 (amidated PTH 1-33):
SVSEIQLMHNLGKHLNSMERVEWLRKKLQDVHN; wherein the C-terminus is amidated SEQ ID NO: 113 (amidated PTH 1-32):
SVSEIQLMHNLGKHLNSMERVEWLRKKLQDVH; wherein the C-terminus is amidated SEQ ID NO: 114 (amidated PTH 1-31):
SVSEIQLMHNLGKHLNSMERVEWLRKKLQDV; wherein the C-terminus is amidated -continued SEQ ID NO: 115 (amidated PTH 1-30):
SVSEIQLMHNLGKHLNSMERVEWLRKKLQD; wherein the C-terminus is amidated SEQ ID NO: 116 (amidated PTH 1-29):
SVSEIQLMHNLGKHLNSMERVEWLRKKLQ; wherein the C-terminus is amidated SEQ ID NO: 117 (amidated PTH 1-28):
SVSEIQLMHNLGKHLNSMERVEWLRKKL; wherein the C-terminus is amidated SEQ ID NO: 118 (amidated PTH 1-27):
SVSEIQLMHNLGKHLNSMERVEWLRKK; wherein the C-terminus is amidated SEQ ID NO: 119 (amidated PTH 1-26):
SVSEIQLMHNLGKHLNSMERVEWLRK; wherein the C-terminus is amidated SEQ ID NO: 120 (amidated PTH 1-25):
SVSEIQLMHNLGKHLNSMERVEWLR; wherein the C-terminus is amidated SEQ ID NO: 121 (PTHrP):
AVSEHQLLHDKGKSIQDLRRRFFLHHLIAEIHTAEIRATSEVSPNSKPSPNTKNHPV

RFGSDDEGRYLTQETNKVETYKEQPLKTPGKKKKGKPGKRKEQEKKKRRTRSAW

LDSGVTGSGLEGDHLSDTSTTSLELDSRRH.

The term PTH polypeptide also encompasses all PTH and PTHrP polypeptides encoded by PTH and PTHrP analogs, orthologs, and/or species homologs. It is also recognized by one of ordinary skill in the art that PTHrP and PTHrP analogs bind to activate the common PTH/PTHrP1 receptor, so the term PTH polypeptide also encompasses all PTHrP analogs.

As used herein, the term "PTH analog" refers to PTH and PTHrP of different and unrelated organisms which perform the same functions in each organism, but which did not originate from an ancestral structure that the organisms' ancestors had in common. Instead, analogous PTH and PTHrP arose separately and then later evolved to perform the same or similar functions. In other words, analogous PTH and PTHrP polypeptides are polypeptides with quite different amino acid sequences, but that perform the same biological activity, namely raising serum calcium and renal phosphorus excretion, and lowering serum phosphorus and renal calcium excretion.

As used herein the term "PTH ortholog" refers to PTH and PTHrP within two different species which sequences are related to each other via a common homologous PTH or PTHrP in an ancestral species, but which have evolved to become different from each other.

As used herein, the term "PTH homolog" refers to PTH and PTHrP of different organisms which perform the same functions in each organism and which originate from an ancestral structure that the organisms' ancestors had in common. In other words, homologous PTH polypeptides are polypeptides with quite similar amino acid sequences that perform the same biological activity, namely raising serum calcium and renal phosphorus excretion, and lowering serum phosphorus and renal calcium excretion. In certain embodiments, PTH polypeptide homologs may be defined as polypeptides exhibiting at least 40%, 50%, 60%, 70%, 80%, 90% or 95% identity to a reference PTH or PTHrP polypeptide.

Thus, a PTH polypeptide may be, for example: (i) one in which at least one of the amino acids residues is substituted with a conserved or non-conserved amino acid residue, in certain embodiments a conserved amino acid residue, and such substituted amino acid residue may or may not be one encoded by the genetic code; and/or (ii) one in which at least one of the amino acid residues includes a substituent group; and/or (iii) one in which the PTH polypeptide is fused with another compound, such as a compound to increase the half-life of the polypeptide (for example, polyethylene glycol); and/or (iv) one in which additional amino acids are fused to the PTH polypeptide, such as an IgG Fc fusion region polypeptide or leader or secretory sequence or a sequence which is employed for purification of the above form of the polypeptide or a pre-protein sequence.

As used herein, the term "PTH polypeptide fragment" refers to any polypeptide comprising a contiguous span of a part of the amino acid sequence of a PTH or PTHrP polypeptide.

More specifically, a PTH polypeptide fragment comprises at least 6, such as at least 8, at least 10 or at least 17 consecutive amino acids of a PTH or PTHrP polypeptide. A PTH polypeptide fragment may additionally be described as sub-genuses of PTH or PTHrP polypeptides comprising at least 6 amino acids, wherein "at least 6" is defined as any integer between 6 and the integer representing the C-terminal amino acid of a PTH or PTHrP polypeptide. Further included are species of PTH or PTHrP polypeptide fragments at least 6 amino acids in length, as described above, that are further specified in terms of their N-terminal and C-terminal positions.

Also encompassed by the term "PTH polypeptide fragment" as individual species are all PTH or PTHrP polypeptide fragments, at least 6 amino acids in length, as described above, that may be particularly specified by a N-terminal and C-terminal position. That is, every combination of a N-terminal and C-terminal position that a fragment at least 6 contiguous amino acid residues in length could occupy, on any given amino acid sequence of a PTH or PTHrP polypeptide.

The term "PTH" also includes poly(amino acid) conjugates which have a sequence as described above, but having a backbone that comprises both amide and non-amide linkages, such as ester linkages, like for example depsipeptides. Depsipeptides are chains of amino acid residues in which the backbone comprises both amide (peptide) and ester bonds. Accordingly, the term "side chain" as used herein refers either to the moiety attached to the alpha-carbon of an amino acid moiety, if the amino acid moiety is connected through amine bonds such as in polypeptides, or to any carbon atom-comprising moiety attached to the backbone of a poly(amino acid) conjugate, such as for example in the case of depsipeptides.

In certain embodiments, the term "PTH" refers to polypeptides having a backbone formed through amide (peptide) bonds.

As the term PTH includes the above-described variants, analogs, orthologs, homologs, derivatives and fragments of PTH and PTHrP, all references to specific positions within a reference sequence also include the equivalent positions in variants, analogs, orthologs, homologs, derivatives and fragments of a PTH or PTHrP moiety, even if not specifically mentioned.

As used herein, the phrase "PTH conjugate, of which PTH moiety" followed by an amount in mg/ml means that the liquid formulation comprises PTH conjugate, but that for the corresponding amount only the PTH moiety is considered instead of taking the full PTH conjugate, i.e. moieties of the PTH conjugate other than the PTH moiety, such as the water-soluble carrier moiety, are not taken into account. The amount of PTH moiety within a PTH conjugate can be determined by quantitative amino acid analysis after total hydrolysis under acidic conditions of the PTH conjugate or by any known analytical methods that allows quantification of the unknown sample compared to the PTH conjugate of known PTH moiety content.

As used herein, the term "about" in combination with a numerical value is used to indicate a range ranging from and including the numerical value plus and minus no more than 10% of said numerical value, in certain embodiments, no more than 8% of said numerical value, in certain embodiments, no more than 5% of said numerical value and in certain embodiments, no more than 2% of said numerical value. For example, the phrase "about 200" is used to mean a range ranging from and including 200+/−10%, i.e. ranging from and including 180 to 220; in certain embodiments, 200+/−8%, i.e. ranging from and including 184 to 216; in certain embodiments, ranging from and including 200+/−5%, i.e. ranging from and including 190 to 210; and in certain embodiments 200+/−2%, i.e. ranging from and including 196 to 204. It is understood that a percentage given as "about 20%" does not mean "20%+/−10%", i.e. ranging from and including 10 to 30%, but "about 20%" means ranging from and including 18 to 22%, i.e. plus and minus 10% of the numerical value which is 20.

As used herein, the term "antimicrobial" refers to a chemical substance that kills or inhibits the growth of microorganisms, such as bacteria, fungi, yeasts, protozoans and/or destroys viruses.

As used herein, the term "anti-adsorption agents" refers to mainly ionic or non-ionic surfactants proteins or soluble polymers used to coat or adsorb competitively to the inner surface of the container comprising the formulation. Chosen concentration and type of excipient depends on the effect to be avoided but typically a monolayer of surfactant is formed at the interface just above the critical micelle concentration (CMC) value.

As used herein, the term "buffer" or "buffering agent" refers to a chemical compound that maintains the pH in a desired range. Physiologically tolerated buffers are, for example, sodium phosphate, succinate, histidine, bicarbonate, citrate and acetate, sulfate, nitrate, chloride, pyruvate. Antacids such as $Mg(OH)_2$ or $ZnCO_3$ may be also used.

As used herein, the term "$C_{1-4}$ alkyl" alone or in combination means a straight-chain or branched alkyl moiety having 1 to 4 carbon atoms. If present at the end of a molecule, examples of straight-chain or branched $C_{1-4}$ alkyl are methyl, ethyl, n-propyl, isopropyl, n-butyl, isobutyl, sec-butyl and tert-butyl. When two moieties of a molecule are linked by the $C_{1-4}$ alkyl, then examples for such $C_{1-4}$ alkyl groups are —$CH_2$—, —$CH_2$—$CH_2$—, —$CH(CH_3)$—, —$CH_2$—$CH_2$—$CH_2$—, —$CH(C_2H_5)$—, —$C(CH_3)_2$—. Each hydrogen of a $C_{1-4}$ alkyl carbon may optionally be replaced by a substituent as defined above. Optionally, a $C_{1-4}$ alkyl may be interrupted by one or more moieties as defined below.

As used herein, the term "$C_{1-6}$ alkyl" alone or in combination means a straight-chain or branched alkyl moiety having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —$CH_2$—, —$CH_2$—$CH_2$—, —$CH(CH_3)$—, —$CH_2$—$CH_2$—$CH_2$—, —$CH(C_2H_5)$— and —$C(CH_3)_2$—. Each hydrogen atom of a $C_{1-6}$ carbon may optionally be replaced by a substituent as defined above. Optionally, a $C_{1-6}$ alkyl may be interrupted by one or more moieties as defined below.

Accordingly, "$C_{1-10}$ alkyl", "$C_{1-20}$ alkyl" or "$C_{1-50}$ alkyl" means an alkyl chain having 1 to 10, 1 to 20 or 1 to 50 carbon atoms, respectively, wherein each hydrogen atom of the $C_{1-10}$, $C_{1-20}$ or $C_{1-50}$ carbon may optionally be replaced by a substituent as defined above. Optionally, a $C_{1-10}$, $C_{1-20}$ alkyl or $C_{1-50}$ alkyl may be interrupted by one or more moieties as defined below.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —CH=$CH_2$, —CH=CH—$CH_3$, —$CH_2$—CH=$CH_2$, —CH=CH$CH_2$—$CH_3$ and —CH=CH—CH=$CH_2$. When two moieties of a molecule are linked by the $C_{2-6}$ alkenyl group, then an example of such $C_{2-6}$ alkenyl is —CH=CH—. Each hydrogen atom of a $C_{2-6}$ alkenyl moiety may optionally be replaced by a substituent as defined above. Optionally, a $C_{2-6}$ alkenyl may be interrupted by one or more moieties as defined below.

Accordingly, the term "$C_{2-10}$ alkenyl", "$C_{2-20}$ alkenyl" or "$C_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a $C_{2-10}$ alkenyl, $C_{2-20}$ alkenyl or $C_{2-50}$ alkenyl group may optionally be replaced by a substituent as defined above. Optionally, a $C_{2-10}$ alkenyl, $C_{2-20}$ alkenyl or $C_{2-50}$ alkenyl may be interrupted by one or more moieties as defined below.

As used herein, the term "$C_{2-6}$ alkynyl" alone or in combination means a straight-chain or branched hydrocarbon moiety comprising at least one carbon-carbon triple bond having 2 to 6 carbon atoms. If present at the end of a molecule, examples are —C≡CH, —$CH_2$—C≡CH, $CH_2$—$CH_2$—C≡CH and $CH_2$—C≡C—$CH_3$. When two moieties of a molecule are linked by the alkynyl group, then an example is —C≡C—. Each hydrogen atom of a $C_{2-6}$ alkynyl group may optionally be replaced by a substituent as defined above. Optionally, one or more double bond(s) may occur. Optionally, a $C_{2-6}$ alkynyl may be interrupted by one or more moieties as defined below.

Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bond(s) may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-6}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkynyl or $C_{2-50}$ alkynyl may optionally be interrupted by one or more moieties which are in certain embodiments, selected from the group consisting of

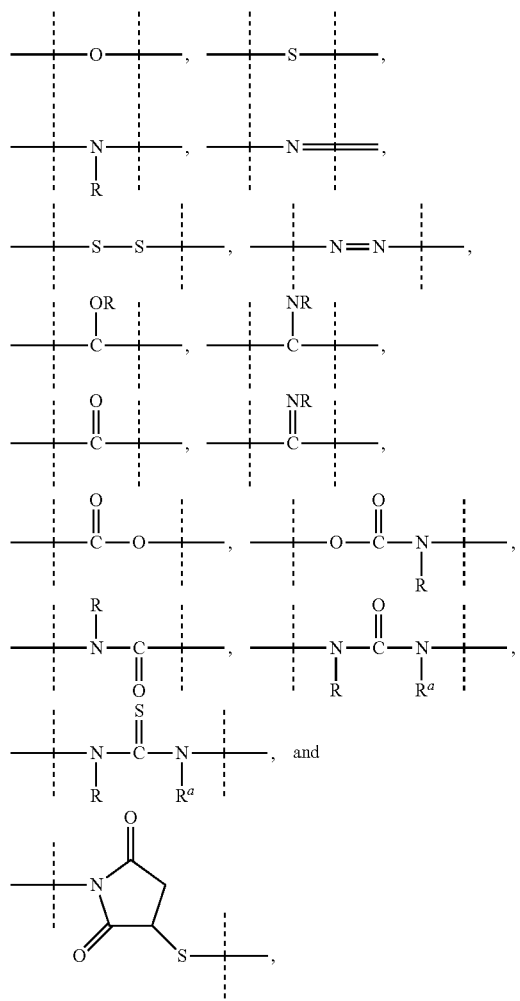

wherein
dashed lines indicate attachment to the remainder of the moiety or reagent; and —R and —$R^a$ are independently of each other selected from the group consisting of —H, methyl, ethyl, propyl, butyl, pentyl and hexyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norbornane or norbornene.

As used herein, the term "8- to 30-membered carbopolycyclyl" or "8- to 30-membered carbopolycycle" means a cyclic moiety of two or more rings with 8 to 30 ring atoms, where two neighboring rings share at least one ring atom and that may contain up to the maximum number of double bonds (aromatic or non-aromatic ring which is fully, partially or un-saturated). In certain embodiments, an 8- to 30-membered carbopolycyclyl means a cyclic moiety of two, three, four or five rings, in certain embodiments of two, three or four rings.

As used herein, the term "3- to 10-membered heterocyclyl" or "3- to 10-membered heterocycle" means a ring with 3, 4, 5, 6, 7, 8, 9 or 10 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent as defined below.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Similarly, the term "8- to 30-membered heteropolycyclyl" or "8- to 30-membered heteropolycycle" means a heterocyclic moiety of more than two rings with 8 to 30 ring atoms, in certain embodiments of three, four or five rings, where two neighboring rings share at least one ring atom and that may contain up to the maximum number of double bonds (aromatic or non-aromatic ring which is fully, partially or unsaturated), wherein at least one ring atom up to 10 ring atoms are replaced by a heteroatom selected from the group of sulfur (including S(O)—, —S(O)$_2$—), oxygen and nitrogen (including =N(O)—) and wherein the ring is linked to the rest of a molecule via a carbon or nitrogen atom.

It is understood that the phrase "the pair $R^x/R^y$ is joined together with the atom to which they are attached to form a $C_{3-10}$ cycloalkyl or a 3- to 10-membered heterocyclyl" in relation with a moiety of the structure

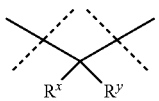

means that $R^x$ and $R^y$ form the following structure:

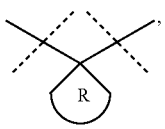

wherein R is $C_{3-10}$ cycloalkyl or 3- to 10-membered heterocyclyl.

It is also understood that the phrase "the pair $R^x/R^y$ is joint together with the atoms to which they are attached to form a ring A" in relation with a moiety of the structure

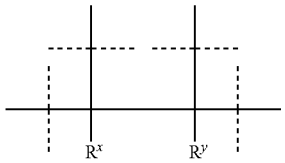

means that $R^x$ and $R^y$ form the following structure:

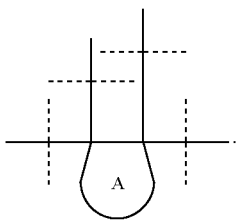

As used herein, the term "drug" as used herein refers to a substance used in the treatment, cure, prevention, or diagnosis of a disease or used to otherwise enhance physical or mental well-being. If a drug, such as PTH, is conjugated to another moiety, the moiety of the resulting product that originated from the PTH is referred to as "PTH moiety".

As used herein, the term "excipients" refers to compounds administered together with the therapeutic agent, for example, buffering agents, isotonicity modifiers, preservatives, stabilizers, anti-adsorption agents, oxidation protection agents, or other auxiliary agents. However, in some cases, one excipient may have dual or triple functions. The term "excipient" may also refer to a diluent, adjuvant, or vehicle with which the therapeutic, such as a drug or drug conjugate, is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical formulation is administered orally. Saline and aqueous dextrose are preferred excipients when the pharmaceutical formulation is administered intravenously. Saline solutions and aqueous dextrose and glycerol solutions are in certain embodiments, employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The liquid pharmaceutical formulation, if desired, can also contain minor amounts of wetting or emulsifying agents, pH buffering agents, like, for example, acetate, succinate, Tris (tris(hydroxymethyl)aminomethane), carbonate, phosphate, HEPES (4-(2-hydroxyethyl)-1-piperazineethanesulfonic acid), MES (2-(N-morpholino) ethanesulfonic acid), or can contain detergents, like Tween®, poloxamers, poloxamines, CHAPS, Igepal®, or amino acids like, for example, glycine, lysine, or histidine. These pharmaceutical formulations can take the form of solutions, suspensions, emulsions, tablets, pills, capsules, powders, sustained-release formulations and the like. The pharmaceutical formulation can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Such formulations will contain a therapeutically effective amount of the drug or drug moiety, together with a suitable amount of excipient so as to provide the form for proper administration to the patient. The formulation should suit the mode of administration.

As used herein, the term "formulation", "pharmaceutical formulation", "admixture" or "composition" refers to a formulation containing one or more active ingredients and one or more excipients, as well as any product which results, directly or indirectly, from combination, complexation or aggregation of any two or more of the ingredients of the formulation, or from dissociation of one or more of the ingredients, or from other types of reactions or interactions of one or more of the ingredients. Accordingly, the liquid pharmaceutical formulation of the present invention encompasses any formulation or composition made by admixing one or more PTH conjugates and a pharmaceutically acceptable excipient such as a buffering agent, an isotonicity agent, a preservative and optionally an antioxidant.

As used herein, the term "free form" of a drug refers to the drug in its unmodified, pharmacologically fully active form, e.g. after being released from the conjugate.

As used herein, the term "functional group" means a group of atoms which can react with other groups of atoms. Functional groups include, but are not limited, to the following groups: carboxylic acid (—(C=O)OH), primary or secondary amine (—NH$_2$, —NH—), maleimide, thiol (—SH), sulfonic acid (—(O=S=O)OH), carbonate, carbamate (—O(C=O)N<), hydroxyl (—OH), aldehyde (—(C=O)H), ketone (—(C=O)—), hydrazine (>N—N<), isocyanate, isothiocyanate, phosphoric acid (—O(P=O) OHOH), phosphonic acid (—O(P=O)OHH), haloacetyl, alkyl halide, acryloyl, aryl fluoride, hydroxylamine, disulfide, sulfonamides, sulfuric acid, vinyl sulfone, vinyl ketone, diazoalkane, oxirane and aziridine.

As used herein, the term "halogen" means fluoro, chloro, bromo or iodo. It is generally preferred that halogen is fluoro or chloro.

As used herein, the term "interrupted" means that a moiety is inserted in between two carbon atoms or—if the insertion is at one of the moiety's ends—between a carbon or heteroatom and a hydrogen atom, in certain embodiments between a carbon and a hydrogen atom.

As used herein, the term "immune checkpoint inhibitor (s)" refers to compounds that interfere with the function of or inhibit binding of ligands that induce signaling through cell-membrane expressed receptors that inhibit inflammatory immune cell function upon receptor activation. Such compounds may for example be biologics, such as antibodies, nanobodies, probodies, anticalins or cyclic peptides, or small molecule inhibitors.

As used herein, the term "isotonicity agent" refers to a chemical substance that minimizes pain, irritation and tissue damage that can result from cell damage due to osmotic pressure differences at the injection depot.

As used herein, the term "liquid pharmaceutical formulation" refers to a mixture comprising water-soluble PTH conjugate and one or more solvents, such as water.

As used herein, the term "dry pharmaceutical formulation" or "dried pharmaceutical formulation" means that a pharmaceutical formulation is provided in a dry form. Suitable methods for drying are spray-drying and lyophilization, i.e. freeze-drying. Such dry formulations comprising PTH conjugates have a residual water content of a maximum of 10%, in certain embodiments less than 5% and in certain embodiments, less than 2%, as determined with Karl Fischer. In certain embodiments, the dry pharmaceutical formulation is dried by lyophilization.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—" or "—X—", whereas each "—" indicates attachment to another moiety. Accordingly, a drug moiety, such as PTH moiety, is released from a conjugate as a drug such as PTH.

It is understood that if the sequence or chemical structure of a group of atoms is provided which group of atoms is attached to two moieties or is interrupting a moiety, said sequence or chemical structure can be attached to the two moieties in either orientation, unless explicitly stated otherwise. For example, a moiety "—C(O)N(R$^1$)—" can be attached to two moieties or interrupting a moiety either as "—C(O)N(R$^1$)—" or as "—N(R$^1$)C(O)—". Similarly, a moiety

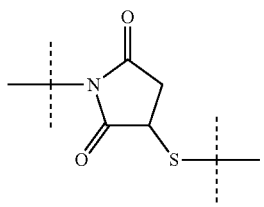

can be attached to two moieties or can interrupt a moiety either as

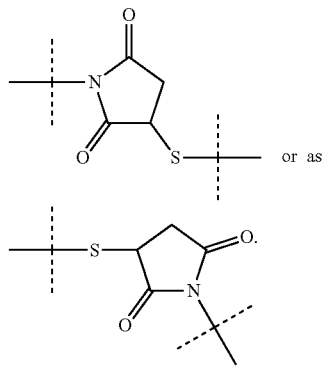

In case the PTH moiety comprises one or more acidic or basic groups, the liquid pharmaceutical formulation comprises also their corresponding pharmaceutically or toxicologically acceptable salts, in particular their pharmaceutically utilizable salts. Thus, the PTH moieties comprising one or more acidic groups can be present and used, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids, and other salts or amines known to the person skilled in the art. PTH moieties comprising one or more basic groups, i.e. groups which can be protonated, can be present and can be used in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. For the person skilled in the art further methods are known for converting the basic group into a cation like the alkylation of an amine group resulting in a positively-charged ammonium group and an appropriate counterion of the salt. If the PTH moieties simultaneously comprise acidic and basic groups, the pharmaceutical formulations according to the present invention also include, in addition to the salt forms mentioned, inner salts or betaines (zwitterions). The respective salts can be obtained by customary methods which are known to the person skilled in the art like, for example by contacting these conjugates with an organic or inorganic acid or base in a solvent or dispersant, or by anion exchange or cation exchange with other salts. The formulations according to the present invention also include all salts of the PTH conjugates which, owing to low physiological compatibility, are not directly suitable for use in pharmaceuticals but which can be used, for example, as intermediates for chemical reactions or for the preparation of pharmaceutically acceptable salts.

As used herein, the term "antioxidant" or "oxidation protection agent" refers to a compound which surpresses the oxidation of peptides.

As used herein, the term "pH-adjusting agent" refers to a chemical compound that is used to adjust the pH of a liquid solution or formulation.

The term "pharmaceutically acceptable" means a substance that does not cause harm when administered to a patient and preferably means approved by a regulatory agency, such as the EMA (Europe) and/or the FDA (US) and/or any other national regulatory agency for use in animals, preferably for use in humans.

As used herein, the term "physiological conditions" refers to an aqueous buffer at pH 7.4, 37° C.

The term "polypeptide" as used herein refers to a chain of at least 2 and up to and including 50 amino acid monomer moieties linked by peptide (amide) linkages. Only for PTH drugs and PTH moieties also the sequences having more than 50 amino acids will be referred to as "polypeptide" for simplification.

As used herein, the term "protein" refers to a chain of more than 50 amino acid monomer moieties linked by peptide linkages, in which preferably no more than 12000 amino acid monomers are linked by peptide linkages, such as no more than 10000 amino acid monomer moieties, no more than 8000 amino acid monomer moieties, no more than 5000 amino acid monomer moieties or no more than 2000 amino acid monomer moieties.

As used herein, the term "preservative" refers to a chemical compound that has both microbiostatic and microbiocidal properties, by killing microorganisms such as bacteria and preventing the growth of such microorganisms.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may also comprise one or more other chemical groups and/or moieties, such as, for example, one or more functional groups. In certain embodiments, a soluble polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. If the polymer is soluble, it has a molecular weight of at most 1000 kDa, such as at most 750 kDa, such as at most 500 kDa, such as at most 300 kDa, such as at most 200 kDa, such as at most 100 kDa.

It is understood that also a protein or a polypeptide is a polymer in which the amino acids are the repeating structural units, even though the side chains of each amino acid may be different.

As used herein, the term "polymeric" or "polymeric moiety" means a reagent or a moiety comprising one or more polymers or polymer moieties. A polymeric reagent or moiety may optionally also comprise one or more other moiety/moieties, which are in certain embodiments selected from the group consisting of:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

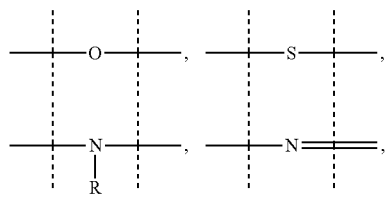

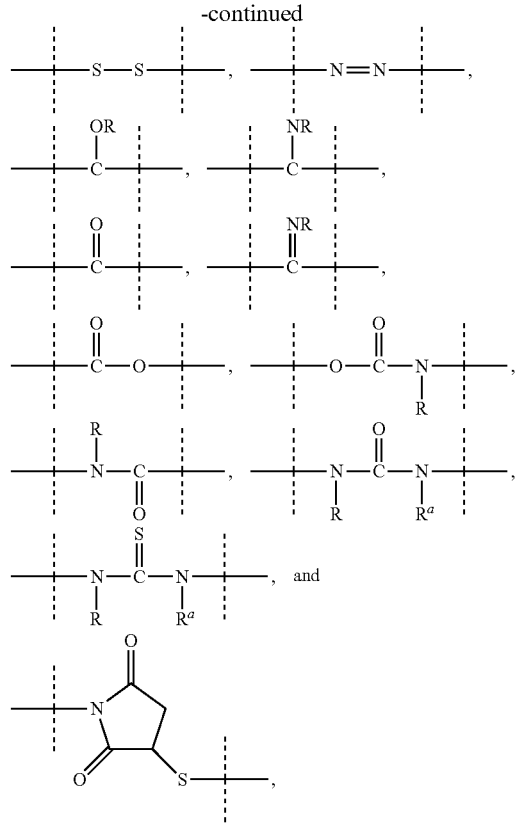

wherein
dashed lines indicate attachment to the remainder of the moiety or reagent, and —R and —$R^a$ are independently of each other selected from the group consisting of —H, methyl, ethyl, propyl, butyl, pentyl and hexyl.

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers, i.e. to the arithmetic mean of the molecular weight of the polymer or polymeric moiety and the arithmetic mean of the number of monomers of the polymer or polymeric moiety.

Accordingly, in a polymeric moiety comprising "x" monomer units any integer given for "x" therefore corresponds to the arithmetic mean number of monomers. Any range of integers given for "x" provides the range of integers in which the arithmetic mean numbers of monomers lies. An integer for "x" given as "about x" means that the arithmetic mean numbers of monomers lies in a range of integers of x+/−10%, in certain embodiments lies in a range of integers x+/−8%, in certain embodiments lies in a range of integers x+/−5% and in certain embodiments lies in a range of integers x+/−2%.

As used herein, the term "PEG-based" in relation to a moiety or reagent means that said moiety or reagent comprises PEG. In certain embodiments, a PEG-based moiety or reagent comprises at least 10% (w/w) PEG, such as at least 20% (w/w) PEG, such as at least 30% (w/w) PEG, such as at least 40% (w/w) PEG, such as at least 50% (w/w), such as at least 60% (w/w) PEG, such as at least 70% (w/w) PEG, such as at least 80% (w/w) PEG, such as at least 90% (w/w) PEG, such as at least 95% (w/w) PEG. The remaining weight percentage of the PEG-based moiety or reagent are other moieties selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

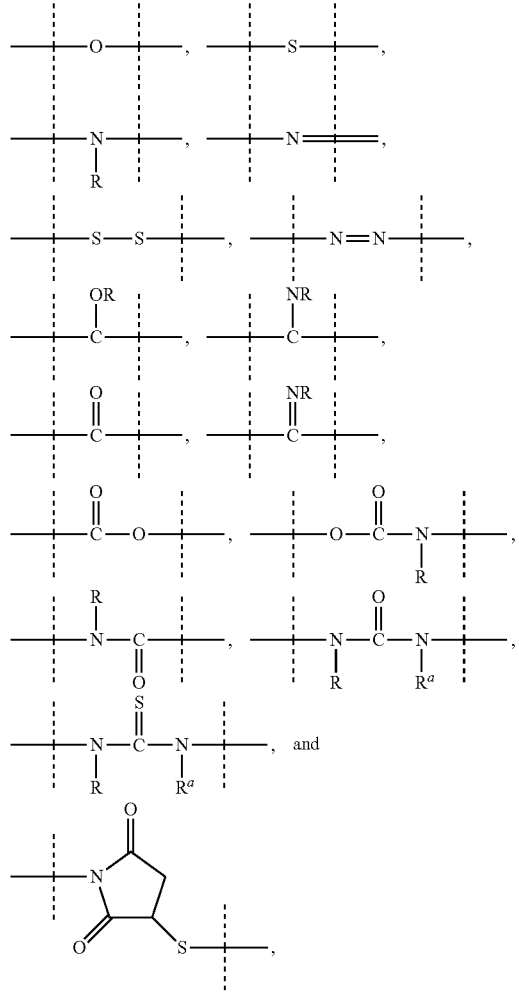

wherein
dashed lines indicate attachment to the remainder of the moiety or reagent, and —R and —$R^a$ are independently of each other selected from the group consisting of —H, methyl, ethyl, propyl, butyl, pentyl and hexyl.

As used herein, the term "PEG-based comprising at least X % PEG" in relation to a moiety or reagent means that said moiety or reagent comprises at least X % (w/w) ethylene glycol units (—$CH_2CH_2O$—), wherein the ethylene glycol units may be arranged blockwise, alternating or may be randomly distributed within the moiety or reagent and in certain embodiments, all ethylene glycol units of said moiety or reagent are present in one block; the remaining weight percentage of the PEG-based moiety or reagent are other moieties in certain embodiments selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

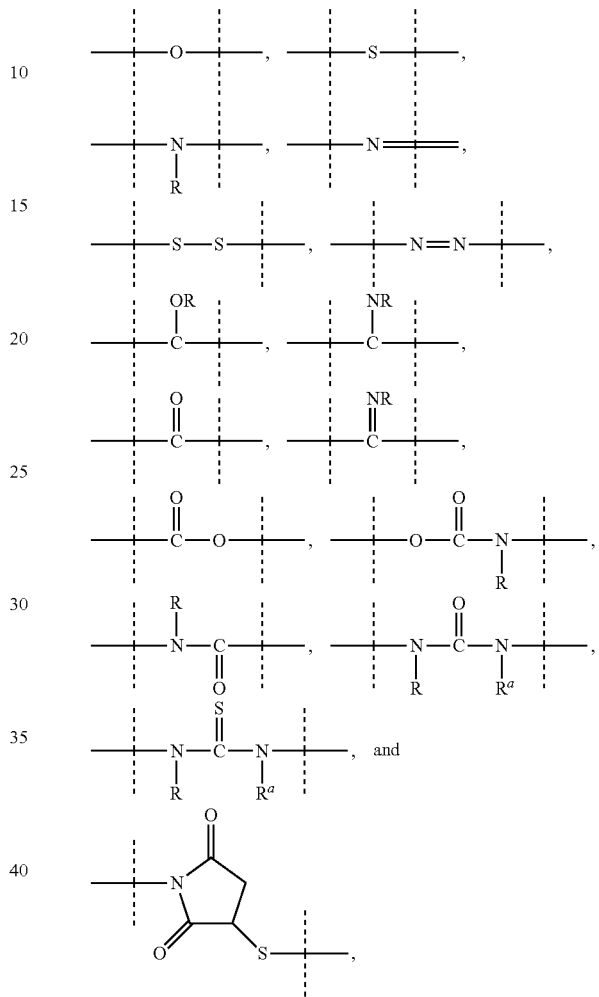

wherein
dashed lines indicate attachment to the remainder of the moiety or reagent, and —R and —$R^a$ are independently of each other selected from the group consisting of —H, methyl, ethyl, propyl, butyl, pentyl and hexyl.

As used herein, the term "hyaluronic acid-based comprising at least X % hyaluronic acid" is used accordingly.

It is also recognized by one of ordinary skill in the art that the conjugates of the present invention are prodrugs. As used herein, the term "prodrug" refers to a drug moiety, such as a PTH moiety, reversibly and covalently conjugated to a water-soluble carrier, such as —Z, through a reversible linker moiety. A prodrug releases the reversibly and covalently bound drug moiety in the form of its corresponding drug. In other words, a prodrug is a conjugate comprising a drug moiety, such as PTH moiety, which is covalently and reversibly conjugated to a water-soluble carrier via a reversible linker moiety, and wherein the conjugation of the carrier to the reversible linker moiety is either direct or through a spacer. Such prodrugs or conjugates release the formerly conjugated drug moiety in the form of a free drug.

As used herein, the term "random coil" refers to a peptide or protein adopting/having/forming, in certain embodiments having, a conformation which substantially lacks a defined secondary and tertiary structure as determined by circular dichroism spectroscopy performed in aqueous buffer at ambient temperature, and pH 7.4. In certain embodiments, the ambient temperature is about 20° C., i.e. between 18° C. and 22° C., while in certain embodiments the ambient temperature is 20° C.

As used herein, the term "reversible linkage" is a linkage that is cleavable, in the absence of enzymes under physiological conditions (aqueous buffer at pH 7.4, 37° C.) with a half-life ranging from one hour to six months, such as from one hour to four months, from one hour to three months, from one hour to two months, or from one hour to one month. Accordingly, a stable linkage is a linkage having a half-life under physiological conditions (aqueous buffer at pH 7.4, 37° C.) of more than six months.

As used herein, the term "reversible linker moiety" is a moiety which is covalently conjugated to a drug moiety, such as a PTH moiety, through a reversible linkage and is also covalently conjugated to a water-soluble carrier, such as —Z, wherein the covalent conjugation to said carrier is either direct or through a spacer moiety, such as -L$^2$-. In certain embodiments, the linkage between —Z and -L$^2$- is a stable linkage.

As used herein, the term "reagent" means a chemical compound which comprises at least one functional group for reaction with the functional group of another chemical compound or drug. It is understood that a drug comprising a functional group (such as a primary or secondary amine or hydroxyl functional group) is also a reagent.

As used herein, the term "spacer" or "spacer moiety" refers to a moiety suitable for connecting two moieties. Suitable spacers may be selected from the group consisting of $C_{1-50}$ alkyl, $C_{2-50}$ alkenyl or $C_{2-50}$ alkynyl, which moiety is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4- to 7-membered heterocyclyl, phenyl and naphthyl.

As used herein, the term "substituted" means that one or more —H atom(s) of a molecule or moiety are replaced by a different atom or a group of atoms, which are referred to as "substituent".

In certain embodiments, such one or more substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^1$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, $C_{1-50}$ alkyl, $C_{2-50}$ alkenyl, and $C_{2-50}$ alkynyl; wherein -T$^0$, $C_{1-50}$ alkyl, $C_{2-50}$ alkenyl, and $C_{2-50}$ alkynyl are optionally substituted with one or more —R$^{x2}$, which are the same or different and wherein $C_{1-50}$ alkyl, $C_{2-50}$ alkenyl, and $C_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—; —R$^{x1}$, —R$^{x1a}$, R$^{x1b}$ are independently of each other selected from the group consisting of —H, -T$^0$, $C_{1-50}$ alkyl, $C_{2-50}$ alkenyl, and $C_{2-50}$ alkynyl; wherein -T$^0$, $C_{1-50}$ alkyl, $C_{2-50}$ alkenyl, and $C_{2-50}$ alkynyl are optionally substituted with one or more —R$^{x2}$, which are the same or different and wherein $C_{1-50}$ alkyl, $C_{2-50}$ alkenyl, and $C_{2-50}$ alkynyl are optionally interrupted by one or more groups selected from the group consisting of -T$^0$, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each T$^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O) R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and $C_{1-6}$ alkyl; wherein $C_{1-6}$ alkyl is optionally substituted with one or more halogen, which are the same or different;

each —R$^{x3}$, —R$^{x3a}$, —R$^{x4}$, —R$^{x4a}$, —R$^{x4b}$ is independently selected from the group consisting of —H and $C_{1-6}$ alkyl; wherein $C_{1-6}$ alkyl is optionally substituted with one or more halogen, which are the same or different.

In certain embodiments, the one or more substituents are independently of each other selected from the group consisting of halogen, —CN, —COOR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), NO$_2$, —OC(O)R$^{x1}$, —N(R$^{x1}$)C(O) R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1a}$, C(O)N(R$^{x1a}$R$^{x1b}$), —OC(O)N(R$^{x1}$R$^{x1a}$), -T$^0$, $C_{1-10}$ alkyl, $C_{2-10}$ alkenyl, and $C_{2-10}$ alkynyl; wherein -T$^0$, $C_{1-10}$ alkyl, $C_{2-10}$ alkenyl, and $C_{2-10}$ alkynyl are optionally substituted with one or more —$^{x2}$, which are the same or different and wherein $C_{1-10}$ alkyl, $C_{2-10}$ alkenyl, and $C_{2-10}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each —R$^{x1}$, —R$^{x1a}$, —R$^{x1b}$, —R$^{x3}$, R$^{x3a}$ is independently selected from the group consisting of —H, halogen, $C_{1-6}$ alkyl, $C_{2-6}$ alkenyl, and $C_{2-6}$ alkynyl;

each T$^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O) R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and $C_{1-6}$ alkyl; wherein $C_{1-6}$ alkyl is optionally substituted with one or more halogen, which are the same or different;

each —$R^{x4}$, —$R^{x4a}$, —$R^{x4b}$ is independently selected from the group consisting of —H, halogen, $C_{1-6}$ alkyl, $C_{2-6}$ alkenyl, and $C_{2-6}$ alkynyl;

In certain embodiments, the one or more substituents are independently of each other selected from the group consisting of halogen, —CN, —COO$R^{x1}$, —O$R^{x1}$, —C(O)$R^{x1}$, —C(O)N($R^{x1}R^{x1a}$), —S(O)$_2$N($R^{x1}R^{x1a}$), —S(O)N($R^{x1}R^{x1a}$), —S(O)$_2R^{x1}$, —S(O)$R^{x1}$, —N($R^{x1}$)S(O)$_2$N($R^{x1a}R^{x1b}$), —S$R^{x1}$, —N($R^{x1}R^{x1a}$), NO$_2$, —OC(O)$R^{x1}$, —N($R^{x1}$)C(O)$R^{x1a}$, —N($R^{x1}$)S(O)$_2R^{x1a}$, —N($R^{x1}$)S(O)$R^{x1a}$, —N($R^{x1}$)C(O)O$R^{x1a}$, —N($R^{x1}$)C(O)N($R^{x1a}R^{x1b}$), —OC(O)N($R^{x1}R^{x1a}$), -T$^0$, $C_{1-6}$ alkyl, $C_{2-6}$ alkenyl, and $C_{2-6}$ alkynyl; wherein -T$^0$, $C_{1-6}$ alkyl, $C_{2-6}$ alkenyl, and $C_{2-6}$ alkynyl are optionally substituted with one or more —$R^{x2}$, which are the same or different and wherein $C_{1-6}$ alkyl, $C_{2-6}$ alkenyl, and $C_{2-6}$ alkynyl are optionally interrupted by one or more groups selected from the group consisting of -T$^0$, —C(O)O—, —O—, —C(O)—, —C(O)N($R^{x3}$)—, —S(O)$_2$N($R^{x3}$)—, —S(O)N($R^{x3}$)—, —S(O)$_2$—, —S(O)—, —N($R^{x3}$)S(O)$_2$N($R^{x3a}$)—, —S—, —N($R^{x3}$)—, —OC(O$R^{x3}$)($R^{x3a}$)—, —N($R^{x3}$)C(O)N($R^{x3a}$)—, and —OC(O)N($R^{x3}$)—; each —$R^{x1}$, —$R^{x1a}$, —$R^{x1b}$, —$R^{x2}$, —$R^{x3}$, —$R^{x3a}$ is independently selected from the group consisting of —H, halogen, $C_{1-6}$ alkyl, $C_{2-6}$ alkenyl, and $C_{2-6}$ alkynyl;

each T$^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T$^0$ is independently optionally substituted with one or more —$R^{x2}$, which are the same or different.

In certain embodiments, a maximum of 6 —H atoms of an optionally substituted molecule are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

As used herein, the term "stable" and "stability" with regards to a pharmaceutical formulation means that after a storage time, such as after one month, two months, four months, six months, eight months, twelve months, eighteen months, twenty-four months, thirty-six months, in particular after the indicated storage time, the pharmaceutical formulation comprises less than 5% of the drug in its free form and less than 20%, such as less than 10%, such as less than 5% of impurities, such as impurities resulted from the oxidation of methionine or tryptophan; isomerization of aspartic acid or aspartate; peptide bond cleavage at the aspartic acid, aspartate or asparagine; deamidation of asparagine or glutamine and aggregation of the peptide. Impurities may be quantified by RP-HPLC or SEC based on their respective peak area relative to the total peak area of all PTH conjugate-related peaks in the chromatograms and impurities in the PTH moiety of the PTH conjugate may be determined after releasing the PTH moiety from the PTH conjugate.

As used herein, the term "stabilizer" refers to compounds used to stabilize the drug conjugate. Stabilization may be achieved by strengthening of the peptide-stabilizing forces or by direct binding of excipients to the drug conjugate.

As used herein, the term "surfactant" refers to wetting agents that lower the surface tension of a liquid.

As used herein, the term "sealing a container" means that the container is closed in such way that it is airtight, allowing no gas exchange between the outside and the inside and keeping the content sterile.

As used herein, the term "therapeutically effective amount" means an amount sufficient to cure, alleviate or partially arrest the clinical manifestations of a given disease and its complications. Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician. Within the scope of this invention, therapeutically effective amount relates to dosages that aim to achieve therapeutic effect for an extended period of time, i.e. for at least one day, such as for two days, such as for three days, such as for four days, such as for five days, such as for six days, such as for one week or such as for two weeks.

As used herein, the term "traceless linker" means a reversible linker which upon cleavage releases the drug in its free form.

As used herein, the term "unit dose" means the amount of medication administered to a patient in a single dose.

As used herein, the term "water-soluble" with reference to a water-soluble carrier means that when such carrier is part of the PTH conjugate, at least 1 g of the PTH conjugate comprising such water-soluble carrier can be dissolved in one liter of water at 20° C. to form a homogeneous solution.

In general, the term "comprise" or "comprising" also encompasses "consist of" or "consisting of".

In certain embodiments the PTH moiety of the PTH conjugate has the sequence of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:107, SEQ ID NO:108, SEQ ID NO:109, SEQ ID NO:110, SEQ ID NO:111, SEQ ID NO:112, SEQ ID NO:113, SEQ ID NO:114 or SEQ ID NO:115. In certain embodiments, the PTH moiety has the sequence of SEQ ID NO:50, SEQ ID NO:51, SEQ ID NO:52, SEQ ID NO:110, SEQ ID NO:111 or SEQ ID NO:112. In certain embodiments, the PTH moiety has the sequence of SEQ ID NO:50. In certain embodiments, the PTH moiety has the sequence of SEQ ID NO:52. In certain embodiments, the PTH moiety has the sequence of SEQ ID NO:110. In certain embodiments, the PTH moiety has the sequence of SEQ ID NO:111. In certain embodiments, the PTH moiety has the sequence of SEQ ID NO:112. In certain embodiments, the PTH moiety has the sequence of SEQ ID NO:51.

In certain embodiments the water-soluble carrier moiety is defined as variable —Z, which is described in more detail elsewhere herein.

The liquid pharmaceutical formulation according to the present invention comprises a buffering agent. The buffering agent may be selected from the group consisting of succinic acid, citric acid, lactic acid, acetic acid, glutamic acid, fumaric acid, aspartic acid, glutaric acid, phosphoric acid, histidine, gluconic acid, tartaric acid, malic acid and mixtures thereof. It is clear to the person skilled in the art that the corresponding conjugate bases or salts of the buffering agents such as succinate, citrate, lactate, acetate, glutamate, fumarate, aspartate, glutarate, phosphate, gluconate, tartrate, malate and mixtures thereof are also included.

In certain embodiments, the buffering agent is succinic acid. In certain embodiments, the buffering agent is citric acid. In certain embodiments, the buffering agent is lactic acid. In certain embodiments, the buffering agent is acetic acid. In certain embodiments, the buffering agent is glutamic acid. In certain embodiments, the buffering agent is fumaric acid. In certain embodiments, the buffering agent is aspartic acid. In certain embodiments, the buffering agent is glutaric acid. In certain embodiments, the buffering agent is phosphoric acid. In certain embodiments, the buffering agent is histidine. In certain embodiments, the buffering agent is gluconic acid. In certain embodiments, the buffering agent is tartaric acid. In certain embodiments, the buffering agent is malic acid.

In certain embodiments, the buffering agent has a concentration ranging from 0.25 to 24 mg/ml. In certain embodiments, the buffering agent has a concentration ranging from 0.6 to 6.0 mg/ml. In certain embodiments, the buffering agent has a concentration ranging from 1.0 to 1.4 mg/ml. In certain embodiments, the buffering agent has a concentration of about 1.18 mg/ml.

In order to maintain a certain pH or pH range, the liquid pharmaceutical formulation comprises a buffering agent. The buffering agent maintains the pH of the liquid pharmaceutical formulation within a desired range. In certain embodiments, the pH of the liquid pharmaceutical formulation is not higher than 6, as under basic conditions the reversible linkage within the PTH-conjugate may not be stable.

In certain embodiments, the pH of the liquid pharmaceutical formulation is from about pH 3.0 to about pH 6.0. In certain embodiments, the pH of the liquid pharmaceutical formulation is from about pH 3.5 to about pH 5.0. In certain embodiments, the pH of the liquid pharmaceutical formulation is from about pH 3.7 to about pH 4.3. In certain embodiments, the pH of the liquid pharmaceutical formulation is 4.0.

The liquid pharmaceutical formulation according to the present invention comprises an isotonicity agent. The isotonicity agent may be selected from the group consisting of mannitol, trehalose, sucrose, raffinose, gelatin, lactose, dibasic calcium phosphate, sorbitol, xylitol, glycine, histidine, ethanol, hydroxyethylstarch, potassium chloride, sodium chloride, dextrose, dextran, Ficoll®, propylene glycol and mixtures thereof.

In certain embodiments, the isotonicity agent is selected from the group consisting of mannitol, trehalose, sucrose, raffinose, gelatin, lactose, dibasic calcium phosphate, sorbitol, xylitol, glycine, histidine, ethanol, hydroxyethylstarch, potassium chloride, sodium chloride, dextrose, dextran, propylene glycol and mixtures thereof.

In certain embodiments, the isotonicity agent is mannitol. In certain embodiments, the isotonicity agent is trehalose. In certain embodiments, the isotonicity agent is sucrose. In certain embodiments, the isotonicity agent is raffinose. In certain embodiments, the isotonicity agent is gelatin. In certain embodiments, the isotonicity agent is lactose. In certain embodiments, the isotonicity agent is dibasic calcium phosphate. In certain embodiments, the isotonicity agent is sorbitol. In certain embodiments, the isotonicity agent is xylitol. In certain embodiments, the isotonicity agent is glycine. In certain embodiments, the isotonicity agent is histidine. In certain embodiments, the isotonicity agent is ethanol. In certain embodiments, the isotonicity agent is hydroxyethylstarch. In certain embodiments, the isotonicity agent is potassium chloride. In certain embodiments, the isotonicity agent is sodium chloride. In certain embodiments, the isotonicity agent is dextrose. In certain embodiments, the isotonicity agent is dextran. In certain embodiments, the isotonicity agent is Ficoll®. In certain embodiments, the isotonicity agent is propylene glycol.

As defined herein, the term "trehalose" is intended to encompass all salts and hydration states of trehalose, such as trehalose anhydrous or trehalose dihydrate. In certain embodiments, the term "trehalose" refers to trehalose anhydrous. In certain embodiments, the term "trehalose" refers to trehalose dihydrate.

As defined herein, the term "mannitol" is intended to encompass both D-mannitol and L-mannitol, and mixtures thereof. In certain embodiments, the term "mannitol" refers to L-mannitol. In certain embodiments, the term "mannitol" refers to D-mannitol. In certain embodiments, the term "mannitol" refers to a mixture of L-mannitol and D-mannitol.

In certain embodiments, the isotonicity agent has a concentration ranging from 10 to 200 mg/ml. In certain embodiments, the isotonicity agent has a concentration ranging from 30 to 60 mg/ml. In certain embodiments, the isotonicity agent has a concentration ranging from 36 to 48 mg/ml. In certain embodiments, the isotonicity agent has a concentration of about 41.7 mg/ml.

The liquid pharmaceutical formulation according to the present invention comprises a preservative. The preservative may be selected from the group consisting of m-cresol, benzylalcohol, benzoic acid, phenol, methylparaben, ethylparaben, propylparaben, butylparaben, potassium sorbate, chlorobutanol, benzyl alcohol, phenylmercuric nitrate, thimerosal, sorbic acid, potassium sorbate, chlorocresol, benzalkonium chloride, 2-ethoxyethanol, chlorhexidine, chlorobutanol, phenylethyl alcohol, phenylmercuric acetate and mixtures thereof.

In certain embodiments, the preservative is m-cresol. In certain embodiments, the preservative is benzylalcohol. In certain embodiments, the preservative is benzoic acid. In certain embodiments, the preservative is phenol. In certain embodiments, the preservative is methylparaben. In certain embodiments, the preservative is ethylparaben. In certain embodiments, the preservative is propylparaben. In certain embodiments, the preservative is butylparaben. In certain embodiments, the preservative is potassium sorbate. In certain embodiments, the preservative is chlorocresol. In certain embodiments, the preservative is benzyl alcohol. In certain embodiments, the preservative is phenylmercuric nitrate. In certain embodiments, the preservative is thimerosal. In certain embodiments, the preservative is sorbic acid. In certain embodiments, the preservative is potassium sorbate. In certain embodiments, the preservative is chlorocresol. In certain embodiments, the preservative is benzalkonium chloride. In certain embodiments, the preservative is 2-ethoxyethanol. In certain embodiments, the preservative is chlorhexidine. In certain embodiments, the preservative is chlorbutanol. In certain embodiments, the preservative is phenylethyl alcohol. In certain embodiments, the preservative is phenylmercuric acetate.

In certain embodiments, the preservative has a concentration ranging from 1 to 10 mg/ml. In certain embodiments, the preservative has a concentration ranging from 1.5 to 3.5 mg/ml. In certain embodiments, the preservative has a concentration ranging from 2 to 3 mg/ml. In certain embodiments, the preservative has a concentration of about 2.5 mg/ml.

The liquid pharmaceutical formulation according to the present invention may further comprise a pH-adjusting agent. In certain embodiments, the pH-adjusting agent is an acid. Examples of acids may be selected from the group consisting of hydrochloric acid, phosphoric acid, carbonic acid, nitric acid and mixtures thereof.

In certain embodiments, the pH-adjusting agent is hydrochloric acid. In certain embodiments, the pH-adjusting agent is phosphoric acid. In certain embodiments, the pH-adjusting agent is carbonic acid. In certain embodiments, the pH-adjusting agent is nitric acid.

In certain embodiments, the pH-adjusting agent is a base. Examples of bases may be selected from the group consisting of Tris (tris(hydroxymethyl)aminomethane), potassium hydroxide, lysine, sodium hydroxide and mixtures thereof.

In certain embodiments, the pH-adjusting agent is Tris. In certain embodiments, the pH-adjusting agent is potassium hydroxide. In certain embodiments, the pH-adjusting agent is lysine. In certain embodiments, the pH-adjusting agent is sodium hydroxide.

In certain embodiment, the pH-adjusting agent is a mixture of at least one base and at least one acid. In certain embodiment, the pH-adjusting agent is a mixture of one base and one acid. In certain embodiment, the pH-adjusting agent is a mixture of sodium hydroxide and hydrochloric acid.

In certain embodiments, the pH-adjusting agent or mixture of pH-adjusting agents has a concentration ranging from 0.01 to 5 mg/ml. In certain embodiments, the pH-adjusting agent or mixture of pH-adjusting agents has a concentration ranging from 0.04 to 2.5 mg/ml. In certain embodiments, the pH-adjusting agent or mixture of pH-adjusting agents has a concentration ranging from 0.08 to 1.25 mg/ml. In certain embodiments, the pH-adjusting agent or mixture of pH-adjusting agents has a concentration of about 0.13 mg/ml. It is understood that in case of a mixture of pH-adjusting agents the provided concentrations refer to the total concentration of all pH-adjusting agents.

The liquid pharmaceutical formulation according to the present invention optionally comprises an antioxidant. Examples of antioxidants may be selected from the group consisting of methionine, butylhydroxytoluene, butylhydroxyanisol, tocopherol, propylgallate, ascorbic acid, sodium bisulfite, ethylenediaminetetraacetic acid (EDTA), cysteine, glutathione, monothioglycerol, poly(ethylenimine), vitamin E, ectoine, morin and mixtures thereof.

In certain embodiments, the antioxidant is methionine. In certain embodiments, the antioxidant is ascorbic acid. In certain embodiments, the antioxidant is butylhydroxytoluene. In certain embodiments, the antioxidant is butylhydroxyanisol. In certain embodiments, the antioxidant is tocopherol. In certain embodiments, the antioxidant is propylgallate. In certain embodiments, the antioxidant is sodium bisulfite. In certain embodiments, the antioxidant is monothioglycerol. In certain embodiments, the antioxidant is EDTA. In certain embodiments, the antioxidant is cysteine. In certain embodiments, the antioxidant is glutathione. In certain embodiments, the antioxidant is poly(ethylenimine). In certain embodiments, the antioxidant is vitamin E. In certain embodiments, the antioxidant is ectoine. In certain embodiments, the antioxidant is morin.

As defined herein, the term "methionine" is intended to encompass both D-methionine and L-methionine, and mixtures thereof. In certain embodiments, the term "methionine" refers to L-methionine. In certain embodiments, the term "methionine" refers to D-methionine. In certain embodiments, the term "methionine" refers to a mixture of D-methionine or L-methionine.

As defined herein, the term "EDTA" is intended to encompass all EDTA forms that are known in the art such as EDTA salts, including EDTA metal salts, such as EDTA disodium salt, EDTA dipotassium salt, EDTA calcium salt, EDTA dimagnesium salt or mixtures thereof. In certain embodiments, EDTA refers to EDTA disodium salt. In certain embodiments, the term "EDTA" refers to EDTA dicalcium salt. In certain embodiments, the term "EDTA" refers to EDTA anhydrous.

In certain embodiments, the molar ratio of antioxidant to PTH moiety is from about 0.1:1 to about 100:1. In certain embodiments, the molar ratio of antioxidant to PTH moiety is from about 0.1:1 to about 70:1. In certain embodiments, the molar ratio of antioxidant to PTH moiety is from about 0.1:1 to about 15:1. In certain embodiments, the molar ratio of antioxidant to PTH moiety is from about 1:1 to about 10:1. In certain embodiments, the molar ratio of antioxidant to PTH moiety is from about 3:1 to about 7:1.

In certain embodiments, the liquid pharmaceutical formulation of the present invention comprises no antioxidant.

The liquid pharmaceutical formulation of the present invention comprises a PTH conjugate.

In certain embodiments, the liquid pharmaceutical formulation comprises a PTH conjugate of which PTH moiety is present in a concentration of 0.05 to 5.0 mg/ml. In certain embodiments, the liquid pharmaceutical formulation comprises a PTH conjugate of which PTH moiety is present in a concentration of 0.1 to 5.0 mg/ml. In certain embodiments, the liquid pharmaceutical formulation comprises a PTH conjugate of which PTH moiety is present in a concentration of 0.1 to 1.5 mg/ml. In certain embodiments, the liquid pharmaceutical formulation comprises a PTH conjugate of which PTH moiety is present in a concentration of 0.25 to 0.35 mg/ml. In certain embodiments, the liquid pharmaceutical formulation comprises a PTH conjugate of which PTH moiety is present in a concentration of about 0.3 mg/ml. It is understood that the of the above provided concentrations refer to the amount of PTH moiety, but not to the whole PTH conjugate.

In certain embodiments, the PTH conjugate is of formula (Ia) or (Ib)

$$Z\text{-}(\text{-}L^2\text{-}L^1\text{-}D)_x \qquad (Ia)$$

$$D\text{-}(\text{-}L^1\text{-}L^2\text{-}Z)_y \qquad (Ib).$$

wherein
-D is a PTH moiety;
-$L^1$- is a reversible linker moiety connected to the PTH moiety -D through a functional group of PTH;
-$L^2$- is a single chemical bond or a spacer moiety;
—Z is a water-soluble carrier moiety;
x is an integer selected from the group consisting of 1, 2, 3, 4, 5, 6, 7, 8, 9, 10, 11, 12, 13, 14, 15 and 16; and
y is an integer selected from the group consisting of 1, 2, 3, 4 and 5.

In certain embodiments, -D is covalently and reversibly connected to -$L^1$-.

In certain embodiments, x of formula (Ia) is an integer selected from the group consisting of 1, 2, 3, 4, 6 and 8. In certain embodiments, x of formula (Ia) is an integer selected from the group consisting of 1, 2, 4, and 6. In certain embodiments, x of formula (Ia) is an integer selected from the group consisting of 1, 4 and 6. In certain embodiments, x of formula (Ia) is 1.

In certain embodiments, y of formula (Ib) is an integer selected from the group consisting of 2, 3, 4 and 5. In certain embodiments, y of formula (Ib) is an integer selected from the group consisting of 2, 3, and 4. In certain embodiments, y of formula (Ib) is an integer selected from the group consisting of 2 and 3.

In certain embodiments, y of formula (Ib) is an integer selected from the group consisting of 1, 2 and 3. In certain embodiments, y of formula (Ib) is 1. In certain embodiments, y of formula (Ib) is 2.

In certain embodiments, the PTH conjugate is of formula (Ia) with x=1.

In certain embodiments, -D has the sequence of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:107, SEQ ID NO:108, SEQ ID NO:109, SEQ ID NO:110, SEQ ID NO:111, SEQ ID NO:112, SEQ ID NO:113, SEQ ID NO:114 or SEQ ID NO:115.

In certain embodiments, -D has the sequence of SEQ ID NO:50, SEQ ID NO:51, SEQ ID NO:52, SEQ ID NO:110, SEQ ID NO:111 or SEQ ID NO:112.

In certain embodiments, -D has the sequence of SEQ ID NO:50. In certain embodiments, -D has the sequence of SEQ ID NO:52. In certain embodiments, -D has the sequence of SEQ ID NO:110. In certain embodiments, -D has the sequence of SEQ ID NO:111. In certain embodiments, -D has the sequence of SEQ ID NO:112. In certain embodiments, -D has the sequence of SEQ ID NO:51.

The moiety -$L^1$- is either conjugated to a functional group of the side chain of an amino acid residue of -D, to the N-terminal amine functional group or to the C-terminal carboxyl functional group of -D or to a nitrogen atom in the backbone polypeptide chain of -D. Attachment to either the N-terminus or C-terminus can either be directly through the corresponding amine or carboxyl functional group, respectively, or indirectly wherein a spacer moiety is first conjugated to the amine or carboxyl functional group to which spacer moiety -$L^1$- is conjugated.

In certain embodiments, the amino acid residue of PTH to which -$L^1$- is conjugated comprises a functional group selected from the group consisting of carboxylic acid, primary and secondary amine, maleimide, thiol, sulfonic acid, carbonate, carbamate, hydroxyl, aldehyde, ketone, hydrazine, isocyanate, isothiocyanate, phosphoric acid, phosphonic acid, haloacetyl, alkyl halide, acryloyl, aryl fluoride, hydroxylamine, sulfate, disulfide, vinyl sulfone, vinyl ketone, diazoalkane, oxirane, guanidine and aziridine. In certain embodiments, the amino acid residue of PTH to which -$L^1$- is conjugated comprises a functional group selected from the group consisting of hydroxyl, primary and secondary amine and guanidine. In certain embodiments, the amino acid residue of PTH to which -$L^1$- is conjugated comprises a primary or secondary amine functional group. In certain embodiments, the amino acid residue of PTH to which -$L^1$- is conjugated comprises a primary amine functional group.

If the moiety -$L^1$- is conjugated to a functional group of the side chain of an amino acid residue of PTH, said amino acid residue is selected from the group consisting of proteinogenic amino acid residues and non-proteinogenic amino acid residues.

In certain embodiments, -$L^1$- is conjugated to a functional group of the side chain of a non-proteinogenic amino acid residue of PTH. It is understood that such non-proteinogenic amino acid is not found in the sequence of native PTH or fragments thereof and that it may only be present in variants, analogs, orthologs, homologs and derivatives of PTH.

In certain embodiments, -$L^1$- is conjugated to a functional group of the side chain of a proteinogenic amino acid residue of PTH. In certain embodiments, said amino acid is selected from the group consisting of histidine, lysine, tryptophan, serine, threonine, tyrosine, aspartic acid, glutamic acid and arginine. In certain embodiments, said amino acid is selected from the group consisting of lysine, aspartic acid, arginine and serine. In certain embodiments, said amino acid is selected from the group consisting of lysine, arginine and serine.

In certain embodiments, -$L^1$- is conjugated to a functional group of the side chain of a histidine of PTH. In certain embodiments, -$L^1$- is conjugated to a functional group of the side chain of a lysine of PTH. In certain embodiments, -$L^1$- is conjugated to a functional group of the side chain of a tryptophan of PTH. In certain embodiments, -$L^1$- is conjugated to a functional group of the side chain of a serine of PTH. In certain embodiments, -$L^1$- is conjugated to a functional group of the side chain of a threonine of PTH. In certain embodiments, -$L^1$- is conjugated to a functional group of the side chain of a tyrosine of PTH. In certain embodiments, -$L^1$- is conjugated to a functional group of the side chain of an aspartic acid of PTH. In certain embodiments, -$L^1$- is conjugated to a functional group of the side chain of a glutamic acid of PTH. In certain embodiments, -$L^1$- is conjugated to a functional group of the side chain of an arginine of PTH.

It is understood that not every PTH moiety may comprise all of these amino acid residues.

In certain embodiments, -$L^1$- is conjugated to the N-terminal amine functional group of PTH, either directly through the corresponding amine functional group or indirectly wherein a spacer moiety is first conjugated to the amine functional group to which spacer moiety -$L^1$- is conjugated. In certain embodiments, -$L^1$- is directly conjugated to the N-terminal amine functional group of PTH, such as PTH 1-34, i.e. PTH having the sequence of SEQ ID NO:51. The N-terminal attachment of -$L^1$- is advantageous, i.e. attachment of -$L^1$- to the N-terminus of PTH, because it was found that such attachment site protects the N-terminus which is crucial for PTH activity. The main metabolite formed from a PTH conjugate with N-terminal attachment of -$L^1$- is PTH(1-33), i.e. the 33 N-terminal amino acids of PTH, which metabolite is known to be active.

In certain embodiments, -$L^1$- is conjugated to the C-terminal functional group of PTH, either directly through the corresponding carboxyl functional group or indirectly wherein a spacer moiety is first conjugated to the carboxyl functional group to which spacer moiety -$L^1$- is conjugated.

In certain embodiments, -$L^1$- is directly conjugated to the N-terminal amine functional group of PTH.

The moiety -$L^1$- can be connected to -D through any type of linkage, provided that it is reversible. In certain embodiments, -$L^1$- is connected to -D through a linkage selected from the group consisting of amide, ester, carbamate, acetal, aminal, imine, oxime, hydrazone, disulfide and acylguanidine. In certain embodiments, -$L^1$- is connected to -D through a linkage selected from the group consisting of amide, ester, carbamate and acylguanidine. It is understood that some of these linkages per se are not reversible, but that neighboring groups comprised in -$L^1$- render these linkages reversible.

In certain embodiments, -$L^1$- is connected to -D through an ester linkage. In certain embodiments, -$L^1$- is connected to -D through a carbamate linkage. In certain embodiments, is connected to -D through an acylguanidine. In certain embodiments, is connected to -D through an amide linkage.

The moiety is a reversible linker from which the drug, i.e. PTH, is released in its free form, meaning that is a traceless linker. Suitable reversible linkers are known in the art, such as for example the reversible linker moieties disclosed in WO 2005/099768 A2, WO 2006/136586 A2, WO 2011/089216 A1 and WO 2013/024053 A1, which are incorporated by reference herewith.

In certain embodiments, is a reversible linker as described in WO 2011/012722 A1, WO 2011/089214 A1, WO 2011/

089215 A1, WO 2013/024052 A1 and WO 2013/160340 A1, which are incorporated by reference herewith.

A moiety -L$^1$- is disclosed in WO 2009/095479 A2. Accordingly, in certain embodiments, the moiety is of formula (II):

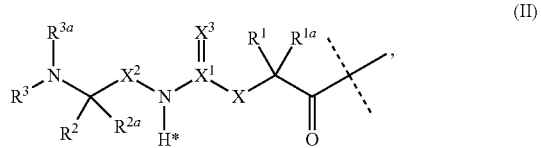

wherein the dashed line indicates the attachment to a nitrogen, hydroxyl or thiol of -D which is a PTH moiety;
—X— is —C(R$^4$R$^{4a}$)—; —N(R$^4$)—; —O—; —C(R$^4$R$^{4a}$)—C(R$^5$R$^{5a}$)—; —C(R$^5$R$^{5a}$)—C(R$^4$R$^{4a}$)—; —C(R$^4$R$^{4a}$)—N(R$^6$)—; —N(R$^6$)—C(R$^4$R$^{4a}$)—; —C(R$^4$R$^{4a}$)—O—; —O—C(R$^4$R$^{4a}$)—; or —C(R$^7$R$^{7a}$)—;
X$^1$ is C; S(O);
—X$^2$— is —C(R$^8$R$^{8a}$)—; or —C(R$^8$R$^{8a}$)—C(R$^9$R$^{9a}$)—;
=X$^3$ is =O; =S; or =N—CN;
—R$^1$, —R$^{1a}$, —R$^2$, —R$^{2a}$, —R$^4$, —R$^{4a}$, —R$^5$, —R$^{5a}$, —R$^6$, —R$^8$, —R$^{8a}$, —R$^9$, —R$^{9a}$ are independently selected from the group consisting of —H; and C$_{1-6}$ alkyl;
—R$^3$, —R$^{3a}$ are independently selected from the group consisting of —H and C$_{1-6}$ alkyl, provided that in case one of —R$^3$, —R$^{3a}$ or both are other than —H they are connected to the N to which they are attached through an sp$^3$-hybridized carbon atom;
—R$^7$ is —N(R$^{10}$R$^{10a}$) or —NR$^{10}$—(C=O)—R$^{11}$;
—R$^{7a}$, —R$^{10}$, —R$^{b10a}$, —R$^{11}$ are independently of each other —H or C$_{1-6}$ alkyl;
optionally, one or more of the pairs —R$^{1a}$/—R$^{4a}$, —R$^{1a}$/—$^{5a}$, —R$^{1a}$/—R$^{7a}$, —R$^{4a}$/—R$^{5a}$, —R$^{8a}$/—R$^{9a}$ form a chemical bond;
optionally, one or more of the pairs —R$^1$/—R$^{1a}$, —R$^2$/—R$^{2a}$, —R$^4$/—R$^{4a}$, —R$^5$/—R$^{5a}$, —R$^8$/—R$^{8a}$, —R$^9$/—R$^{9a}$ are joined together with the atom to which they are attached to form a C$_{3-10}$ cycloalkyl; or 3- to 10-membered heterocyclyl;
optionally, one or more of the pairs —R$^1$/—R$^4$, —R$^1$/—R$^5$, —R$^1$/—R$^6$, —R$^1$/—R$^{7a}$, —R$^4$/—R$^5$, —R$^4$/—R$^6$, —R$^8$/—R$^9$, —R$^2$/—R$^3$ are joined together with the atoms to which they are attached to form a ring A;
optionally, R$^3$/R$^{3a}$ are joined together with the nitrogen atom to which they are attached to form a 3- to 10-membered heterocycle;
A is selected from the group consisting of phenyl; naphthyl; indenyl; indanyl; tetralinyl; C$_{3-10}$ cycloalkyl; 3- to 10-membered heterocyclyl; and 8- to 11-membered heterobicyclyl; and
wherein -L$^1$- is substituted with -L$^2$-Z and wherein -L$^1$- is optionally further substituted, provided that the hydrogen marked with the asterisk in formula (II) is not replaced by -L$^2$-Z or a substituent;
wherein
-L$^2$- is a single chemical bond or a spacer; and
—Z is a water-soluble carrier.

In certain embodiments, -L$^1$- of formula (II) is substituted with one moiety -L$^2$-Z.

In certain embodiments, -L$^1$- of formula (II) is not further substituted.

It is understood that if —R$^3$/—R$^{3a}$ of formula (II) are joined together with the nitrogen atom to which they are attached to form a 3- to 10-membered heterocycle, only such 3- to 10-membered heterocycles may be formed in which the atoms directly attached to the nitrogen are sp$^3$-hybridized carbon atoms. In other words, such 3- to 10-membered heterocycle formed by —R$^3$/—R$^{3a}$ together with the nitrogen atom to which they are attached has the following structure:

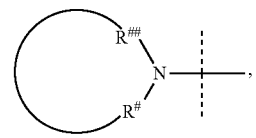

wherein
the dashed line indicates attachment to the rest of -L$^1$-;
the ring comprises 3 to 10 atoms comprising at least one nitrogen; and
R$^\#$ and R$^{\#\#}$ represent an sp$^3$-hydridized carbon atom.

It is also understood that the 3- to 10-membered heterocycle may be further substituted.

Exemplary embodiments of suitable 3- to 10-membered heterocycles formed by —R$^3$/—R$^{3a}$ of formula (II) together with the nitrogen atom to which they are attached are the following:

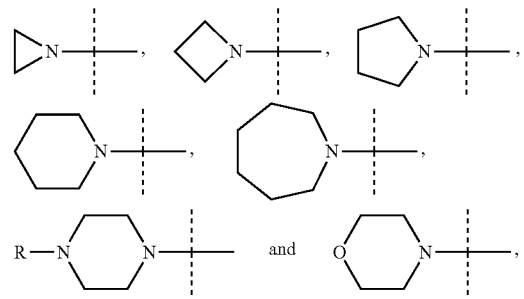

wherein
dashed lines indicate attachment to the rest of the molecule; and
—R is selected from the group consisting of —H and C$_{1-6}$ alkyl.

-L$^1$- of formula (II) may optionally be further substituted. In general, any substituent may be used as far as the cleavage principle is not affected, i.e. the hydrogen marked with the asterisk in formula (II) is not replaced and the nitrogen of the moiety

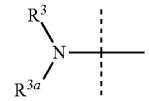

of formula (II) remains part of a primary, secondary or tertiary amine, i.e. —R$^3$ and —R$^{3a}$ are independently of each other —H or are connected to —N< through an sp$^3$-hybridized carbon atom.

In certain embodiments, —R¹ or —R¹ᵃ of formula (II) is substituted with -L²-Z. In certain embodiments, —R² or —R²ᵃ of formula (II) is substituted with -L²-Z. In certain embodiments, —R³ or —R³ᵃ of formula (II) is substituted with -L²-Z. In certain embodiments, —R⁴ of formula (II) is substituted with -L²-Z. In certain embodiments, —R⁵ or —R⁵ᵃ of formula (II) is substituted with -L²-Z. In certain embodiments, —R⁶ of formula (II) is substituted with -L²-Z. In certain embodiments, —R⁷ or —R⁷ᵃ of formula (II) is substituted with -L²-Z. In certain embodiments, —R⁸ or —R⁸ᵃ of formula (II) is substituted with -L²-Z. In certain embodiments, —R⁹ or —R⁹ᵃ of formula (II) is substituted with -L²-Z. In certain embodiments, —R¹⁰ of formula (II) is substituted with -L²-Z. In certain embodiments, —R¹¹ of formula (II) is substituted with -L²-Z.

In certain embodiments, —X— of formula (II) is selected from the group consisting of —C(R⁴R⁴ᵃ)—, —N(R⁴)— and —C(R⁷R⁷ᵃ)—.

In certain embodiments, —X— of formula (II) is —C(R⁴R⁴ᵃ)—.

In certain embodiments, —X— of formula (II) is —C(R⁷R⁷ᵃ)—.

In certain embodiments, —R⁷ of formula (II) is —NR¹⁰—(C=O)—R¹¹.

In certain embodiments, —R⁷ᵃ of formula (II) is selected from —H, methyl and ethyl. In certain embodiments, —R⁷ᵃ of formula (II) is —H.

In certain embodiments, —R¹⁰ of formula (II) is selected from —H, methyl and ethyl. In certain embodiments, —R¹⁰ of formula (II) is methyl.

In certain embodiments, —R¹¹ of formula (II) is selected from —H, methyl and ethyl. In certain embodiments, —R¹¹ of formula (II) is —H.

In certain embodiments, —R¹¹ of formula (II) is substituted with -L²-Z.

In certain embodiments, —X— of formula (II) is —N(R⁴)—.

In certain embodiments, —R⁴ of formula (II) is selected from the group consisting of —H, methyl and ethyl.

In certain embodiments, —R⁴ of formula (II) is —H.

In certain embodiments, X¹ of formula (II) is C.

In certain embodiments, =X³ of formula (II) is =O. In certain embodiments, —X²— of formula (II) is —C(R⁸R⁸ᵃ)—.

In certain embodiments, —R⁸ and —R⁸ᵃ of formula (II) are independently selected from the group consisting of —H, methyl and ethyl. In certain embodiments, at least one of —R⁸ and —R⁸ᵃ of formula (II) is —H. In certain embodiments, both —R⁸ and —R⁸ᵃ of formula (II) are —H.

In certain embodiments, —R¹ and —R¹ᵃ of formula (II) are independently selected from the group consisting of —H, methyl and ethyl.

In certain embodiments, at least one of —R¹ and —R¹ᵃ of formula (II) is —H.

In certain embodiments, both —R¹ and —R¹ᵃ of formula (II) are —H.

In certain embodiments, at least one of —R¹ and —R¹ᵃ of formula (II) is methyl.

In certain embodiments, both —R¹ and —R¹ᵃ of formula (II) are methyl.

In certain embodiments, —R² and —R²ᵃ of formula (II) are independently selected from the group consisting of —H, methyl and ethyl. In certain embodiments, at least one of —R² and —R²ᵃ of formula (II) is —H. In certain embodiments, both —R² and —R²ᵃ of formula (II) are H.

In certain embodiments, —R³ and —R³ᵃ of formula (II) are independently selected from the group consisting of —H, methyl, ethyl, propyl and butyl.

In certain embodiments, at least one of —R³ and —R³ᵃ of formula (II) is methyl.

In certain embodiments, —R³ of formula (II) is methyl and —R³ᵃ of formula (II) is —H.

In certain embodiments, —R³ and —R³ᵃ of formula (II) are both —H.

In certain embodiments, -D is connected to -L¹- through a nitrogen by forming an amide bond.

In certain embodiments, the moiety -L¹- is of formula (IIa-i):

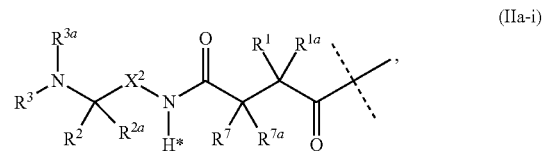

wherein
the dashed line indicates the attachment to a nitrogen of -D which is a PTH moiety by forming an amide bond; —R¹, —R¹ᵃ, —R², —R²ᵃ, —R³, —R³ᵃ, —R⁷, —R⁷ᵃ and —X²— are used as defined in formula (II); and wherein -L¹- is substituted with -L²-Z and wherein -L¹- is optionally further substituted, provided that the hydrogen marked with the asterisk in formula (IIa-i) is not replaced by -L²-Z or a substituent.

In certain embodiments, -L¹- of formula (IIa-i) is substituted with one moiety -L²-Z.

In certain embodiments, the moiety -L¹- of formula (IIa-i) is not further substituted.

In certain embodiments, —R¹ and —R¹ᵃ of formula (IIa-i) are independently selected from the group consisting of —H, methyl and ethyl. In certain embodiments, at least one of —R¹ and —R¹ᵃ of formula (IIa-i) is —H. In certain embodiments, both —R¹ and —R¹ᵃ of formula (II-i) are —H. In certain embodiments, —R⁷ of formula (IIa-i) is —NR¹⁰—(C=O)—R¹¹.

In certain embodiments, —R⁷ᵃ of formula (IIa-i) is selected from —H, methyl and ethyl. In certain embodiments, —R⁷ᵃ of formula (IIa-i) is —H.

In certain embodiments, —R¹⁰ of formula (IIa-i) is selected from —H, methyl and ethyl. In certain embodiments, —R¹⁰ of formula (IIa-i) is methyl.

In certain embodiments, —R¹¹ of formula (IIa-i) is selected from —H, methyl and ethyl. In certain embodiments, —R¹¹ of formula (IIa-i) is —H.

In certain embodiments, —R¹¹ f formula (IIa-i) is substituted with -L²-Z.

In certain embodiments, —X²— of formula (IIa-i) is —C(R⁸R⁸ᵃ)—. In certain embodiments, —R⁸ and —R⁸ᵃ of formula (IIa-i) are independently selected from the group consisting of —H, methyl and ethyl. In certain embodiments, at least one of —R⁸ or —R⁸ᵃ of formula (IIa-i) is —H. In certain embodiments, both —R⁸ and —R⁸ᵃ of formula (IIa-i) are —H.

In certain embodiments, —R² and —R²ᵃ of formula (IIa-i) are independently selected from the group consisting of —H, methyl and ethyl. In certain embodiments, at least one of —R² or —R²ᵃ of formula (IIa-i) is —H. In certain embodiments, both —R² and —R²ᵃ of formula (IIa-i) are H.

In certain embodiments, —R³ and —R³ᵃ of formula (IIa-i) are independently selected from the group consisting of —H, methyl, ethyl, propyl and butyl. In certain embodiments, at least one of —R³ or —R³ᵃ of formula (IIa-i) is methyl.

In certain embodiments, —R³ of formula (IIa-i) is —H and —R³ᵃ of formula (IIa-i) is methyl.

In certain embodiments, the moiety -L¹- is of formula (II-ii):

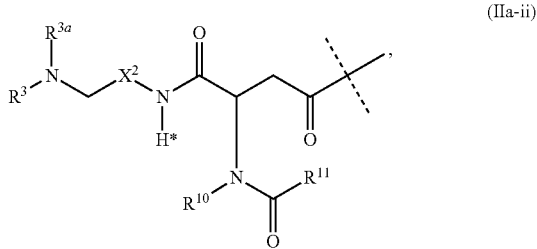

wherein the dashed line indicates the attachment to a nitrogen of -D which is a PTH moiety by forming an amide bond;
—R³, —R³ᵃ, —R¹, —R¹¹ and —X²— are used as defined in formula (II); and wherein -L¹- is substituted with -L²-Z and wherein -L¹- is optionally further substituted, provided that the hydrogen marked with the asterisk in formula (IIa-ii) is not replaced by -L²-Z or a substituent.

In certain embodiments, -L¹- of formula (II-ii) is substituted with one moiety -L²-Z.

In certain embodiments, the moiety -L¹- of formula (II-ii) is not further substituted.

In certain embodiments, —X²— of formula (II-ii) is —C(R⁸R⁸ᵃ)—.

In certain embodiments, —R⁸ and —R⁸ᵃ of formula (II-ii) are independently selected from the group consisting of —H, methyl and ethyl. In certain embodiments, at least one of —R⁸ or —R⁸ᵃ of formula (II-ii) is —H. In certain embodiments, both —R⁸ and —R⁸ᵃ of formula (II-ii) are —H.

In certain embodiments, —R³ and —R³ᵃ of formula (II-ii) are independently selected from the group consisting of —H, methyl, ethyl, propyl and butyl. In certain embodiments, at least one of —R³ or —R³ᵃ of formula (II-ii) is methyl.

In certain embodiments, —R³ of formula (II-ii) is —H and —R³ᵃ of formula (II-ii) is methyl.

In certain embodiments, —R¹⁰ of formula (II-ii) is selected from —H, methyl and ethyl. In certain embodiments, —R¹⁰ of formula (II-ii) is methyl.

In certain embodiments, —R¹¹ of formula (II-ii) is selected from —H, methyl and ethyl. In certain embodiments, —R¹¹ of formula (II-ii) is —H.

In certain embodiments, —R¹¹ of formula (II-ii) is substituted with -L²-Z.

In certain embodiments, the moiety -L¹- is of formula (II-ii'):

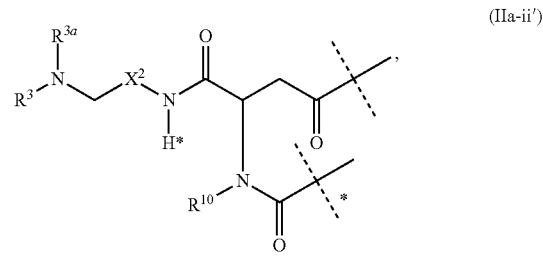

wherein
wherein the dashed line indicates the attachment to a nitrogen of -D which is a PTH moiety by forming an amide bond;
the dashed line marked with the asterisk indicates attachment to -L²-;
—R³, —R³ᵃ, —R¹⁰ and —X²— are used as defined in formula (II); and
wherein -L¹- is optionally further substituted, provided that the hydrogen marked with the asterisk in formula (IIa-ii') is not replaced by a substituent.

In certain embodiments, the moiety -L¹- of formula (IIa-ii') is not further substituted.

In certain embodiments, —X²— of formula (IIa-ii') is —C(R⁸R⁸ᵃ)—.

In certain embodiments, —R⁸ and —R⁸ᵃ of formula (IIa-ii') are independently selected from the group consisting of —H, methyl and ethyl. In certain embodiments, at least one of —R⁸ or —R⁸ᵃ of formula (IIa-ii') is —H. In certain embodiments, both —R⁸ and —R⁸ᵃ of formula (IIa-ii') are —H.

In certain embodiments, —R³ and —R³ᵃ of formula (IIa-ii') are independently selected from the group consisting of —H, methyl, ethyl, propyl and butyl. In certain embodiments, at least one of —R³ and —R³ᵃ of formula (IIa-ii') is methyl.

In certain embodiments, —R³ of formula (IIa-ii') is —H and —R³ᵃ of formula (IIa-ii') is methyl. In certain embodiments, —R¹⁰ of formula (IIa-ii') is selected from —H, methyl and ethyl. In certain embodiments, —R¹⁰ of formula (IIa-ii') is methyl.

In certain embodiments, the moiety -L¹- is of formula (IIa-iii):

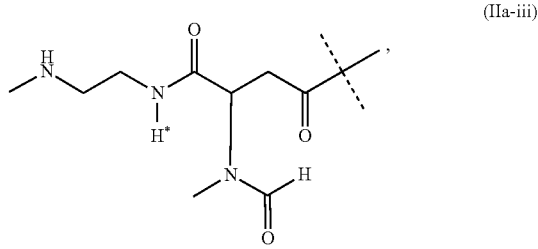

wherein the dashed line indicates the attachment to a nitrogen of -D which is a PTH moiety by forming an amide bond; and
wherein -L¹- is substituted with -L²-Z and wherein -L¹- is optionally further substituted, provided that the hydrogen marked with the asterisk in formula (II-iii) is not replaced by -L²-Z or -L²-Z' or a substituent.

In certain embodiments, -L¹- of formula (II-iii) is substituted with one moiety -L²-Z.

In certain embodiments, the moiety -L$^1$- of formula (II-iii) is not further substituted.

In certain embodiments, the moiety -L$^1$- is of formula (IIa-iii'):

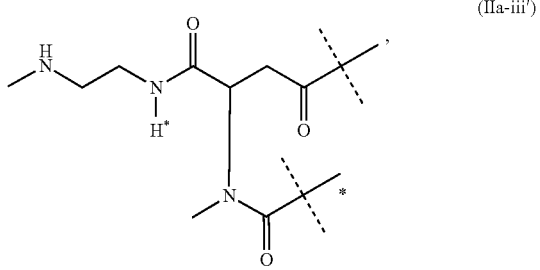

(IIa-iii')

wherein wherein the dashed line indicates the attachment to a nitrogen of -D which is a PTH moiety by forming an amide bond;

the dashed line marked with the asterisk indicates attachment to -L$^2$-; and wherein -L$^1$- is optionally further substituted, provided that the hydrogen marked with the asterisk in formula (IIa-iii') is not replaced by a substituent.

In certain embodiments, the moiety -L$^1$- of formula (IIa-iii') is not further substituted.

In certain embodiments, the moiety -L$^1$- is of formula (IIb-i):

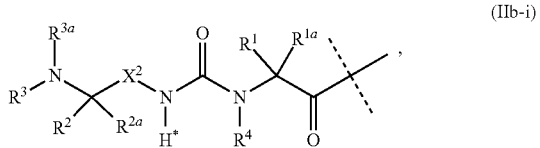

(IIb-i)

wherein the dashed line indicates the attachment to a nitrogen of -D which is a PTH moiety by forming an amide bond;

—R$^1$, —R$^{1a}$, —R$^2$, —R$^{2a}$, —R$^3$, —R$^{3a}$, —R$^4$ and —X$^2$— are used as defined in formula (II); and wherein -L$^1$- is substituted with -L$^2$-Z and wherein -L$^1$- is optionally further substituted, provided that the hydrogen marked with the asterisk in formula (IIb-i) is not replaced by -L$^2$-Z or a substituent.

In certain embodiments, -L$^1$- of formula (IIb-i) is substituted with one moiety -L$^2$-Z.

In certain embodiments, the moiety -L$^1$- of formula (IIb-i) is not further substituted.

In certain embodiments, —R$^1$ and —R$^{1a}$ of formula (IIb-i) are independently selected from the group consisting of —H, methyl and ethyl. In certain embodiments, at least one of —R$^1$ or —R$^{1a}$ of formula (IIb-i) is methyl. In certain embodiments, both —R$^1$ and —R$^{1a}$ of formula (IIb-i) are methyl.

In certain embodiments, —R$^4$ of formula (IIb-i) is selected from the group consisting of —H, methyl and ethyl. In certain embodiments, —R$^4$ of formula (IIb-i) is —H.

In certain embodiments, —X$^2$— of formula (IIb-i) is —C(R$^8$R$^{8a}$)—.

In certain embodiments, —R$^8$ and —R$^{8a}$ of formula (IIb-i) are independently selected from the group consisting of —H, methyl and ethyl. In certain embodiments, at least one of —R$^8$ and —R$^{8a}$ of formula (IIb-i) is —H. In certain embodiments, both —R$^8$ and —R$^{8a}$ of formula (IIb-i) are —H.

In certain embodiments, —R$^2$ and —R$^{2a}$ of formula (IIb-i) are independently selected from the group consisting of —H, methyl and ethyl. In certain embodiments, at least one of —R$^2$ or —R$^{2a}$ of formula (IIb-i) is —H. In certain embodiments, both —R$^2$ and —R$^{2a}$ of formula (IIb-i) are H.

In certain embodiments, —R$^3$ and —R$^{3a}$ of formula (IIb-i) are independently selected from the group consisting of —H, methyl, ethyl, propyl and butyl. In certain embodiments, at least one of —R$^3$ or —R$^{3a}$ of formula (IIb-i) is —H. In certain embodiments, both —R$^3$ and —R$^{3a}$ of formula (IIb-i) are —H.

In certain embodiments, the moiety -L$^1$- is of formula (IIb-ii):

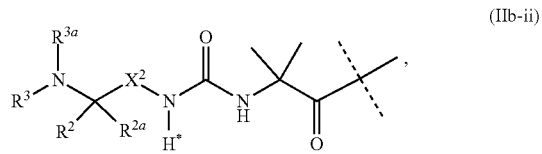

(IIb-ii)

wherein the dashed line indicates the attachment to a nitrogen of -D which is a PTH moiety by forming an amide bond;

—R$^2$, —R$^{2a}$, —R$^3$, —R$^{3a}$ and —X$^2$— are used as defined in formula (II); and wherein -L$^1$- is substituted with -L$^2$-Z and wherein -L$^1$- is optionally further substituted, provided that the hydrogen marked with the asterisk in formula (IIb-ii) is not replaced by -L$^2$-Z or a substituent.

In certain embodiments, -L$^1$- of formula (IIb-ii) is substituted with one moiety -L$^2$-Z.

In certain embodiments, the moiety -L$^1$- of formula (IIb-ii) is not further substituted.

In certain embodiments, —X$^2$— of formula (IIb-ii) is —C(R$^8$R$^{8a}$)—.

In certain embodiments, —R$^8$ and —R$^{8a}$ of formula (IIb-ii) are independently selected from the group consisting of —H, methyl and ethyl. In certain embodiments, at least one of —R$^8$ or —R$^{8a}$ of formula (IIb-ii) is —H. In certain embodiments, both —R$^8$ and —R$^{8a}$ of formula (IIb-ii) are —H. In certain embodiments, —R$^2$ and —R$^{2a}$ of formula (IIb-ii) are independently selected from the group consisting of —H, methyl and ethyl. In certain embodiments, at least one of —R$^2$ or —R$^{2a}$ of formula (IIb-ii) is —H. In certain embodiments, both —R$^2$ and of formula (IIb-ii) are H.

In certain embodiments, —R$^3$ and —R$^{3a}$ of formula (IIb-ii) are independently selected from the group consisting of —H, methyl, ethyl, propyl and butyl. In certain embodiments, at least one of —R$^3$ or —R$^{3a}$ of formula (IIb-ii) is —H. In certain embodiments, both —R$^3$ and —R$^{3a}$ of formula (IIb-ii) are —H.

In certain embodiments, the moiety -L$^1$- is of formula (IIb-ii'):

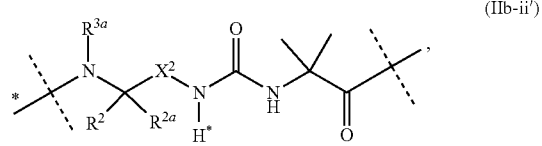

(IIb-ii')

wherein
the dashed line indicates the attachment to a nitrogen of -D which is a PTH moiety by forming an amide bond;
the dashed line marked with the asterisk indicates attachment to -$L^2$-;
—$R^2$, —$R^{2a}$, —$R^{3a}$ and —$X^2$— are used as defined in formula (II); and
wherein -$L^1$- is substituted with -$L^2$-Z and wherein -$L^1$- is optionally further substituted, provided that the hydrogen marked with the asterisk in formula (IIb-ii') is not replaced by -$L^2$-Z or a substituent.

In certain embodiments, the moiety -$L^1$- of formula (IIb-ii') is not further substituted.

In certain embodiments, —$X^2$— of formula (IIb-ii') is —$C(R^8R^{8a})$—.

In certain embodiments, —$R^8$ and —$R^{8a}$ of formula (IIb-ii') are independently selected from the group consisting of —H, methyl and ethyl. In certain embodiments, at least one of —$R^8$ or —$R^{8a}$ of formula (IIb-ii') is —H. In certain embodiments, both —$R^8$ and —$R^{8a}$ of formula (IIb-ii') are —H.

In certain embodiments, —$R^2$ and —$R^{2a}$ of formula (IIb-ii') are independently selected from the group consisting of —H, methyl and ethyl. In certain embodiments, at least one of —$R^2$ or —$R^{2a}$ of formula (IIb-ii') is —H. In certain embodiments, both —$R^2$ and —$R^{2a}$ of formula (IIb-ii') are H.

In certain embodiments, —$R^{3a}$ of formula (IIb-ii') is independently selected from the group consisting of —H, methyl, ethyl, propyl and butyl. In certain embodiments, —$R^{3a}$ of formula (IIb-ii') is —H.

In certain embodiments, the moiety -$L^1$- is of formula (IIb-iii):

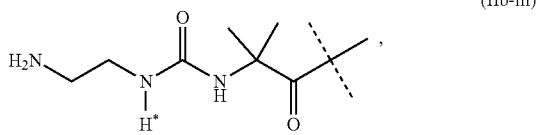
(IIb-iii)

wherein
the dashed line indicates the attachment to a nitrogen of -D which is a PTH moiety by forming an amide bond; and
wherein -$L^1$- is substituted with -$L^2$-Z and wherein -$L^1$- is optionally further substituted, provided that the hydrogen marked with the asterisk in formula (IIb-iii) is not replaced by -$L^2$-Z or a substituent.

In certain embodiments, -$L^1$- of formula (IIb-iii) is substituted with one moiety -$L^2$-Z.

In certain embodiments, the moiety -$L^1$- of formula (IIb-iii) is not further substituted.

In certain embodiments, the moiety -$L^1$- is of formula (IIb-iii'):

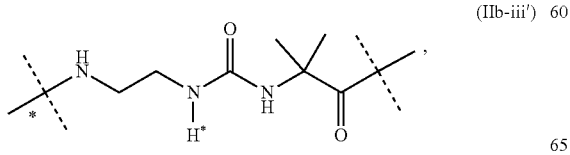
(IIb-iii')

wherein
the dashed line indicates the attachment to a nitrogen of -D which is a PTH moiety by forming an amide bond;
the dashed line marked with the asterisk indicates attachement to -$L^2$-; and
wherein -$L^1$- is substituted with -$L^2$-Z and wherein -$L^1$- is optionally further substituted, provided that the hydrogen marked with the asterisk in formula (IIb-iii') is not replaced by -$L^2$-Z or a substituent.

In certain embodiments, the moiety -$L^1$- of formula (IIb-iii') is not further substituted.

Another moiety is disclosed in WO 2016020373A1, which is herewith incorporated by reference in its entirety. Accordingly, in certain embodiments, the moiety -$L^1$- is of formula

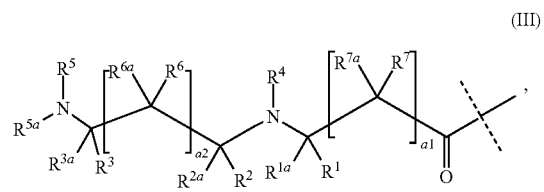
(III)

wherein
the dashed line indicates attachment to a primary or secondary amine or hydroxyl of -D which is a PTH moiety by forming an amide or ester linkage, respectively;
—$R^1$, —$R^{1a}$, —$R^2$, —$R^{2a}$, —$R^3$, and —$R^{3a}$ are independently of each other selected from the group consisting of —H, —$C(R^{8}R^{8a}R^{8b})$, —$C(=O)R^8$, —C≡N, —$C(=NR^8)R^{8a}$, —$CR^8(=CR^{8a}R^{8b})$, —C≡$CR^8$ and -T;
—$R^4$, —$R^5$ and —$R^{5a}$ are independently of each other selected from the group consisting of —H, —$C(R^9R^{9a}R^{9b})$ and -T;
a1 and a2 are independently of each other 0 or 1;
each —$R^6$, —$R^{6a}$, —$R^7$, —$R^{7a}$, —$R^8$, —$R^{8a}$, —$R^{8b}$, —$R^9$, —$R^{9a}$, —$R^{9b}$ are independently of each other selected from the group consisting of —H, halogen, —CN, —$COOR^{10}$, —$OR^{10}$, —$C(O)R^{10}$, —$C(O)N(R^{10}R^{10a})$, —$S(O)_2N(R^{10}R^{10a})$, $S(O)N(R^{10}R^{10a})$, —$S(O)_2R^{10}$, —$S(O)R^{10}$, —$N(R^{10})S(O)_2N(R^{10a}R^{10b})$, —$SR^{10}$, —$N(R^{10}R^{10a})$, —$NO_2$, —$OC(O)R^{10}$, —$N(R^{10})C(O)R^{10a}$, —$N(R^{10})S(O)_2R^{10a}$, —$N(R^{10})S(O)R^{10}$, —$N(R^{10})C(O)OR^{10a}$, —$N(R^{10})C(O)N(R^{10a}R^{10b})$, —$OC(O)N(R^{10}R^{10a})$, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more —$R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{12}$)—, —$S(O)_2N(R^{12})$—, —$S(O)N(R^{12})$—, —$S(O)_2$—, —S(O)—, —$N(R^{12})S(O)_2N(R^{12a})$—, —S—, —N($R^{12}$)—, —$OC(OR^{12})(R^{12a})$, —$N(R^{12})C(O)N(R^{12a})$—, and —$OC(O)N(R^{12})$—;
each is independently selected from the group consisting of —H, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more —$R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N(R$^{12}$)—, —S(O)$_2$N(R$^{12}$)—, —S(O)N(R$^{12}$)—, —S(O)$_2$—, —S(O)—, —N(R$^{12}$)S(O)$_2$N(R$^{12a}$)—, —S—, —N(R$^{12}$)—, —OC(OR$^{12}$)(R$^{12a}$)—, —N(R$^{12}$)C(O)N(R$^{12a}$), and —OC(O)N(R$^{12}$)—;

each T is independently of each other selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T is independently optionally substituted with one or more —R$^{11}$, which are the same or different;

each —R$^{11}$ is independently of each other selected from halogen, —CN, oxo (=O), —COOR$^{13}$, —OR$^{13}$, —C(O)R$^{13}$, —C(O)N(R$^{13}$R$^{13a}$), —S(O)$_2$N(R$^{13}$R$^{13a}$), —S(O)N(R$^{13}$R$^{13a}$), —S(O)$_2$R$^{13}$, —S(O)R$^{13}$, —N(R$^{13}$)S(O)$_2$N(R$^{13a}$R$^{13b}$), —SR$^{13}$, —N(R$^{13}$R$^{13a}$), —NO$_2$, —OC(O)R$^{13}$, —N(R$^{13}$)C(O)R$^{13a}$, —N(R$^{13}$)S(O)$_2$R$^{13a}$, —N(R$^{13}$)S(O)R$^{13a}$, —N(R$^{13}$)C(O)OR$^{13a}$, —N(R$^{13}$)C(O)N(R$^{13a}$R$^{13b}$), —OC(O)N(R$^{13}$R$^{13a}$), and C$_{1-6}$ alkyl; wherein C$_{1-6}$ alkyl is optionally substituted with one or more halogen, which are the same or different;

each —R$^{12}$, —R$^{12a}$, —R$^{13}$, —R$^{13a}$, R$^{13b}$ is independently selected from the group consisting of —H, and C$_{1-6}$ alkyl; wherein C$_{1-6}$ alkyl is optionally substituted with one or more halogen, which are the same or different;

optionally, one or more of the pairs —R$^1$/—R$^{1a}$, —R$^2$/—R$^{2a}$, —R$^3$/—R$^{3a}$, —R$^6$/—R$^{6a}$, —R$^7$/—R$^{7a}$ are joined together with the atom to which they are attached to form a C$_{3-10}$ cycloalkyl or a 3- to 10-membered heterocyclyl;

optionally, one or more of the pairs —R$^1$/—R$^2$, —R$^1$/—R$^3$, —R$^1$/—R$^4$, —R$^1$/—R$^5$, —R$^1$/—R$^6$, —R$^1$/—R$^7$, —R$^2$/—R$^3$, R$^2$/—R$^4$, —$^2$/—R$^5$, —R$^2$/—R$^6$, —R$^2$/—R$^7$, —R$^3$/—R$^4$, —R$^3$/—R$^5$, —R$^3$/—R$^6$, —R$^3$/—R$^7$, —R$^4$/—R$^5$, —R$^4$/—R$^6$, —R$^4$/—R$^7$, —R$^5$/—R$^6$, —R$^5$/—R$^7$, —R$^6$/—R$^7$ are joined together with the atoms to which they are attached to form a ring A;

A is selected from the group consisting of phenyl; naphthyl; indenyl; indanyl; tetralinyl; C$_{3-10}$ cycloalkyl; 3- to 10-membered heterocyclyl; and 8- to 11-membered heterobicyclyl;

wherein -L$^1$- is substituted with -L$^2$-Z and wherein -L$^1$- is optionally further substituted;
wherein
-L$^2$- is a single chemical bond or a spacer; and
—Z is a water-soluble carrier.

In certain embodiments, the optional further substituents of -L$^1$- of formula (III) are as described above.

In certain embodiments, -L$^1$- of formula (III) is substituted with one moiety -L$^2$-Z.

In certain embodiments, -L$^1$- of formula (III) is not further substituted.

Additional embodiments for -L$^1$- are disclosed in EP1536334B1, WO2009/009712A1, WO2008/034122A1, WO2009/143412A2, WO2011/082368A2 and U.S. Pat. No. 8,618,124B2, which are herewith incorporated by reference in their entirety.

Additional embodiments for -L$^1$- are disclosed in U.S. Pat. Nos. 8,946,405B2 and 8,754,190B2, which are herewith incorporated by reference in their entirety. Accordingly, a moiety -L$^1$- is of formula (IV):

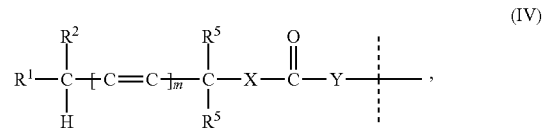

wherein
the dashed line indicates attachment to -D which is a PTH moiety and wherein attachment is through a functional group of -D selected from the group consisting of —OH, —SH and —NH$_2$;
m is 0 or 1;
at least one or both of —R$^1$ and —R$^2$ is/are independently of each other selected from the group consisting of —CN, —NO$_2$, optionally substituted aryl, optionally substituted heteroaryl, optionally substituted alkenyl, optionally substituted alkynyl, —C(O)R$^3$, —S(O)R$^3$, —S(O)$_2$R$^3$ and —SR$^4$;
one and only one of —R$^1$ and —R$^2$ is selected from the group consisting of —H, optionally substituted alkyl, optionally substituted arylalkyl, and optionally substituted heteroarylalkyl;
—R$^3$ is selected from the group consisting of —H, optionally substituted alkyl, optionally substituted aryl, optionally substituted arylalkyl, optionally substituted heteroaryl, optionally substituted heteroarylalkyl, —OR$^9$ and —N(R$^9$)$_2$;
—R$^4$ is selected from the group consisting of optionally substituted alkyl, optionally substituted aryl, optionally substituted arylalkyl, optionally substituted heteroaryl, and optionally substituted heteroarylalkyl;
each —R$^5$ is independently selected from the group consisting of —H, optionally substituted alkyl, optionally substituted alkenylalkyl, optionally substituted alkynylalkyl, optionally substituted aryl, optionally substituted arylalkyl, optionally substituted heteroaryl and optionally substituted heteroarylalkyl;
—R$^9$ is selected from the group consisting of —H and optionally substituted alkyl;
—Y— is absent and —X— is —O— or —S—; or
—Y— is —N(Q)CH$_2$— and —X— is —O—;
Q is selected from the group consisting of optionally substituted alkyl, optionally substituted aryl, optionally substituted arylalkyl, optionally substituted heteroaryl and optionally substituted heteroarylalkyl;
optionally, —R$^1$ and —R$^2$ may be joined to form a 3 to 8-membered ring; and
optionally, both —R$^9$ together with the nitrogen to which they are attached form a heterocyclic ring;
wherein -L$^1$- is substituted with -L$^2$-Z and wherein -L$^1$- is optionally further substituted;
wherein
-L$^2$- is a single chemical bond or a spacer; and
—Z is a water-soluble carrier.

Only in the context of formula (IV) the terms used have the following meaning:

The term "alkyl" as used herein includes linear, branched or cyclic saturated hydrocarbon groups of 1 to 8 carbons, or in some embodiments 1 to 6 or 1 to 4 carbon atoms.

The term "alkoxy" includes alkyl groups bonded to oxygen, including methoxy, ethoxy, isopropoxy, cyclopropoxy, cyclobutoxy, and similar.

The term "alkenyl" includes non-aromatic unsaturated hydrocarbons with carbon-carbon double bonds.

The term "alkynyl" includes non-aromatic unsaturated hydrocarbons with carbon-carbon triple bonds.

The term "aryl" includes aromatic hydrocarbon groups of 6 to 18 carbons, in certain embodiments 6 to 10 carbons, including groups such as phenyl, naphthyl, and anthracenyl. The term "heteroaryl" includes aromatic rings comprising 3 to 15 carbons containing at least one N, O or S atom, preferably 3 to 7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

In some instance, alkenyl, alkynyl, aryl or heteroaryl moieties may be coupled to the remainder of the molecule through an alkylene linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" includes bromo, fluoro, chloro and iodo.

The term "heterocyclic ring" refers to a 4 to 8 membered aromatic or non-aromatic ring comprising 3 to 7 carbon atoms and at least one N, O or S atom. Examples are piperidinyl, piperazinyl, tetrahydropyranyl, pyrrolidine, and tetrahydrofuranyl, as well as the exemplary groups provided for the term "heteroaryl" above.

When a ring system is optionally substituted, suitable substituents are selected from the group consisting of alkyl, alkenyl, alkynyl, and an additional ring, each optionally further substituted. Optional substituents on any group, including the above, include halo, nitro, cyano, —OR, —SR, —NR$_2$, —OCOR, —NRCOR, —COOR, —CONR$_2$, —SOR, —SO$_2$R, —SONR$_2$, —SO$_2$NR$_2$, wherein each R is independently alkyl, alkenyl, alkynyl, aryl or heteroaryl, or two R groups taken together with the atoms to which they are attached form a ring.

In certain embodiments, -L$^1$- of formula (IV) is substituted with one moiety -L2-Z.

An additional embodiment for -L$^1$- is disclosed in WO2013/036857A1, which is herewith incorporated by reference in its entirety. Accordingly, a moiety -L$^1$- is of formula (V):

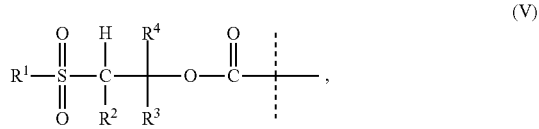

wherein
the dashed line indicates attachment to -D which is a PTH moiety and wherein attachment is through an amine functional group of -D;
—R$^1$ is selected from the group consisting of optionally substituted C$_1$-C$_6$ linear, branched, or cyclic alkyl; optionally substituted aryl; optionally substituted heteroaryl; alkoxy; and —NR$^5{}_2$;
—R$^2$ is selected from the group consisting of —H; optionally substituted C$_1$-C$_6$ alkyl; optionally substituted aryl; and optionally substituted heteroaryl;
—R$^3$ is selected from the group consisting of —H; optionally substituted C$_1$-C$_6$ alkyl; optionally substituted aryl; and optionally substituted heteroaryl;
—R$^4$ is selected from the group consisting of —H; optionally substituted C$_1$-C$_6$ alkyl; optionally substituted aryl; and optionally substituted heteroaryl;
each —R$^5$ is independently of each other selected from the group consisting of —H; optionally substituted C$_1$-C$_6$ alkyl; optionally substituted aryl; and optionally substituted heteroaryl; or when taken together two —R$^5$ can be cycloalkyl or cyclohetroalkyl;
wherein -L$^1$- is substituted with -L$^2$-Z and wherein is optionally further substituted;
wherein
-L$^2$- is a single chemical bond or a spacer; and
—Z is a water-soluble carrier.

Only in the context of formula (V) the terms used have the following meaning:

"Alkyl", "alkenyl", and "alkynyl" include linear, branched or cyclic hydrocarbon groups of 1-8 carbons or 1-6 carbons or 1-4 carbons wherein alkyl is a saturated hydrocarbon, alkenyl includes one or more carbon-carbon double bonds and alkynyl includes one or more carbon-carbon triple bonds. Unless otherwise specified these contain 1-6 C.

"Aryl" includes aromatic hydrocarbon groups of 6-18 carbons, preferably 6-10 carbons, including groups such as phenyl, naphthyl, and anthracene.

"Heteroaryl" includes aromatic rings comprising 3-15 carbons containing at least one N, O or S atom, in certain embodiments 3-7 carbons containing at least one N, O or S atom, including groups such as pyrrolyl, pyridyl, pyrimidinyl, imidazolyl, oxazolyl, isoxazolyl, thiszolyl, isothiazolyl, quinolyl, indolyl, indenyl, and similar.

The term "substituted" means an alkyl, alkenyl, alkynyl, aryl, or heteroaryl group comprising one or more substituent groups in place of one or more hydrogen atoms.

Substituents may generally be selected from halogen including F, Cl, Br, and I; lower alkyl including linear, branched, and cyclic; lower haloalkyl including fluoroalkyl, chloroalkyl, bromoalkyl, and iodoalkyl; OH; lower alkoxy including linear, branched, and cyclic; SH; lower alkylthio including linear, branched and cyclic; amino, alkylamino, dialkylamino, silyl including alkylsilyl, alkoxysilyl, and arylsilyl; nitro; cyano; carbonyl; carboxylic acid, carboxylic ester, carboxylic amide, aminocarbonyl; aminoacyl; carbamate; urea; thiocarbamate; thiourea; ketne; sulfone; sulfonamide; aryl including phenyl, naphthyl, and anthracenyl; heteroaryl including 5-member heteroaryls including as pyrrole, imidazole, furan, thiophene, oxazole, thiazole, isoxazole, isothiazole, thiadiazole, triazole, oxadiazole, and tetrazole, 6-member heteroaryls including pyridine, pyrimidine, pyrazine, and fused heteroaryls including benzofuran, benzothiophene, benzoxazole, benzimidazole, indole, benzothiazole, benzisoxazole, and benzisothiazole.

In certain embodiments, -L$^1$- of formula (V) is substituted with one moiety -L$^2$-Z.

Another embodiment for -L$^1$- is disclosed in U.S. Pat. No. 7,585,837B2, which is herewith incorporated by reference in its entirety. Accordingly, a moiety -L$^1$- is of formula (VI):

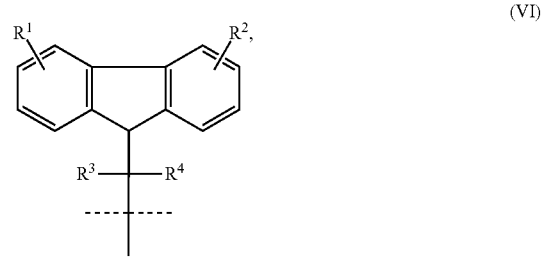

wherein the dashed line indicates attachment to -D which is a PTH moiety and wherein attachment is through an amine functional group of -D;

$R^1$ and $R^2$ are independently selected from the group consisting of hydrogen, alkyl, alkoxy, alkoxyalkyl, aryl, alkaryl, aralkyl, halogen, nitro, —SO$_3$H, —SO$_2$NHR$^5$, amino, ammonium, carboxyl, PO$_3$H$_2$, and OPO$_3$H$_2$;

$R^3$, $R^4$, and $R^5$ are independently selected from the group consisting of hydrogen, alkyl, and aryl;

wherein -L$^1$- is substituted with -L$^2$-Z and wherein -L$^1$- is optionally further substituted;

wherein

-L$^2$- is a single chemical bond or a spacer; and

—Z is a water-soluble carrier.

Suitable substituents for formulas (VI) are alkyl (such as C$_{1-6}$ alkyl), alkenyl (such as C$_{2-6}$ alkenyl), alkynyl (such as C$_{2-6}$ alkynyl), aryl (such as phenyl), heteroalkyl, heteroalkenyl, heteroalkynyl, heteroaryl (such as aromatic 4 to 7 membered heterocycle) or halogen moieties.

Only in the context of formula (VI) the terms used have the following meaning:

The terms "alkyl", "alkoxy", "alkoxyalkyl", "aryl", "alkaryl" and "aralkyl" mean alkyl radicals of 1-8, in certain embodiments 1-4 carbon atoms, e.g. methyl, ethyl, propyl, isopropyl and butyl, and aryl radicals of 6-10 carbon atoms, e.g. phenyl and naphthyl. The term "halogen" includes bromo, fluoro, chloro and iodo.

In certain embodiments, -L$^1$- of formula (VI) is substituted with one moiety -L$^2$-Z.

A further embodiment for -L$^1$- is disclosed in WO2002/089789A1, which is herewith incorporated by reference in its entirety. Accordingly, a in certain embodiments -L$^1$- is of formula (VII):

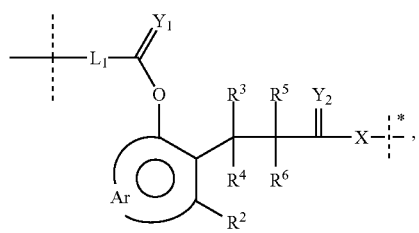

(VII)

wherein the dashed line indicates attachment to -D which is a PTH moiety and wherein attachment is through an amine functional group of -D;

L$_1$ is a bifunctional linking group;

Y$_1$ and Y$_2$ are independently O, S or NR$^7$;

R$^2$, R$^3$, R$^4$, R$^5$, R$^6$ and R$^7$ are independently selected from the group consisting of hydrogen, C$_{1-6}$ alkyls, C$_{3-12}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxy, phenoxy, and C$_{1-6}$ heteroalkoxy;

Ar is a moiety which when included in formula (VII) forms a multi-substituted aromatic hydrocarbon or a multi-substituted heterocyclic group;

X is a chemical bond or a moiety that is actively transported into a target cell, a hydrophobic moiety, or a combination thereof, y is 0 or 1;

wherein is substituted with -L$^2$-Z and wherein is optionally further substituted;

wherein

-L$^2$- is a single chemical bond or a spacer; and

—Z is a water-soluble carrier.

Only in the context of formula (VII) the terms used have the following meaning:

The term "alkyl" shall be understood to include, e.g. straight, branched, substituted C$_{1-12}$ alkyls, including alkoxy, C$_{3-8}$ cycloalkyls or substituted cycloalkyls, etc.

The term "substituted" shall be understood to include adding or replacing one or more atoms contained within a functional group or compounds with one or more different atoms.

Substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxythiophone; alkoxy includes moieities such as methoxy; and phenoxy includes moieties such as 3-nitrophenoxy. Halo—shall be understood to include fluoro, chloro, iodo and bromo.

In certain embodiments, -L$^1$- of formula (VII) is substituted with one moiety -L$^2$-Z.

In certain embodiments, -L$^1$- comprises a substructure of formula (VIII):

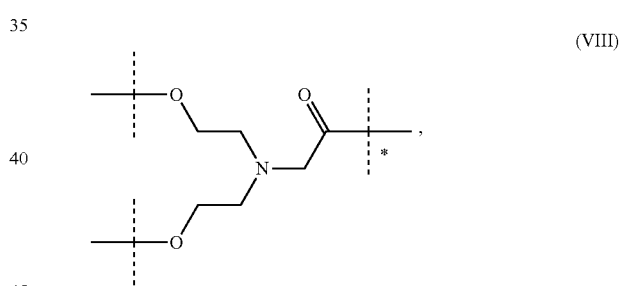

(VIII)

wherein the dashed line marked with the asterisk indicates attachment to a nitrogen of -D which is a PTH moiety by forming an amide bond;

the unmarked dashed lines indicate attachment to the remainder of -L$^1$-; and wherein -L$^1$- is substituted with -L$^2$-Z and -L$^1$- is optionally further substituted;

wherein

-L$^2$- is a single chemical bond or a spacer; and

—Z is a water-soluble carrier.

In certain embodiments, -L$^1$- of formula (VIII) is substituted with one moiety -L$^2$-Z.

In certain embodiments, -L$^1$- of formula (VIII) is not further substituted.

In certain embodiments, -L$^1$- comprises a substructure of formula (IX):

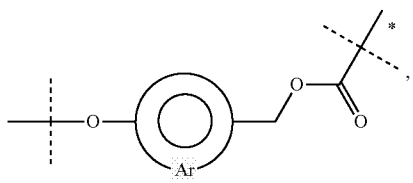

(IX)

wherein
the dashed line marked with the asterisk indicates attachment to a nitrogen of -D which is a PTH moiety by forming a carbamate bond;
the unmarked dashed lines indicate attachment to the remainder of -$L^1$-; and wherein -$L^1$- is substituted with -$L^2$-Z and wherein -$L^1$- is optionally further substituted;
wherein
-$L^2$- is a single chemical bond or a spacer; and
—Z is a water-soluble carrier.

In certain embodiments, -$L^1$- of formula (IX) is substituted with one moiety -$L^2$-Z.

In certain embodiments, -$L^1$- of formula (IX) is not further substituted.

In certain embodiments, -$L^2$- is a chemical bond or a spacer moiety.

In certain embodiments, -$L^2$- is a chemical bond. In certain embodiments, -$L^2$- is a spacer moiety.

When -$L^2$- is other than a single chemical bond, -$L^2$- is selected from the group consisting of -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more —$R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y4}$)—, —S(O)$_2$N($R^{y4}$)—, —S(O)N($R^{y4}$)—, —S(O)$_2$—, —S(O)—, —N($R^{y4}$)S(O)$_2$N($R^{y4a}$)—, —S—, —N($R^{y4}$)—, —OC(O$R^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

each —$R^{y2}$ is independently selected from the group consisting of halogen, —CN, oxo (=O), —COO$R^{y5}$, —O$R^{y5}$, —C(O)$R^{y5}$, —C(O)N($R^{y5}R^{y5a}$), —S(O)$_2$N($R^{y5}R^{y5a}$), —S(O)N($R^{y5}R^{y5a}$), —S(O)$_2R^{y5}$, —S(O)$R^{y5}$, —N($R^{y5}$)S(O)$_2$N($R^{y5a}R^{y5b}$), —S$R^{y5}$, —N($R^{y5}R^{y5a}$), —NO$_2$, —OC(O)$R^{y5}$, —N($R^{y5}$)C(O)$R^{y5a}$, —N($R^{y5}$)S(O)$_2R^{y5a}$, —N($R^{y5}$)S(O)$R^{y5a}$, —N($R^{y5}$)C(O)O$R^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently selected from the group consisting of —H and $C_{1-6}$ alkyl, wherein $C_{1-6}$ alkyl is optionally substituted with one or more halogen, which are the same or different.

When -$L^2$- is other than a single chemical bond, -$L^2$- is, in certain embodiments, selected from -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-20}$ alkyl, $C_{2-20}$ alkenyl, and $C_{2-20}$ alkynyl; wherein -T-, $C_{1-20}$ alkyl, $C_{2-20}$ alkenyl, and $C_{2-20}$ alkynyl are optionally substituted with one or more —$R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—; —$R^{y1}$ and —$R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more —$R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N($R^{y4}$)—, —S(O)$_2$N($R^{y4}$)—, —S(O)N($R^{y4}$)—, —S(O)$_2$—, —S(O)—, —N($R^{y4}$)S(O)$_2$N($R^{y4a}$)—, —S—, —N($R^{y4}$)—, —OC(O$R^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

—$R^{y2}$ is selected from the group consisting of halogen, —CN, oxo (=O), —COO$R^{y5}$, —O$R^{y5}$, —C(O)$R^{y5}$, —C(O)N($R^{y5}R^{y5a}$), —S(O)$_2$N($R^{y5}R^{y5a}$), —S(O)N($R^{y5}R^{y5a}$), —S(O)$_2R^{y5}$, —S(O)$R^{y5}$, —N($R^{y5}$)S(O)$_2$N($R^{y5a}R^{y5b}$), —S$R^{y5}$, —N($R^{y5}R^{y5a}$), —NO$_2$, —OC(O)$R^{y5}$, —N($R^{y5}$)C(O)$R^{y5a}$, —N($R^{y5}$)S(O)$_2R^{y5a}$, —N($R^{y5}$)S(O)$R^{y5a}$, —N($R^{y5}$)C(O)O$R^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y}$, —$R^{y3a}$, —$R^{y4}$, —$R^{y4a}$, —$R^{yb5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different.

When -$L^2$- is other than a single chemical bond, -$L^2$- is selected from the group consisting of -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N (R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-50}$ alkyl, C$_{2-50}$ alkenyl, and C$_{2-50}$ alkynyl are optionally substituted with one or more —R$^{y2}$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and —R$^{y1a}$ are independently selected from the group consisting of —H, -T, C$_{1-10}$ alkyl, C$_{2-10}$ alkenyl, and C$_{2-10}$ alkynyl;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —R$^{y2}$ is independently selected from the group consisting of halogen, and C$_{1-6}$ alkyl; and each —R$^{y3}$, —R$^{y3a}$, —R$^{y4}$, —R$^{y4a}$, —R$^{y5}$, —R$^{y5a}$ and —R$^{y5b}$ is independently of each other selected from the group consisting of —H, and C$_{1-6}$ alkyl; wherein C$_{1-6}$ alkyl is optionally substituted with one or more halogen, which are the same or different.

In certain embodiments, -L$^2$- is a C$_{1-20}$ alkyl chain, which is optionally interrupted by one or more groups independently selected from —O—, -T- and —C(O)N(R$^{y1}$)—; and which C$_{1-20}$ alkyl chain is optionally substituted with one or more groups independently selected from —OH, -T and —C(O)N(R$^{y6}$R$^{y6a}$); wherein —R$^{y1}$, —R$^{y6}$, —R$^{y6a}$ are independently selected from the group consisting of H and C$_{1-4}$ alkyl and wherein T is selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl.

In certain embodiments, -L$^2$- has a chain length of 1 to 20 atoms.

As used herein, the term "chain length" with regard to the moiety -L$^2$- refers to the number of atoms of -L$^2$- present in the shortest connection between -L$^1$- and —Z.

In certain embodiments, -L$^2$- is of formula (i)

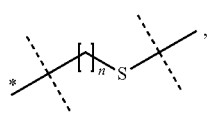
(i)

wherein
the dashed line marked with the asterisk indicates attachment to -L$^1$-;
the unmarked dashed line indicates attachment to —Z;
n is selected from the group consisting of 0, 1, 2, 3, 4, 5, 6, 7, 8, 9, 10, 11, 12, 13, 14, 15, 16, 17 and 18; and
wherein the moiety of formula (i) is optionally further substituted.

In certain embodiments, n of formula (i) is selected from the group consisting of 3, 4, 5, 6, 7, 8 and 9. In certain embodiments, n of formula (i) is 4, 5, 6 or 7. In certain embodiments, n of formula (i) is 4. In certain embodiments, n of formula (i) is 5. In certain embodiments, n of formula (i) is 6.

In certain embodiments, the moiety -L$^1$-L$^2$- is selected from the group consisting of

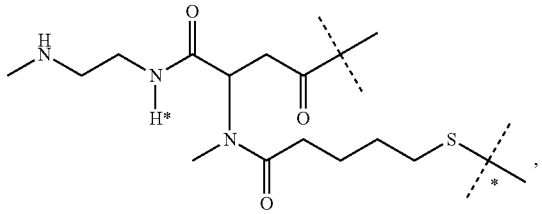
(IIca-i)

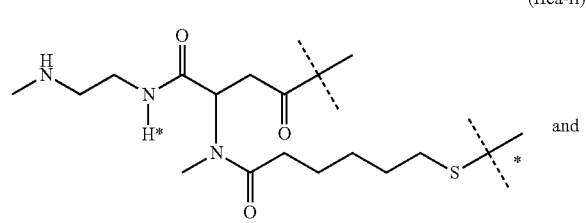
(IIca-ii)

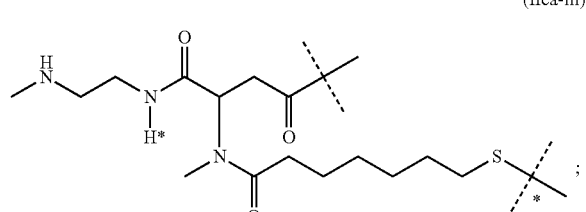
(IIca-iii)

wherein
the unmarked dashed line indicates the attachment to a nitrogen of -D which is a PTH moiety by forming an amide bond; and
the dashed line marked with the asterisk indicates attachment to —Z.

In certain embodiments, the moiety -L$^1$-L$^2$- is selected from the group consisting of

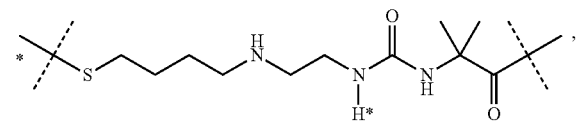
(IIcb-i)

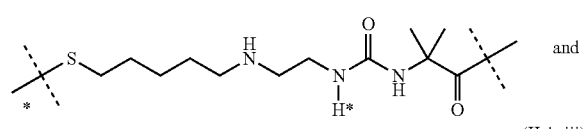
(IIcb-ii)

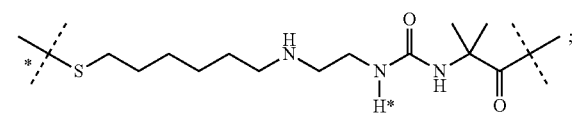
(IIcb-iii)

wherein
the unmarked dashed line indicates the attachment to a nitrogen of -D which is a PTH moiety by forming an amide bond; and
the dashed line marked with the asterisk indicates attachment to —Z.

In certain embodiments, the moiety -L¹-L²- is of formula (IIca-ii).

In certain embodiments, the moiety -L¹-L²- is of formula (IIcb-iii).

In certain embodiments, the PTH conjugate is of formula (Ia) with x=1.

The carrier —Z comprises a $C_{8-24}$ alkyl or a polymer. In certain embodiments, —Z comprises a polymer. In certain embodiments, —Z comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In certain embodiments, —Z has a molecular weight ranging from 5 to 200 kDa. In certain embodiments, —Z has a molecular weight ranging from 8 to 100 kDa. In certain embodiments, —Z has a molecular weight ranging from 10 to 80 kDa. In certain embodiments, —Z has a molecular weight ranging from 12 to 60 kDa. In certain embodiments, —Z has a molecular weight ranging from 15 to 40 kDa. In certain embodiments, —Z has a molecular weight of about 20 kDa. In certain embodiments, —Z has a molecular weight of about 40 kDa.

In certain embodiments, such water-soluble carrier —Z comprises a protein. In certain embodiments, the proteins are selected from the group consisting of carboxyl-terminal polypeptide of the chorionic gonadotropin as described in US 2012/0035101 A1 which are herewith incorporated by reference; albumin; XTEN sequences as described in WO 2011/123813 A2 which are herewith incorporated by reference; proline/alanine random coil sequences as described in WO 2011/144756 A1 which are herewith incorporated by reference; proline/alanine/serine random coil sequences as described in WO 2008/155134 A1 and WO 2013/024049 A1 which are herewith incorporated by reference; and Fc fusion proteins.

In certain embodiments, —Z is a polysarcosine. In certain embodiments, —Z comprises a poly(N-methylglycine). In certain embodiments, —Z comprises a random coil protein moiety.

In certain embodiments, —Z comprises one random coil protein moiety. In certain embodiments, —Z comprises two random coil proteins moieties. In certain embodiments, —Z comprises three random coil proteins moieties. In certain embodiments, —Z comprises four random coil proteins moieties. In certain embodiments, —Z comprises five random coil proteins moieties. In certain embodiments, —Z comprises six random coil proteins moieties. In certain embodiments, —Z comprises seven random coil proteins moieties. In certain embodiments, —Z comprises eight random coil proteins moieties.

In certain embodiments, such random coil protein moiety comprises at least 25 amino acid residues and at most 2000 amino acids. In certain embodiments, such random coil protein moiety comprises at least 30 amino acid residues and at most 1500 amino acid residues. In certain embodiments, such random coil protein moiety comprises at least 50 amino acid residues and at most 500 amino acid residues.

In certain embodiments, —Z comprises a random coil protein moiety of which at least 80%, in certain embodiments at least 85%, in certain embodiments at least 90%, in certain embodiments at least 95%, in certain embodiments at least 98% and in certain embodiments at least 99% of the total number of amino acids forming said random coil protein moiety are selected from alanine and proline. In certain embodiments, at least 10%, but less than 75%, in certain embodiments less than 65% of the total number of amino acid residues of such random coil protein moiety are proline residues. In certain embodiments, such random coil protein moiety is as described in WO 2011/144756 A1 which is hereby incorporated by reference in its entirety.

In certain embodiments, —Z comprises at least one moiety selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:51 and SEQ ID NO:61 as disclosed in WO2011/144756, which are hereby incorporated by reference. A moiety comprising such random coil protein comprising alanine and proline will be referred to as "PA" or "PA moiety".

Accordingly, —Z comprises a PA moiety.

In certain embodiments, —Z comprises a random coil protein moiety of which at least 80%, in certain embodiments at least 85%, in certain embodiments at least 90%, in certain embodiments at least 95%, in certain embodiments at least 98% and in certain embodiments at least 99% of the total number of amino acids forming said random coil protein moiety are selected from alanine, serine and proline. In certain embodiments, at least 4%, but less than 40% of the total number of amino acid residues of such random coil protein moiety are proline residues. In certain embodiments, such random coil protein moiety is as described in WO 2008/155134 A1, which is hereby incorporated by reference in its entirety. In certain embodiments, —Z comprises at least one moiety selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:40, SEQ ID NO:42, SEQ ID NO:44, SEQ ID NO:46, SEQ ID NO:50, SEQ ID NO:52, SEQ ID NO:54 and SEQ ID NO:56 as disclosed in WO 2008/155134 A1, which are hereby incorporated by reference. A moiety comprising such random coil protein moiety comprising alanine, serine and proline will be referred to as "PAS" or "PAS moiety".

Accordingly, —Z comprises a PAS moiety.

In certain embodiments, —Z comprises a random coil protein moiety of which at least 80%, in certain embodiments at least 85%, in certain embodiments at least 90%, in certain embodiments at least 95%, in certain embodiments at least 98% and in certain embodiments at least 99% of the total number of amino acids forming said random coil protein moiety are selected from alanine, glycine and proline. A moiety comprising such random coil protein moiety comprising alanine, glycine and proline will be referred to as "PAG" or "PAG moiety".

Accordingly, —Z comprises a PAG moiety.

In certain embodiments, —Z comprises a random coil protein moiety of which at least 80%, in certain embodiments at least 85%, in certain embodiments at least 90%, in certain embodiments at least 95%, in certain embodiments at least 98% and in certain embodiments at least 99% of the total number of amino acids forming said random coil protein moiety are selected from proline and glycine. A moiety comprising such random coil protein moiety comprising proline and glycine will be referred to as "PG" or "PG moiety". In certain embodiments, such PG moiety comprises a moiety of formula (a-0)

[(Gly)$_p$-Pro-(Gly)$_q$]$_r$ (a-0);
wherein
p is selected from the group consisting of 0, 1, 2, 3, 4 and 5;
q is selected from the group consisting of 0, 1, 2, 3, 4 and 5;
r is an integer ranging from and including 10 to 1000;
provided that at least one of p and q is at least 1;
In certain embodiments, p of formula (a-0) is selected from the group consisting of 1, 2 and 3.

In certain embodiments, q of formula (a-0) is selected from 0, 1 and 2.

In certain embodiments, the PG moiety comprises the sequence of SEQ ID NO:122: GGPGGPGPGGPGGPGPGGPG.

In certain embodiments, the PG moiety comprises the sequence of SEQ ID NO:97 of formula (a-0-a)
(GGPGGPGPGGPGGPGPGGPG)$_v$ (a-0-a),
wherein
v is an integer ranging from and including 1 to 50.

Accordingly, —Z comprises a PG moiety.

In certain embodiments, —Z comprises a random coil protein moiety of which at least 80%, in certain embodiments at least 85%, in certain embodiments at least 90%, in certain embodiments at least 95%, in certain embodiments at least 98% and in certain embodiments at least 99% of the total number of amino acids forming said random coil protein moiety are selected from alanine, glycine, serine, threonine, glutamate and proline. In certain embodiments, such random coil protein moiety is as described in WO 2010/091122 A1, which is hereby incorporated by reference. In certain embodiments, —Z comprises at least one moiety selected from the group consisting of SEQ ID NO:182, SEQ ID NO:183, SEQ ID NO:184; SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:759, SEQ ID NO:760, SEQ ID NO:761, SEQ ID NO:762, SEQ ID NO:763, SEQ ID NO:764, SEQ ID NO:765, SEQ ID NO:766, SEQ ID NO:767, SEQ ID NO:768, SEQ ID NO:769, SEQ ID NO:770, SEQ ID NO:771, SEQ ID NO:772, SEQ ID NO:773, SEQ ID NO:774, SEQ ID NO:775, SEQ ID NO:776, SEQ ID NO:777, SEQ ID NO:778, SEQ ID NO:779, SEQ ID NO:1715, SEQ ID NO:1716, SEQ ID NO:1718, SEQ ID NO:1719, SEQ ID NO:1720, SEQ ID NO:1721 and SEQ ID NO:1722 as disclosed in WO2010/091122A1, which are hereby incorporated by reference. A moiety comprising such random coil protein moiety comprising alanine, glycine, serine, threonine, glutamate and proline will be referred to as "XTEN" or "XTEN moiety" in line with its designation in WO 2010/091122 A1.

Accordingly, —Z comprises an XTEN moiety.

In certain embodiments, —Z comprises a fatty acid derivate. In certain embodiments, fatty acid derivatives are those disclosed in WO 2005/027978 A2 and WO 2014/060512 A1, which are herewith incorporated by reference.

In certain embodiments, —Z is a hyaluronic acid-based polymer.

In certain embodiments, —Z is a carrier as disclosed in WO 2012/02047 A1, which is herewith incorporated by reference. In certain embodiments, —Z is a carrier as disclosed in WO 2013/024048 A1, which is herewith incorporated by reference.

In certain embodiments, —Z is a PEG-based polymer, such as a linear, branched or multi-arm PEG-based polymer.

In certain embodiments, —Z is a linear PEG-based polymer.

In certain embodiments, —Z is a multi-arm PEG-based polymer. In certain embodiments, —Z is a multi-arm PEG-based polymer having at least 4 PEG-based arms.

In certain embodiments, such multi-arm PEG-based polymer —Z is connected to a multitude of moieties -L$^2$-L$^1$-D, wherein each moiety -L$^2$-L$^1$-D is, in certain embodiments, connected to the end of an arm. In certain embodiments, such multi-arm PEG-based polymer —Z is connected to 2, 3, 4, 5, 6, 7, 8, 9, 10, 11, 12, 13, 14, 15 or 16 moieties -L$^2$-L$^1$-D. In certain embodiments, such multi-arm PEG-based polymer —Z is connected to 2, 3, 4, 6 or 8 moieties -L$^2$-L$^1$-D. In certain embodiments, such multi-arm PEG-based polymer —Z is connected to 2, 4 or 6 moieties -L$^2$-L$^1$-D, in certain embodiments such multi-arm PEG-based polymer —Z is connected to 4 or 6 moieties -L$^2$-L$^1$-D, and in certain embodiments such multi-arm PEG-based polymer —Z is connected to 4 moieties -L$^2$-L$^1$-D.

In certain embodiments, such multi-arm PEG-based polymer —Z is a multi-arm PEG derivative as, for instance, detailed in the products list of JenKem Technology, USA (accessed by download from http://www.jenkemusa.com/Pages/PEGProducts.aspx on Dec. 18, 2014), such as a 4-arm-PEG derivative, in particular a 4-arm-PEG comprising a pentaerythritol core, an 8-arm-PEG derivative comprising a hexaglycerin core, and an 8-arm-PEG derivative comprising a tripentaerythritol core. In certain embodiments, the water-soluble PEG-based carrier —Z comprises a moiety selected from:

a 4-arm PEG Amine comprising a pentaerythritol core:

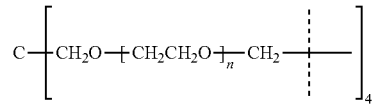

with n ranging from 20 to 500;

an 8-arm PEG Amine comprising a hexaglycerin core:

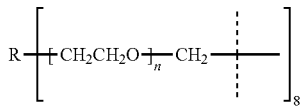

with n ranging from 20 to 500; and
R=hexaglycerin or tripentaerythritol core structure; and
a 6-arm PEG Amine comprising a sorbitol or dipentaerythritol core:

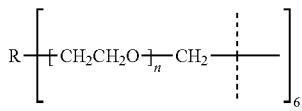

with n ranging from 20 to 500; and
R=comprising a sorbitol or dipentaerythritol core;
and wherein dashed lines indicate attachment to the rest of the PTH conjugate.

In certain embodiments, —Z is a branched PEG-based polymer. In certain embodiments, —Z is a branched PEG-based polymer having one, two, three, four, five or six branching points. In certain embodiments, —Z is a branched PEG-based polymer having one, two or three branching points. In certain embodiments, —Z is a branched PEG-based polymer having one branching point. In certain embodiments, —Z is a branched PEG-based polymer having two branching points. In certain embodiments, —Z is a branched PEG-based polymer having three branching points.

In certain embodiments, a branching point is selected from the group consisting of —N<, —CH< and >C<.

In certain embodiments, such branched PEG-based moiety —Z has a molecular weight of at least 10 kDa.

In certain embodiments, such branched moiety —Z has a molecular weight ranging from and including 10 kDa to 500 kDa. In certain embodiments, such branched moiety —Z has a molecular weight ranging from and including 10 kDa to 250 kDa. In certain embodiments, such branched moiety —Z has a molecular weight ranging from and including 10 kDa to 150 kDa. In certain embodiments, such branched moiety —Z has a molecular weight ranging from and including 12 kDa to 100 kDa. In certain embodiments, such branched moiety —Z has a molecular weight ranging from and including 15 kDa to 80 kDa.

In certain embodiments, such branched moiety —Z has a molecular weight ranging from and including 10 kDa to 80 kDa. In certain embodiments, the molecular weight is about 10 kDa. In certain embodiments, the molecular weight of such branched moiety —Z is about 20 kDa. In certain embodiments, the molecular weight of such branched moiety —Z is about 30 kDa. In certain embodiments, the molecular weight of such a branched moiety —Z is about 40 kDa. In certain embodiments, the molecular weight of such a branched moiety —Z is about 50 kDa. In certain embodiments, the molecular weight of such a branched moiety —Z is about 60 kDa. In certain embodiments, the molecular weight of such a branched moiety —Z is about 70 kDa. In certain embodiments, the molecular weight of such a branched moiety —Z is about 80 kDa. In certain embodiments, such branched moiety —Z has a molecular weight of about 40 kDa.

In certain embodiments, —Z comprises a moiety

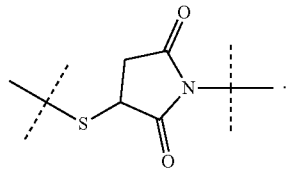

In certain embodiments, —Z comprises an amide bond.
In certain embodiments, —Z comprises a moiety of formula (a)

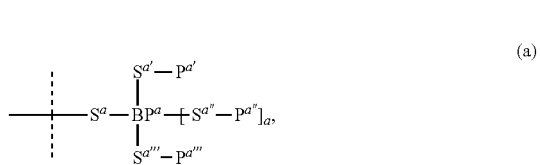

wherein
the dashed line indicates attachment to -$L^2$- or to the remainder of —Z;
$BP^a$ is a branching point selected from the group consisting of —N<, —CR< and >C<;
—R is selected from the group consisting of —H and $C_{1-6}$ alkyl;
a is 0 if $BP^a$ is —N< or —CR< and n is 1 if $BP^a$ is >C<;
—$S^a$—, —$S^{a'}$—, —$S^{a''}$— and —$S^{a'''}$— are independently of each other a chemical bond or are selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more —$R^1$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^2$)—, —S(O)$_2$N($R^2$)—, —S(O)N($R^2$)—, —S(O)$_2$—, —S(O)—, —N($R^2$)S(O)$_2$N($R^{2a}$)—, —S—, —N($R^2$)—, —OC(O$R^2$)($R^{2a}$)—, —N($R^2$)C(O)N($R^{2a}$)— and —OC(O)N($R^2$)—;
each -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more —$R^1$, which are the same or different;
each —$R^1$ is independently selected from the group consisting of halogen, —CN, oxo (=O), —COO$R^3$, —O$R^3$, —C(O)$R^3$, —C(O)N($R^3R^{3a}$), —S(O)$_2$N($R^3R^{3a}$), —S(O)N($R^3R^{3a}$), —S(O)$_2R^3$, —S(O)$R^3$, —N($R^3$)S(O)$_2$N($R^{3a}R^{3b}$), —S$R^3$, —N($R^3R^{3a}$), —NO$_2$, —OC(O)$R^3$, —N($R^3$)C(O)$R^{3a}$, —N($R^3$)S(O)$_2R^{3a}$, —N($R^3$)S(O)$R^{3a}$, —N($R^3$)C(O)O$R^{3a}$, —N($R^3$)C(O)N($R^{3a}R^{3b}$), —OC(O)N($R^3R^{3a}$), and $C_{1-6}$ alkyl; wherein $C_{1-6}$ alkyl is optionally substituted with one or more halogen, which are the same or different;
each —$R^2$, —$R^{2a}$, —$R^3$, —$R^{3a}$ and —$R^{3b}$ is independently selected from the group consisting of —H, and $C_{1-6}$ alkyl, wherein $C_{1-6}$ alkyl is optionally substituted with one or more halogen, which are the same or different; and
—$P^{a'}$, —$P^{a''}$ and —$P^{a'''}$ are independently a polymeric moiety.

In certain embodiments, $BP^a$ of formula (a) is –N<. In certain embodiments, $BP^a$ of formula (a) is >C<. In certain embodiments, $BP^a$ of formula (a) is —CR<. In certain embodiments, —R is —H. Accordingly, a of formula (a) is 0.

In certain embodiments, —$S^a$— of formula (a) is a chemical bond.

In certain embodiments, —$S^a$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of -T-, —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N ($R^{4a}$)—, —S—, —N($R^4$)—, —OC(O$R^4$)($R^{4a}$)—, —N($R^4$)C(O)N($R^{4a}$)—, and —OC(O)N($R^4$)—; wherein -T- is a 3- to 10-membered heterocyclyl; and —$R^4$ and —$R^{4a}$ are independently selected from the group consisting of —H, methyl, ethyl, propyl and butyl.

In certain embodiments, —$S^a$— of formula (a) is $C_{1-10}$ alkyl, which is interrupted by one or more chemical groups selected from the group consisting of -T-, —C(O)N($R^4$)— and —O—.

In certain embodiments, —$S^{a'}$— of formula (a) is a chemical bond.

In certain embodiments, —$S^{a'}$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N ($R^{4a}$)—, —S—, —N($R^4$)—, —OC(O$R^4$)($R^{4a}$)—, N($R^4$)C(O)N($R^{4a}$)—, and —OC(O)N($R^4$)—; wherein —$R^4$ and —$R^{4a}$ are independently selected from the group consisting of —H, methyl, ethyl, propyl and butyl. In certain embodiments, —$S^{a'}$— of formula (a) is selected from the group consisting of methyl, ethyl, propyl, butyl, which are optionally interrupted by one or more chemical groups selected from the group consisting of —O—, —C(O)— and —C(O)N($R^4$)—.

In certain embodiments, —$S^{a''}$— of formula (a) is a chemical bond.

In certain embodiments, —$S^{a''}$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —S(O)$_2$N ($R^4$)—, —S(O)N($R^4$)—, —S(O)$_2$—, —S(O)—, —N($R^4$)S (O)$_2$N($R^{4a}$)—, —S—, —N($R^4$)—, —OC(O$R^4$)($R^{4a}$)—, N($R^4$)C(O)N($R^{4a}$)—, and —OC(O)N($R^4$)—; wherein —$R^4$ and —$R^{4a}$ are independently selected from the group consisting of —H, methyl, ethyl, propyl and butyl. In certain embodiments, —$S^{a''}$— of formula (a) is selected from the group consisting of methyl, ethyl, propyl, butyl, which are optionally interrupted by one or more chemical groups selected from the group consisting of —O—, —C(O)— and —C(O)N($R^4$)—.

In certain embodiments, —$S^{a'''}$— of formula (a) is a chemical bond.

In certain embodiments, —$S^{a'''}$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —S(O)$_2$N ($R^4$)—, —S(O)N($R^4$)—, —S(O)$_2$—, —S(O)—, —N($R^4$)S (O)$_2$N($R^{4a}$)—, —S—, —N($R^4$)—, —OC(O$R^4$)($R^{4a}$)—, N($R^4$)C(O)N($R^{4a}$)—, and —OC(O)N($R^4$)—; wherein —$R^4$ and —$R^{4a}$ are independently selected from the group consisting of —H, methyl, ethyl, propyl and butyl. In certain embodiments, —$S^{a'''}$— of formula (a) is selected from the group consisting of methyl, ethyl, propyl, butyl, which are optionally interrupted by one or more chemical groups selected from the group consisting of —O—, —C(O)— and —C(O)N($R^4$)—.

In certain embodiments, —$P^{a'}$, —$P^{a''}$ and —$P^{a'''}$ of formula (a) independently comprise a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly (ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly (lactic-co-glycolic acids), poly(methacrylamides), poly (methacrylates), poly(methyloxazolines), poly (organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In certain embodiments, —$P^{a'}$, —$P^{a''}$ and —$P^{a'''}$ of formula (a) independently comprise a PEG-based moiety. In certain embodiments, —$P^{a'}$, —$P^{a''}$ and —$P^{a'''}$ of formula (a) independently comprise a PEG-based moiety comprising at least 20% PEG, in certain embodiments comprising at least 30%, in certain embodiments comprising at least 40% PEG, in certain embodiments comprising at least 50% PEG, in certain embodiments comprising at least 60% PEG, in certain embodiments comprising at least 70% PEG, in certain embodiments comprising at least 80% PEG and in certain embodiments comprising at least 90% PEG.

In certain embodiments, —$P^{a'}$, —$P^{a''}$ and —$P^{a'''}$ of formula (a) independently have a molecular weight ranging from and including 5 kDa to 50 kDa, in certain embodiments have a molecular weight ranging from and including 5 kDa to 40 kDa, in certain embodiments ranging from and including 7.5 kDa to 35 kDa, in certain embodiments ranging from and 7.5 to 30 kDa, in certain embodiments ranging from and including 10 to 30 kDa.

In certain embodiments, —$P^{a'}$, —$P^{a''}$ and —$P^{a'''}$ of formula (a) have a molecular weight of about 5 kDa. In certain embodiments, —$P^{a'}$, —$P^{a''}$ and —$P^{a'''}$ of formula (a) have a molecular weight of about 7.5 kDa. In certain embodiments, —$P^{a'}$, —$P^{a''}$ and —$P^{a'''}$ of formula (a) have a molecular weight of about 10 kDa. In certain embodiments, —$P^{a'}$, —$P^{a''}$ and —$P^{a'''}$ of formula (a) have a molecular weight of about 12.5 kDa. In another embodiment —$P^{a'}$, —$P^{a''}$ and —$P^{a'''}$ of formula (a) have a molecular weight of about 15 kDa. In certain embodiments, —$P^{a'}$, —$P^{a''}$ and —$P^{a'''}$ of formula (a) have a molecular weight of about 20 kDa.

In certain embodiments, —Z comprises one moiety of formula (a). In certain embodiments, —Z comprises two moieties of formula (a). In certain embodiments, —Z comprises three moieties of formula (a). In certain embodiments, —Z is a moiety of formula (a).

In certain embodiments, —Z comprises a moiety of formula (b):

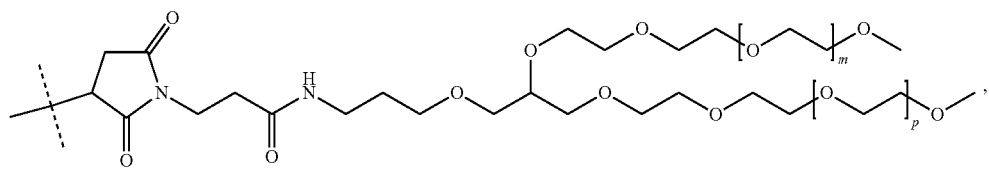
(b)

wherein
the dashed line indicates attachment to -L²- or to the remainder of —Z; and
m and p are independently of each other an integer ranging from and including 150 to 1000; in certain embodiments, an integer ranging from and including 150 to 500;
in certain embodiments, an integer ranging from and including 200 to 500; and in certain embodiments, an integer ranging from and including 400 to 500.

In certain embodiments, m and p of formula (b) are the same integer. In certain embodiments, m and p of formula (b) are about 450.

In certain embodiments, —Z is a moiety of formula (b).

In certain embodiments, the total mass of the PTH conjugate is at least 10 kDa, such as at least 12 kDa, such as at least 15 kDa, such as at least 20 kDa or such as at least 30 kDa. In certain embodiments, the total mass of the PTH conjugate is at most 250 kDa, such as at most 200 kDa, 180 kDa, 150 kDa or 100 kDa.

In certain embodiments, the PTH conjugate is of formula (IIe-i):

(IIe-i)

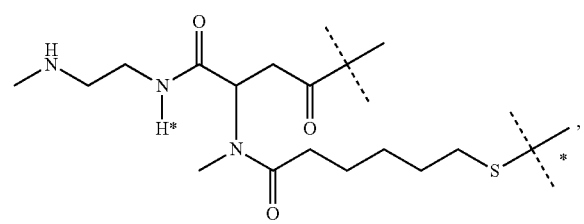

wherein
the unmarked dashed line indicates the attachment to a nitrogen of -D which is a PTH moiety by forming an amide bond; and
the dashed line marked with the asterisk indicates attachment to a moiety

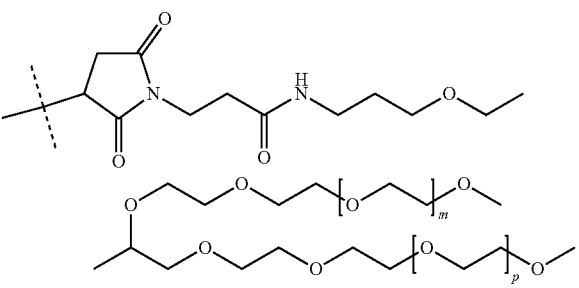

wherein
m and p are independently an integer ranging from and including 400 to 500.

In certain embodiments, -D is attached to the PTH conjugate of formula (IIe-i) through the N-terminal amine functional group of the PTH moiety.

In certain embodiments, the PTH conjugate is of formula (IIf-i):

(IIf-i)

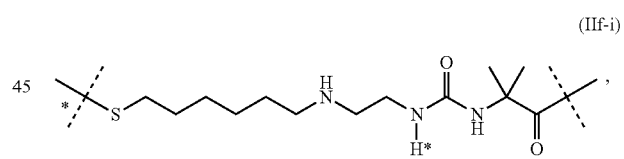

wherein
the unmarked dashed line indicates the attachment to a nitrogen of -D which is a PTH moiety by forming an amide bond; and
the dashed line marked with the asterisk indicates attachment to a moiety

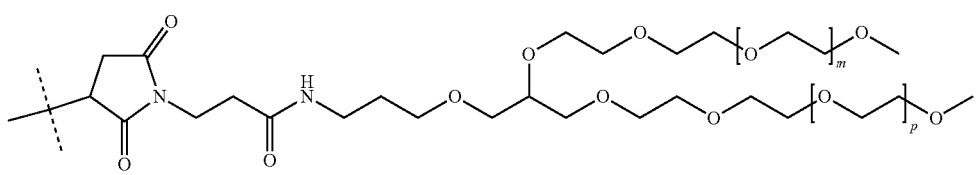

wherein
m and p are independently an integer ranging from and including 400 to 500.

In certain embodiments, -D is attached to the PTH conjugate of formula (IIf-i) through the N-terminal amine functional group of the PTH moiety.

In certain embodiments, the liquid pharmaceutical formulation of the present invention may comprise one or more further excipients, such as for example, stabilizers, anti-adsorption agents, viscosity modifiers and antibiotics. In certain embodiments, one excipient may have multiple, such as dual or triple functions.

In certain embodiments, the liquid pharmaceutical formulation of the present invention may further comprise a stabilizer, such as a stabilizer selected from the group consisting of alanine; arginine; aspartic acid; glycine; histidine; lysine; proline; sugars such as glucose, sucrose, and trehalose; polyols such as glycerol and sorbitol; salts such as potassium phosphate and sodium sulphate; chelating agents such as EDTA and hexaphosphate; ligands such as divalent metal ions; other salts or organic molecules such as phenolic derivatives; oligomers or polymers such as cyclodextrins, dextran, dendrimers, PEG, PVP, protamine and HSA. It is understood that a sugar may have more than one function, such as being an isotonicity agent and a stabilizer.

In certain embodiments, the liquid pharmaceutical formulation of the present invention may further comprise an anti-adsorption agent, such as an anti-adsoption agent selected from the group consisting of mainly ionic or non-ionic surfactants or other proteins or soluble polymers that are used to coat or adsorb competitively to the inner surface of the formulation or formulation's container such as poloxamer (Pluronic F-68), PEG dodecyl ether (Brij 35), polysorbate 20 and 80, dextran, polyethylene glycol, PEG-polyhistidine, BSA, HSA and gelatines. Chosen concentration and type of excipient depend on the effect to be avoided but typically a monolayer of surfactant is formed at the interface just above the CMC value.

It was surprisingly found that within the liquid pharmaceutical formulation of the present invention no oxidation on methionine residues of the PTH moiety was observed for at least 6 months, eliminating the need of an antioxidant. Accordingly, in certain embodiments, the liquid pharmaceutical formulation comprises no antioxidant.

In certain embodiments, the liquid pharmaceutical formulation of the present invention comprises a PTH conjugate, succinic acid, mannitol, m-cresol and optionally an antioxidant.

In certain embodiments, the liquid pharmaceutical formulation comprises

| | |
|---|---|
| PTH conjugate, of which PTH moiety | 0.05-5.0 mg/ml |
| succinic acid | 0.25-24 mg/ml |
| D-mannitol | 10-200 mg/ml |
| m-cresol | 1-10 mg/ml | and wherein the pH ranges from 3.0 to 6.0.

In certain embodiments, the liquid pharmaceutical formulation comprises

| | |
|---|---|
| PTH conjugate, of which PTH moiety | 0.05-5.0 mg/ml |
| succinic acid | 0.25-24 mg/ml |
| D-mannitol | 10-200 mg/ml |
| m-cresol | 1-10 mg/ml | and wherein the pH ranges from 3.5 to 5.0.

In certain embodiments, the liquid pharmaceutical formulation comprises

| | |
|---|---|
| PTH conjugate, of which PTH moiety | 0.05-5.0 mg/ml |
| succinic acid | 0.25-24 mg/ml |
| D-mannitol | 10-200 mg/ml |
| m-cresol | 1-10 mg/ml | and wherein the pH ranges from 3.7 to 4.3.

In certain embodiments, the liquid pharmaceutical formulation comprises

| | |
|---|---|
| PTH conjugate, of which PTH moiety | 0.1-5.0 mg/ml |
| succinic acid | 0.25-24 mg/ml |
| D-mannitol | 10-200 mg/ml |
| m-cresol | 1-10 mg/ml | and wherein the pH ranges from 3.0 to 6.0.

In certain embodiments, the liquid pharmaceutical formulation comprises

| | |
|---|---|
| PTH conjugate, of which PTH moiety | 0.1-5.0 mg/ml |
| succinic acid | 0.25-24 mg/ml |
| D-mannitol | 10-200 mg/ml |
| m-cresol | 1-10 mg/ml | and wherein the pH ranges from 3.5 to 5.0.

In certain embodiments, the liquid pharmaceutical formulation comprises

| | |
|---|---|
| PTH conjugate, of which PTH moiety | 0.1-5.0 mg/ml |
| succinic acid | 0.25-24 mg/ml |
| D-mannitol | 10-200 mg/ml |
| m-cresol | 1-10 mg/ml | and wherein the pH ranges from 3.7 to 4.3.

In certain embodiments, the liquid pharmaceutical formulation comprises

| | |
|---|---|
| PTH conjugate, of which PTH moiety | 0.1-1.5 mg/ml |
| succinic acid | 0.6-6.0 mg/ml |
| D-mannitol | 30-60 mg/ml |
| m-cresol | 1.5-3.5 mg/ml | and wherein the pH ranges from 3.0 to 6.0.

In certain embodiments, the liquid pharmaceutical formulation comprises

| | |
|---|---|
| PTH conjugate, of which PTH moiety | 0.1-1.5 mg/ml |
| succinic acid | 0.6-6.0 mg/ml |
| D-mannitol | 30-60 mg/ml |
| m-cresol | 1.5-3.5 mg/ml | and wherein the pH ranges from 3.5 to 5.0.

In certain embodiments, the liquid pharmaceutical formulation comprises

| | |
|---|---|
| PTH conjugate, of which PTH moiety | 0.1-1.5 mg/ml |
| succinic acid | 0.6-6.0 mg/ml |
| D-mannitol | 30-60 mg/ml |
| m-cresol | 1.5-3.5 mg/ml | and wherein the pH ranges from 3.7 to 4.3.

In certain embodiments, the liquid pharmaceutical formulation comprises

| | |
|---|---|
| PTH conjugate, of which PTH moiety | 0.25-0.35 mg/ml |
| succinic acid | 1.0-1.4 mg/ml |
| D-mannitol | 36-48 mg/ml |
| m-cresol | 2.0-3.0 mg/ml | and wherein the pH ranges from 3.0 to 6.0.

In certain embodiments, the liquid pharmaceutical formulation comprises

| | |
|---|---|
| PTH conjugate, of which PTH moiety | 0.25-0.35 mg/ml |
| succinic acid | 1.0-1.4 mg/ml |
| D-mannitol | 36-48 mg/ml |
| m-cresol | 2.0-3.0 mg/ml | and wherein the pH ranges from 3.5 to 5.0.

In certain embodiments, the liquid pharmaceutical formulation comprises

| | |
|---|---|
| PTH conjugate, of which PTH moiety | 0.25-0.35 mg/ml |
| succinic acid | 1.0-1.4 mg/ml |
| D-mannitol | 36-48 mg/ml |
| m-cresol | 2.0-3.0 mg/ml | and wherein the pH ranges from 3.7 to 4.3.

In certain embodiments, the liquid pharmaceutical formulation comprises

| | |
|---|---|
| PTH conjugate, of which PTH moiety | about 0.15 mg/ml |
| succinic acid | 1.0-3.0 mg/ml |
| D-mannitol | 33-51 mg/ml |
| m-cresol | 1.0-3.0 mg/ml | and wherein the pH ranges from 3.0 to 6.0.

In certain embodiments, the liquid pharmaceutical formulation comprises

| | |
|---|---|
| PTH conjugate, of which PTH moiety | 0.15 mg/ml |
| succinic acid | 1.0-3.0 mg/ml |
| D-mannitol | 33-51 mg/ml |
| m-cresol | 1.0-3.0 mg/ml | and wherein the pH ranges from 3.0 to 6.0.

In certain embodiments, the liquid pharmaceutical formulation according to the present invention comprises a PTH conjugate which comprises about 0.3 mg/ml PTH moiety, about 1.18 mg/ml succinic acid, about 41.7 mg/ml D-mannitol, about 2.5 mg/ml m-cresol and wherein the pH is about 4.0.

In certain embodiments, the liquid pharmaceutical formulation according to the present invention comprises a PTH conjugate which comprises 0.3 mg/ml PTH moiety, 1.2 mg/ml succinic acid, 42 mg/ml D-mannitol, 3 mg/ml m-cresol and wherein the pH is 4.

In certain embodiments, the liquid pharmaceutical formulation according to the present invention comprises a PTH conjugate which comprises 0.3 mg/ml PTH moiety, 1.18 mg/ml succinic acid, 41.7 mg/ml D-mannitol, 2.5 mg/ml m-cresol and wherein the pH is 4.0.

It is recognized by one of ordinary skill in the art that the liquid pharmaceutical formulation of the present invention may comprise a pH-adjusting agent.

In certain embodiments, the liquid pharmaceutical formulation according to the present invention comprises a PTH conjugate which comprises about 0.3 mg/ml PTH moiety, about 1.18 mg/ml succinic acid, about 41.7 mg/ml D-mannitol, about 2.5 mg/ml m-cresol, about 3.5 mg/ml of a 1.0 N sodium hydroxide and has a pH of about 4.0.

In certain embodiments, the liquid pharmaceutical formulation according to the present invention comprises a PTH conjugate which comprises 0.3 mg/ml PTH moiety, 1.2 mg/ml succinic acid, 42 mg/ml D-mannitol, 3 mg/ml m-cresol, 4 mg/ml of a 1.0 N sodium hydroxide and has a pH of 4.

In certain embodiments, the liquid pharmaceutical formulation according to the present invention comprises a PTH conjugate which comprises 0.3 mg/ml PTH moiety, 1.18 mg/ml succinic acid, 41.7 mg/ml D-mannitol, 2.5 mg/ml m-cresol, 3.5 mg/ml of a 1.0 N sodium hydroxide and has a pH of 4.0.

The liquid pharmaceutical formulation as described above is a liquid pharmaceutical formulation that is stable for at least 6 months, such as for at least 7 months, such as for at least 8 months, such as for at least 9 months, such as for at least 10 months, such as for at least 11 months, such as for at least 12 months. In certain embodiments, the liquid pharmaceutical formulation is stable for at least 14 months, such as for at least 16 months, such as for at least 18 months, such as for at least 20 months, such as for at least 22 months, such as for at least 24 months, such as for at least 36 months.

In certain embodiments, the liquid pharmaceutical formulation as described above is stored at temperatures ranging from −80° C. up to 25° C., such as from −20° C. up to 25° C., such as from −15° C. up to 25° C., such as from −10° C. up to 25° C., such as from −5° C. up to 25° C., such as from 0° C. up to 25° C., such as from 2° C. to 8° C. In certain embodiments, the liquid pharmaceutical formulation is stored at 2° C. In certain embodiments, the liquid pharmaceutical formulation is stored at 4° C. In certain embodiments, the liquid pharmaceutical formulation is stored at 5° C. In certain embodiments, the liquid pharmaceutical formulation is stored at 8° C. In certain embodiments, the liquid pharmaceutical formulation is stored at 10° C. In certain embodiments, the liquid pharmaceutical formulation is stored at 16° C. In certain embodiments, the liquid pharmaceutical formulation is stored at 20° C. In certain embodiments, the liquid pharmaceutical formulation is stored at 25° C. In certain embodiments, the liquid pharmaceutical formulation is stored at 30° C. In certain embodiments, the liquid pharmaceutical formulation is stored at 40° C.

In certain embodiments, the liquid pharmaceutical formulation is stable for at least 36 months, when stored at 2° C. to 8° C. In certain embodiments, the liquid pharmaceutical formulation is stable for at least 36 months, when stored at 2° C. In certain embodiments, the liquid pharmaceutical formulation is stable for at least 6 months, when stored at 5° C. In certain embodiments, the liquid pharmaceutical formulation is stable for at least 2 weeks when stored at 30° C.

Applicant surprisingly found that within the liquid pharmaceutical formulation of the present invention the reversible linkage between PTH and the water-soluble carrier is stable, eliminating the need of lyophilization and reconstitution from a lyophilizate. However, if desired, the liquid pharmaceutical formulation of the present invention may be dried, such as by lyophilization, to form a dried, such as a freeze-dried pharmaceutical formulation.

In certain embodiments, the method of manufacturing a liquid pharmaceutical formulation according to the present invention comprises the steps of:

(i) admixing the PTH conjugate with at least a buffering agent, an isotonicity agent, a preservative and optionally an antioxidant;
(ii) adjusting the pH of the admixture of step (i);
(iii) optionally, filtering the admixture from step (ii);
(iv) transferring amounts of the admixture from step (ii) or (iii) equivalent to the desired number of dosages into a container;
(v) sealing the container; and
wherein the order of steps (ii) and (iii) may optionally be reversed.

In certain embodiments, steps (ii) and (iii) are not reversed.

In certain embodiments, the PTH conjugate in step (i) is admixed with a buffering agent, an isotonicity agent, a preservative and optionally an antioxidant.

In certain embodiments, the method of manufacturing a liquid pharmaceutical formulation according to the present invention comprises the steps of:
(i) admixing the PTH conjugate with at least succinic acid, mannitol, m-cresol and optionally an antioxidant;
(ii) adjusting the pH of the admixture of step (i);
(iii) optionally, filtering the admixture from step (ii);
(iv) transferring amounts of the admixture from step (ii) or (iii) equivalent to the desired number of dosages into a container;
(v) sealing the container; and wherein the order of steps (ii) and (iii) may optionally be reversed.

In certain embodiments, steps (ii) and (iii) are not reversed.

In certain embodiments, the PTH conjugate in step (i) is admixed with succinic acid, mannitol, m-cresol and optionally an antioxidant.

In certain embodiments, the method of manufacturing a liquid pharmaceutical formulation according to the present invention comprises the steps of:
(i) admixing the PTH conjugate with at least succinic acid, mannitol, m-cresol and optionally an antioxidant to yield a formulation comprising:

| PTH conjugate, of which PTH moiety | 0.05-5.0 mg/ml |
| succinic acid | 0.25-24 mg/ml |
| D-mannitol | 10-200 mg/ml |
| m-cresol | 1-10 mg/ml |

(ii) adjusting the pH of the admixture of step (i) to a pH ranging from pH 3.0 to pH 6.0 with NaOH and HCl;
(iii) optionally, filtering the admixture from step (ii);
(iv) transferring amounts of the admixture from step (ii) or (iii) equivalent to the desired number of dosages into a container;
(v) sealing the container; and
wherein the order of steps (ii) and (iii) may optionally be reversed.

In certain embodiments, steps (ii) and (iii) are not reversed.

In certain embodiments, the PTH conjugate in step (i) is admixed with succinic acid, mannitol and m-cresol to yield a formulation comprising:

| PTH conjugate, of which PTH moiety | 0.05-5.0 mg/ml |
| succinic acid | 0.25-24 mg/ml |
| D-mannitol | 10-200 mg/ml |
| m-cresol | 1-10 mg/ml. |

In certain embodiments, in step (ii) the pH is adjusted to a pH ranging from pH 3.5 to pH 5.0. In certain embodiments, in step (ii) the pH is adjusted to a pH ranging from pH 3.7 to pH 4.3.

In certain embodiments, the method of manufacturing a liquid pharmaceutical formulation according to the present invention comprises the steps of:
(i) admixing the PTH conjugate with at least succinic acid, mannitol, m-cresol, optionally an antioxidant to yield a formulation comprising:

| PTH conjugate, of which PTH moiety | 0.10-5.0 mg/ml |
| succinic acid | 0.25-24 mg/ml |
| D-mannitol | 10-200 mg/ml |
| m-cresol | 1-10 mg/ml |

(ii) adjusting the pH of the admixture of step (i) to a pH ranging from pH 3.0 to pH 6.0 with NaOH and HCl;
(iii) optionally, filtering the admixture from step (ii);
(vi) transferring amounts of the admixture from step (ii) or (iii) equivalent to the desired number of dosages into a container;
(vii) sealing the container; and
wherein the order of steps (ii) and (iii) may optionally be reversed.

In certain embodiments, steps (ii) and (iii) are not reversed.

In certain embodiments the PTH conjugate in step (i) is mixed with succinic acid, mannitol and m-cresol to yield a formulation comprising:

| PTH conjugate, of which PTH moiety | 0.10-5.0 mg/ml |
| succinic acid | 0.25-24 mg/ml |
| D-mannitol | 10-200 mg/ml |
| m-cresol | 1-10 mg/ml. |

In certain embodiments, in step (ii) the pH is adjusted to a pH ranging from pH 3.5 to pH 5.0. In certain embodiments, in step (ii) the pH is adjusted to a pH ranging from pH 3.7 to pH 4.3.

In certain embodiments, the method of manufacturing a liquid pharmaceutical formulation according to the present invention comprises the steps of
(i) admixing the PTH conjugate with at least succinic acid, mannitol, m-cresol and optionally an antioxidant to yield a formulation comprising:

| PTH conjugate, of which PTH moiety | 0.10-1.5 mg/ml |
| succinic acid | 0.6-6 mg/ml |
| D-mannitol | 30-60 mg/ml |
| m-cresol | 1.5-3.5 mg/ml |

(ii) adjusting the pH of the admixture of step (i) to a pH ranging from pH 3.0 to pH 6.0 with NaOH and HCl;
(iii) optionally, filtering the admixture from step (ii);
(iv) transferring amounts of the admixture from step (ii) or (iii) equivalent to the desired number of dosages into a container;
(v) sealing the container; and
wherein the order of steps (ii) and (iii) may optionally be reversed.

In certain embodiments, steps (ii) and (iii) are not reversed.

In certain embodiments the PTH conjugate in step (i) is admixed with succinic acid, mannitol and m-cresol to yield a formulation comprising:

| PTH conjugate, of which PTH moiety | 0.10-1.5 mg/ml |
| succinic acid | 0.6-6 mg/ml |
| D-mannitol | 30-60 mg/ml |
| m-cresol | 1.5-3.5 mg/ml. |

In certain embodiments, in step (ii) the pH is adjusted to a pH ranging from pH 3.5 to pH 5.0. In certain embodiments, in step (ii) the pH is adjusted to a pH ranging from pH 3.7 to pH 4.3.

In certain embodiments, the method of manufacturing a liquid pharmaceutical formulation according to the present invention comprises the steps of
(i) admixing the PTH conjugate with at least succinic acid, mannitol, m-cresol and optionally an antioxidant to yield a formulation comprising:

| PTH conjugate, of which PTH moiety | 0.25-0.35 mg/ml |
| succinic acid | 1.0-1.4 mg/ml |
| D-mannitol | 36-48 mg/ml |
| m-cresol | 2.0-3.0 mg/ml |

(ii) adjusting the pH of the admixture of step (i) to a pH ranging from pH 3.0 to pH 6.0 with NaOH and HCl;
(iii) optionally, filtering the admixture from step (ii);
(iv) transferring amounts of the admixture from step (ii) or (iii) equivalent to the desired number of dosages into a container;
(v) sealing the container; and
wherein the order of steps (ii) and (iii) may optionally be reversed.

In certain embodiments, steps (ii) and (iii) are not reversed.

In certain embodiments the PTH conjugate in step (i) is mixed with succinic acid, mannitol and m-cresol to yield a formulation comprising:

| PTH conjugate, of which PTH moiety | 0.25-0.35 mg/ml |
| succinic acid | 1.0-1.4 mg/ml |
| D-mannitol | 36-48 mg/ml |
| m-cresol | 2.0-3.0 mg/ml. |

In certain embodiments, in step (ii) the pH is adjusted to a pH ranging from pH 3.5 to pH 5.0. In certain embodiments, in step (ii) the pH is adjusted to a pH ranging from pH 3.7 to pH 4.3.

In certain embodiments, the method of manufacturing a liquid pharmaceutical formulation according to the present invention comprises the steps of
(i) admixing the PTH conjugate with at least succinic acid, mannitol, m-cresol and optionally an antioxidant to yield a formulation comprising:

| PTH conjugate, of which PTH moiety | about 0.15 mg/ml |
| succinic acid | 1.0-3.0 mg/ml |
| D-mannitol | 33-51 mg/ml |
| m-cresol | 1.0-3.0 mg/ml |

(ii) adjusting the pH of the admixture of step (i) to a pH ranging from pH 3.0 to pH 6.0 with NaOH and HCl;
(iii) optionally, filtering the admixture from step (ii);
(iv) transferring amounts of the admixture from step (ii) or (iii) equivalent to the desired number of dosages into a container;
(v) sealing the container; and
wherein the order of steps (ii) and (iii) may optionally be reversed.

In certain embodiments, steps (ii) and (iii) are not reversed.

In certain embodiments the PTH conjugate in step (i) is admixed with succinic acid, mannitol and m-cresol to yield a formulation comprising:

| PTH conjugate, of which PTH moiety | 0.15 mg/ml |
| succinic acid | 1.0-3.0 mg/ml |
| D-mannitol | 33-51 mg/ml |
| m-cresol | 1.0-3.0 mg/ml. |

In certain embodiments, in step (ii) the pH is adjusted to a pH ranging from pH 3.5 to pH 5.0. In certain embodiments, in step (ii) the pH is adjusted to a pH ranging from pH 3.7 to pH 4.3.

In certain embodiments, the method of manufacturing a liquid pharmaceutical formulation according to the present invention comprises the steps of
(i) admixing the PTH conjugate with at least succinic acid, mannitol, m-cresol and optionally an antioxidant to yield a formulation comprising

| PTH conjugate, of which PTH moiety | 0.30 mg/ml |
| succinic acid | 1.18 mg/ml |
| D-mannitol | 41.7 mg/ml |
| m-cresol | 2.5 mg/ml |

(ii) adjusting the pH of the admixture of step (i) to a pH of about 4 with NaOH and HCl;
(iii) optionally, filtering the admixture from step (ii);
(iv) transferring amounts of the admixture from step (ii) or (iii) equivalent to the desired number of dosages into a container;
(v) sealing the container; and
wherein the order of steps (ii) and (iii) may optionally be reversed.

In certain embodiments, steps (ii) and (iii) are not reversed.

In certain embodiments the PTH conjugate in step (i) is admixed with succinic acid, mannitol and m-cresol to yield a formulation comprising:

| PTH conjugate, of which PTH moiety | 0.30 mg/ml |
| succinic acid | 1.18 mg/ml |
| D-mannitol | 41.7 mg/ml |
| m-cresol | 2.5 mg/ml. |

In certain embodiments, the pH of the formulation of step (i) is adjusted to a pH of 4.

Another aspect of the present invention refers to a container comprising the liquid pharmaceutical formulation of the present invention.

In certain embodiments, the container may be selected from the group consisting of vial; syringe, such as dual-chamber syringe; ampoule and cartridge, such as dual-chamber cartridge.

In certain embodiments, the cartridge is for use with a pen injector, such as an auto-injector.

In certain embodiments, the liquid pharmaceutical formulation of the present invention is provided as a single dose, meaning that the container comprising the liquid pharmaceutical formulation comprises one therapeutic dose.

In certain embodiments, the liquid pharmaceutical formulation comprises multiple doses, meaning that the container comprising the liquid pharmaceutical formulation contains more than one therapeutic dose.

In certain embodiments, a multiple dose liquid pharmaceutical formulation comprises at least 2 doses, such as at least 4 doses, such as at least 6 doses, such as at least 8 doses, such as at least 10 doses, such as at least 12 doses of PTH conjugate and in certain embodiments such as at least 14 doses.

In certain embodiments, a multiple dose liquid pharmaceutical formulation comprises at least 2, 4, 6, 8, 10, 12 or 14 doses of PTH conjugate.

Thus, in another aspect of the present invention the liquid pharmaceutical formulation is provided as a multiple dose formulation.

Another aspect of the present invention is the liquid pharmaceutical formulation of the present invention for use as a medicament.

In another aspect, the present invention relates to the liquid pharmaceutical formulations of the present invention for use in the treatment, control, delay or prevention of one or more diseases which can be treated, controlled, delayed or prevented with PTH.

In certain embodiments, the present invention relates to the liquid pharmaceutical formulations of the present invention for use in the treatment of one or more diseases which can be treated with PTH.

A further aspect of the present invention is a method of treating, controlling, delaying or preventing in a patient one or more diseases which can be treated by PTH, the method comprising administering to the patient a therapeutically effective amount of the liquid pharmaceutical formulation of the present invention.

In certain embodiments, said one or more diseases which can be treated, controlled, delayed or prevented with PTH are selected from the group consisting of hypoparathyroidism, hyperphosphatemia, osteoporosis, fracture repair, osteomalacia, osteomalacia and osteoporosis in patients with hypophosphatasia, steroid-induced osteoporosis, male osteoporosis, arthritis, osteoarthritis, osteogenesis imperfecta, fibrous dysplasia, rheumatoid arthritis, Paget's disease, humoral hypercalcemia associated with malignancy, osteopenia, periodontal disease, bone fracture, alopecia, chemotherapy-induced alopecia and thrombocytopenia.

In certain embodiments, said one or more diseases which can be treated, controlled, delayed or prevented with PTH are selected from the group consisting of hypoparathyroidism, hyperphosphatemia, osteoporosis, fracture repair, osteomalacia, osteomalacia and osteoporosis in patients with hypophosphatasia, steroid-induced osteoporosis, male osteoporosis, arthritis, osteoarthritis, osteogenesis imperfecta, fibrous dysplasia, rheumatoid arthritis, Paget's disease, humoral hypercalcemia associated with malignancy, osteopenia, periodontal disease, bone fracture, alopecia, chemotherapy-induced alopecia and thrombocytopenia, chronic periodontitis, osteonecrosis of jaw and poorly healing fractures due to ALPL gene mutations.

In certain embodiments, said disease is hypoparathyroidism.

In certain embodiments, said disease is hypoparathyroidism induced by immune checkpoint inhibitor treatment.

In certain embodiments, said disease is hypoparathyroidism induced by immune checkpoint inhibitor treatment targeting CTLA-4 (cytotoxic T-lymphocyte-associated protein 4), PD-1 (programmed cell death protein 1), PD-L1 (programmed death-ligand 1), PD-L2 (programmed death-ligand 2), KIR (killer-cell immunoglobulin-like receptor), B7-H3, B7-H4, BTLA (B- and T-lymphocyte attenuator), LAG3 (lymphocyte-activation gene 3), TIM-3 (T-cell immunoglobulin and mucin-domain containing-3), VISTA (V-domain Ig suppressor of T cell activation), ILT2/LILRB1 (Ig-like transcript 2/leukocyte Ig-like receptor 1), ILT3/LILRB4 (Ig-like transcript 3/leukocyte Ig-like receptor 4), ILT4/LILRB2 (Ig-like transcript 4/leukocyte Ig-like receptor 2), TIGIT (T cell immunoreceptor with Ig and ITIM domains), NKG2A, PVRIG or combinations thereof.

In certain embodiments, said disease is hypoparathyroidism induced by immune checkpoint inhibitor treatment targeting CTLA-4, PD-1, PD-L1 or combinations thereof.

In certain embodiments, said disease is hypoparathyroidism induced by immune checkpoint inhibitor treatment targeting CTLA-4 with immune checkpoint inhibitors such as ipilimumab, tremelimumab, MK-1308, FPT155, PRS010, BMS-986249, BPI-002, CBT509, JS007, ONC392, TE1254, IBI310, BR02001, CG0161, KN044, PBI5D3H5, BCD145, ADU1604, AGEN1884, AGEN1181, CS1002 or CP675206.

In certain embodiments, said disease is hypoparathyroidism induced by immune checkpoint inhibitor treatment targeting PD-1 with immune checkpoint inhibitors such as pembrolizumab, nivolumab, pidilizumab, AMP-224, BMS-936559, cemiplimab or PDR001.

In certain embodiments, said disease is hypoparathyroidism induced by immune checkpoint inhibitor treatment targeting PD-L1 with immune checkpoint inhibitors such as MDX-1105, MEDI4736, atezolizumab, avelumab, BMS-936559 or durvalumab.

In certain embodiments, said disease is hypoparathyroidism induced by immune checkpoint inhibitor treatment targeting PD-L2.

In certain embodiments, said disease is hypoparathyroidism induced by immune checkpoint inhibitor treatment targeting KIR with immune checkpoint inhibitors such as lirilumab (IPH2102) or IPH2101.

In certain embodiments, said disease is hypoparathyroidism induced by immune checkpoint inhibitor treatment targeting B7-H3 with immune checkpoint inhibitors such as MGA271.

In certain embodiments, said disease is hypoparathyroidism induced by immune checkpoint inhibitor treatment targeting B7-H4 with immune checkpoint inhibitors such as FPA150.

In certain embodiments, said disease is hypoparathyroidism induced by immune checkpoint inhibitor treatment targeting BTLA.

In certain embodiments, said disease is hypoparathyroidism induced by immune checkpoint inhibitor treatment targeting LAG3 with immune checkpoint inhibitors such as IMP321 (eftilagimod alpha), relatlimab, MK-4280, AVA017, BI754111, ENUM006, GSK2831781, INCAGN2385, LAG3Ig, LAG525, REGN3767, Sym016, Sym022, TSR033, TSR075 or XmAb22841.

In certain embodiments, said disease is hypoparathyroidism induced by immune checkpoint inhibitor treatment targeting TIM-3 with immune checkpoint inhibitors such as LY3321367, MBG453 or TSR-022.

In certain embodiments, said disease is hypoparathyroidism induced by immune checkpoint inhibitor treatment targeting VISTA with immune checkpoint inhibitors such as JNJ-61610588.

In certain embodiments, said disease is hypoparathyroidism induced by immune checkpoint inhibitor treatment targeting ILT2/LILRB1.

In certain embodiments, said disease is hypoparathyroidism induced by immune checkpoint inhibitor treatment targeting ILT3/LILRB4.

In certain embodiments, said disease is hypoparathyroidism induced by immune checkpoint inhibitor treatment targeting ILT3/LILRB2 with immune checkpoint inhibitors such as MK-4830.

In certain embodiments, said disease is hypoparathyroidism induced by immune checkpoint inhibitor treatment targeting TIGIT with immune checkpoint inhibitors such as MK-7684, PTZ-201, RG6058 or COM902.

In certain embodiments, said disease is hypoparathyroidism induced by immune checkpoint inhibitor treatment targeting NKG2A with immune checkpoint inhibitors such as IPH-2201.

In certain embodiments, said disease is hypoparathyroidism induced by immune checkpoint inhibitor treatment targeting PVRIG with immune checkpoint inhibitors such as COM701.

In certain embodiments, said disease is hypoparathyroidism induced by immune checkpoint inhibitor treatment targeting both PD-1 and CTLA-4.

In certain embodiments, said disease is hypoparathyroidism induced by immune checkpoint inhibitor treatment with nivolumab.

In certain embodiments, said disease is hypoparathyroidism induced by immune checkpoint inhibitor treatment with ipilimumab.

In certain embodiments, said disease is hypoparathyroidism induced by immune checkpoint inhibitor treatment with pembrolizumab.

In certain embodiments, said disease is hypoparathyroidism induced by immune checkpoint inhibitor treatment with a combination of nivolumab and ipilimumab.

In certain embodiments, said disease is rheumatoid arthritis induced by immune checkpoint inhibitor treatment.

In certain embodiments, said disease is rheumatoid arthritis induced by immune checkpoint inhibitor treatment targeting PD-1 or PD-L1.

In certain embodiments, said disease is rheumatoid arthritis induced by immune checkpoint inhibitor treatment targeting PD-1.

In certain embodiments, said disease is rheumatoid arthritis induced by immune checkpoint inhibitor treatment targeting PD-L1.

In certain embodiments, said disease is rheumatoid arthritis induced by immune checkpoint inhibitor treatment with nivolumab.

In certain embodiments, said disease is rheumatoid arthritis induced by immune checkpoint inhibitor treatment with pembrolizumab.

In certain embodiments, said disease is rheumatoid arthritis induced by immune checkpoint inhibitor treatment with a combination of nivolumab and ipilimumab.

In certain embodiments, said disease is rheumatoid arthritis which recursed after immune checkpoint inhibitor treatment.

The liquid pharmaceutical formulation of the present invention may be administered for example via topical, enteral or parenteral administration and by methods of external application, injection or infusion, including intraarticular, periarticular, intradermal, subcutaneous, intramuscular, intravenous, intraosseous, intraperitoneal, intrathecal, intracapsular, intraorbital, intravitreal, intratympanic, intravesical, intracardiac, transtracheal, subcuticular, subcapsular, subarachnoid, intraspinal, intraventricular, intrasternal injection, infusion, intranasal, oral, transpulmonary and transdermal administration, direct delivery to the brain via implanted device allowing delivery of the invention or the like to brain tissue or brain fluids (e.g., Ommaya Reservoir), direct intracerebroventricular injection or infusion, injection or infusion into brain or brain associated regions, injection into the subchoroidal space, retro-orbital injection and ocular instillation, preferably via subcutaneous injection.

In certain embodiments, the liquid pharmaceutical formulation of the present invention is administered via subcutaneous injection.

In certain embodiments, the liquid pharmaceutical formulation of the present invention is administered via subcutaneous injection with a syringe and needle or a pen injector, such as an auto-injector.

In certain embodiments, the liquid pharmaceutical formulation of the present invention is administered via subcutaneous injection with a syringe and needle.

In certain embodiments, the liquid pharmaceutical formulation of the present invention is administered via subcutaneous injection with a pen injector.

In certain embodiments, the liquid pharmaceutical formulation of the present invention is administered via subcutaneous injection with an auto-injector.

The time period between two consecutive subcutaneous administrations, i.e. the administration interval, is in certain embodiments at least every 12 hours, 24 hours, 36 hours, 48 hours, 60 hours, 72 hours, 84 hours, 96 hours, 108 hours, 120 hours, 132 hours, 144 hours, 156 hours, one week, two weeks, three weeks or four weeks.

In certain embodiments, the time period between two consecutive subcutaneous administrations is 12 hours. In certain embodiments, the time period between two consecutive subcutaneous administrations is 24 hours. In certain embodiments, the time period between two consecutive subcutaneous administrations is 48 hours. In certain embodiments, the time period between two consecutive subcutaneous administrations is 72 hours. In certain embodiments, the time period between two consecutive subcutaneous administrations is 96 hours. In certain embodiments, the time period between two consecutive subcutaneous administrations is 120 hours. In certain embodiments, the time period between two consecutive subcutaneous administrations is 144 hours. In certain embodiments, the time period between two consecutive subcutaneous administrations is one week.

EXAMPLES

Materials and Methods

All materials were commercially available except where stated otherwise.

For the preparation of the formulations excipient stock solutions were prepared. All excipients were mixed and filled up to 90% of the final volume with water, and a calculated amount of NaOH solution was spiked into the solution to reach the desired pH value of the final formulation after addition of compound 1. Subsequently, the appropriate amount of compound 1 was added and dissolved. After pH adjustment, the volume was adjusted to the final volume in volumetric flasks. The formulations were filtered through a 0.2-μm PVDF filter prior to filling.

Visual inspection: The cartridges were inspected for the presence or absence of visible particles under gentle, manual, radial agitation for 5 seconds in front of a white background and for 5 seconds in front of a black background according to the European Pharmacopoeia ($8^{th}$ edition; monograph 2.9.20). The inspection was performed independently by two trained examiners. To classify the observed visible particles, a number score on the basis of the "Deutscher Arzneimittel-Codex" (DAC 2006) was used.

pH: The pH of the formulations was measured at room temperature with a calibrated pH meter using a normal ionic strength electrode.

Osmolality: Osmolality of the samples was measured by the method of freezing-point depression.

Micro-Flow-Imaging: Micro-Flow Imaging measurements were conducted on an MFI-5200 particle analyzer system.

HP-SEC was used to determine the purity of compound 1: Samples were analyzed on a 10×300 mm column composed of cross-linked agarose and dextran of a grade suitable for fractionation of globular proteins of a molecular mass from 10 000 to 600 000 g/mol. The detection wavelength was at a wavelength of 215 nm.

RP-HPLC was used to detect free PTH and to determine the purity and content of compound 1: A C18 2.1×100 mm column with 130 Å pore size and 1.7 μm particle size was used. The detection was at a wavelength of 215 nm. The content was determined by measurement of a reference sample.

RP-HPLC analysis after in vitro release: The release of PTH from compound 1 was performed at pH 10.1 and 5° C. to minimize the peptide degradation. After 76 h incubation at 5° C., the release was stopped by addition of acetic acid. The resulting sample was subjected to RP-HPLC on a C18 2.1×100 mm column with 130 Å pore size and 1.7 μm particle size. The detection was at a wavelength of 215 nm.

Example 1

Synthesis of Compound 1

TABLE 1

|    | Compound 1 (mg PTH(1-34)/mL) | Succinic acid (mg/mL) | Mannitol (mg/mL) | m-cresol (mg/mL) | Base | pH |
|----|------|------|----|---|------|-----|
| F1 | 0.4  | 1.18 | 41 | 3 | NaOH | 4.0 |
| F2 | 0.4  | 1.18 | 41 | 3 | NaOH | 4.5 |
| F3 | 0.4  | 1.18 | 41 | 3 | NaOH | 5.0 |
| F4 | 0.4  | 1.18 | 41 | 3 | NaOH | 5.5 |

Formulations were filled in cartridges and incubated in incubators set at 5° C., 25° C./60% RH and 40° C./75% RH for up to 3 months. After 2 weeks, 1 month and 3 months, one cartridge per formulation and storage condition was removed and subjected to analysis. Table 2 shows the amount of the released free PTH over time for F1, F2, F3 and F4, as detected by RP-HPLC. It was observed that a higher amount of free PTH was released in the liquid pharmaceutical formulations with higher pH values.

TABLE 2

| | Free PTH/% of total integrated area for the free PTH(1-34) peak | | |
|---|---|---|---|
| | 5° C. | at 25° C., 60% RH | 40° C., 75% RH |
| F1 | n.d. (t = 0) | n.d. (t = 0) | n.d. (t = 0) |
|    | n.d. (t = 1 M) | 0.15 (t = 2 W) | 1.24 (t = 2 W) |
|    | n.d. (t = 3 M) | 0.29 (t = 1 M) | 2.28 (t = 1 M) |
|    |                | 0.82 (t = 3 M) | 5.58 (t = 3 M) |
| F2 | n.d. (t = 0) | n.d. (t = 0) | n.d. (t = 0) |
|    | n.d. (t = 1 M) | 0.26 (t = 2 W) | 2.52 (t = 2 W) |
|    | n.d. (t = 3 M) | 0.50 (t = 1 M) | 4.53 (t = 1 M) |
|    |                | 1.64 (t = 3 M) | 10.71 (t = 3 M) |
| F3 | n.d. (t = 0) | n.d. (t = 0) | n.d. (t = 0) |
|    | n.d. (t = 1 M) | 0.62 (t = 2 W) | 5.51 (t = 2 W) |
|    | 0.11 (t = 3 M) | 1.17 (t = 1 M) | 9.70 (t = 1 M) |
|    |                | 3.86 (t = 3 M) | 18.95 (t = 3 M) |
| F4 | n.d. (t = 0) | n.d. (t = 0) | n.d. (t = 0) |
|    | 0.10 (t = 1 M) | 1.35 (t = 2 W) | 11.28 (t = 2 W) |
|    | 0.26 (t = 3 M) | 2.67 (t = 1 M) | 18.49 (t = 1 M) |
|    |                | 8.30 (t = 3 M) | 25.78 (t = 3 M) | n.d. = below LOQ

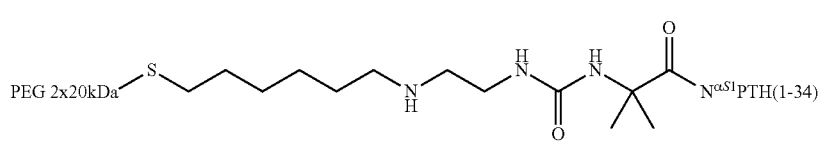

1

Compound 1 was synthesized as described in WO 2017/148883 A1 for conjugate 18.

Example 2

Stability Testing of Formulations Containing Compound 1

The influence of the pH value of the liquid pharmaceutical formulation on the amount of released PTH(1-34) from compound 1 was evaluated. For this purpose, four different formulations (F1, F2, F3 and F4) containing compound 1 were prepared (Table 1). Each formulation contained 0.4 mg PTH(1-34)/mL.

Next, the purity of the PTH(1-34) within F1, F2, F3 and F4 was evaluated. For this purpose, the liberation of PTH from compound 1 was induced at pH 10.1 and 5° C. After 76 h incubation at 5° C., the release was stopped by addition of acetic acid. The resulting sample was subjected to RP-HPLC analysis. Table 3 shows that the percentage of deamidated peptide species is more significant for the formulations with higher pH values, while the percentage of truncated peptide species, i.e. PTH(1-30) is more significant in the formulations with lower pH values. Overall, the highest peptide purity over time was observed for formulation F1 for samples incubated at 40° C./75% RH.

TABLE 3

Purity of free PTH(1-34) after liberation when stored at 40° C./75% RH

| | % of total integrated area for free PTH(1-34) peak | (% impurity) Deamidated forms | (% impurity) PTH(1-30) |
|---|---|---|---|
| F1 | 89.9 (t = 0) | 1.87 (t = 0) | 0.22 (t = 0) |
| | 86.1 (t = 2 W) | 4.55 (t = 2 W) | 1.94 (t = 2 W) |
| | 78.9 (t = 1 M) | 7.35 (t = 1 M) | 3.32 (t = 1 M) |
| | 59.2 (t = 3 M) | 16.18 (t = 3 M) | 8.61 (t = 3 M) |
| F2 | 89.4 (t = 0) | 1.92 (t = 0) | 0.45 (t = 0) |
| | 84.9 (t = 2 W) | 5.65 (t = 2 W) | 1.07 (t = 2 W) |
| | 78.4 (t = 1 M) | 8.83 (t = 1 M) | 1.92 (t = 1 M) |
| | 58.6 (t = 3 M) | 20.42 (t = 3 M) | 4.21 (t = 3 M) |
| F3 | 90.2 (t = 0) | 1.73 (t = 0) | 0.33 (t = 0) |
| | 83.6 (t = 2 W) | 7.45 (t = 2 W) | 0.61 (t = 2 W) |
| | 76.8 (t = 1 M) | 11.85 (t = 1 M) | 0.87 (t = 1 M) |
| | 53.1 (t = 3 M) | 27.70 (t = 3 M) | 1.53 (t = 3 M) |
| F4 | 90.5 (t = 0) | 1.57 (t = 0) | 0.30 (t = 0) |
| | 80.9 (t = 2 W) | 10.15 (t = 2 W) | 0.36 (t = 2 W) |
| | 71.6 (t = 1 M) | 16.91 (t = 1 M) | 0.48 (t = 1 M) |
| | 41.8 (t = 3 M) | 36.89 (t = 3 M) | 0.42 (t = 3 M) |

Example 3

Stability Towards Oxidation of Formulations Containing Compound 1

The effect of antioxidants and oxygen in the headspace (HS) on the stability of compound 1 and free PTH was investigated. Four different formulations (F5, F6, F7 and F8) comprising compound 1 at pH 4.0, wherein the concentration of antioxidant and HS volume was varied, were prepared (Table 4). Each formulation contained 0.4 mg PTH(1-34)/mL.

TABLE 4

| | Compound 1 (mg PTH(1-34)/mL) | Succinic acid (mg/mL) | Mannitol (mg/mL) | m-cresol (mg/mL) | L-methionine (mg/mL) | HS (μL) |
|---|---|---|---|---|---|---|
| F5 | 0.4 | 1.18 | 41 | 3 | — | — |
| F6 no HS | 0.4 | 1.18 | 41 | 3 | 0.1 | — |
| F6 low HS | 0.4 | 1.18 | 41 | 3 | 0.1 | 50 |
| F6 high HS | 0.4 | 1.18 | 41 | 3 | 0.1 | 200 |
| F7 no HS | 0.4 | 1.18 | 41 | 3 | 1.0 | — |
| F7 low HS | 0.4 | 1.18 | 41 | 3 | 1.0 | 50 |
| F7 high HS | 0.4 | 1.18 | 41 | 3 | 1.0 | 200 |
| F8 no HS | 0.4 | 1.18 | 41 | 3 | 1.5 | — |
| F8 low HS | 0.4 | 1.18 | 41 | 3 | 1.5 | 50 |
| F8 high HS | 0.4 | 1.18 | 41 | 3 | 1.5 | 200 |

Formulations were filled in cartridges with various headspaces (no HS, 50 μL HS, or 200 μL HS). The cartridges were incubated in incubators set at 5° C. and 25° C./60% RH for up to 6 months. After 2 weeks, 1 month, 3 months and 6 months one cartridge per formulation and storage condition was removed and subjected to RP-HPLC analysis.

Table 5 shows that for the formulations stored at 5° C., no free PTH was released over a period of 6 months. In the formulations stored at 25° C. approximately 0.9% free PTH was detected after 3 months.

TABLE 5

Free PTH/% of total integrated area for free PTH(1-34) peak

| | 2-8° C. | 25° C./60% RH |
|---|---|---|
| F5 | n.d. (t = 0) | 0.15 (t = 2 W) |
| | 0.16 (t = 2 W) | 0.30 (t = 1 M) |
| | n.d. (t = 1 M) | 0.86 (t = 3 M) |
| | n.d. (t = 3 M) | |
| | n.d. (t = 6 M) | |
| F6 no HS | n.d. (t = 0) | 0.17 (t = 2 W) |
| | 0.16 (t = 2 W) | 0.29 (t = 1 M) |
| | n.d. (t = 1 M) | 0.90 (t = 3 M) |
| | n.d. (t = 3 M) | |
| | n.d. (t = 6 M) | |
| F6 low HS | n.d. (t = 0) | 0.18 (t = 2 W) |
| | 0.17 (t = 2 W) | 0.31 (t = 1 M) |
| | n.d. (t = 1 M) | 0.91 (t = 3 M) |
| | n.d. (t = 3 M) | |
| | n.d. (t = 6 M) | |
| F6 high HS | n.d. (t = 0) | 0.14 (t = 2 W) |
| | 0.17 (t = 2 W) | 0.30 (t = 1 M) |
| | n.d. (t = 1 M) | 0.90 (t = 3 M) |
| | n.d. (t = 3 M) | |
| | n.d. (t = 6 M) | |
| F7 no HS | n.d. (t = 0) | 0.13 (t = 2 W) |
| | 0.17 (t = 2 W) | 0.31 (t = 1 M) |
| | n.d. (t = 1 M) | 0.88 (t = 3 M) |

TABLE 5-continued

Free PTH/% of total integrated area for free PTH(1-34) peak

| | 2-8° C. | 25° C./60% RH |
|---|---|---|
| | n.d. (t = 3 M) | |
| | n.d. (t = 6 M) | |
| F7 low HS | n.d. (t = 0) | 0.16 (t = 2 W) |
| | 0.17 (t = 2 W) | 0.31 (t = 1 M) |
| | n.d. (t = 1 M) | 0.89 (t = 3 M) |
| | n.d. (t = 3 M) | |
| | n.d. (t = 6 M) | |
| F7 high HS | n.d. (t = 0) | 0.16 (t = 2 W) |
| | 0.17 (t = 2 W) | 0.31 (t = 1 M) |
| | n.d. (t = 1 M) | 0.90 (t = 3 M) |
| | n.d. (t = 3 M) | |
| | n.d. (t = 6 M) | |
| F8 no HS | n.d. (t = 0) | 0.15 (t = 2 W) |
| | 0.16 (t = 2 W) | 0.29 (t = 1 M) |
| | n.d. (t = 1 M) | 0.80 (t = 3 M) |
| | n.d. (t = 3 M) | |
| | n.d. (t = 6 M) | |
| F8 low HS | n.d. (t = 0) | 0.12 (t = 2 W) |
| | 0.16 (t = 2 W) | 0.28 (t = 1 M) |
| | n.d. (t = 1 M) | 0.88 (t = 3 M) |
| | n.d. (t = 3 M) | |
| | n.d. (t = 6 M) | |
| F8 high HS | n.d. (t = 0) | 0.16 (t = 2 W) |
| | 0.15 (t = 2 W) | 0.29 (t = 1 M) |
| | n.d. (t = 1 M) | 0.87 (t = 3 M) |
| | n.d. (t = 3 M) | |
| | n.d. (t = 6 M) | | n.d. = below LOQ

After the liberation of PTH was induced from compound 1 (pH 10.1 and 5° C.) the resulting mixtures were subjected to RP-HPLC analyses. As shown in Table 6, the detected amount of oxidized species was unchanged for all formulations. Variations in the headspace volume and the concentration of antioxidant did not have a significant impact on the levels of oxidized species.

TABLE 6

Purity of free PTH (1-34) after liberation

| | 2-8° C. % of total integrated area for free PTH (1-34) peak | 2-8° C. (% impurity) Oxidation | 25° C./60% RH % of total integrated area for free PTH (1-34) peak | 25° C./60% RH (% impurity) Oxidation |
|---|---|---|---|---|
| F5 | 89.9 (t = 0) | 1.69 (t = 0) | 89.4 (t = 2 W) | 1.61 (t = 2 W) |
| | 89.8 (t = 2 W) | 1.56 (t = 2 W) | 87.6 (t = 1 M) | 1.65 (t = 1 M) |
| | 90.0 (t = 1 M) | 1.60 (t = 1 M) | 84.4 (t = 3 M) | 1.73 (t = 3 M) |
| | 89.6 (t = 3 M) | 1.64 (t = 3 M) | | |
| | 91.2 (t = 6 M) | 1.62 (t = 6 M) | | |
| F6 no HS | 90.4 (t = 0) | 1.74 (t = 0) | 88.7 (t = 2 W) | 1.72 (t = 2 W) |
| | 90.2 (t = 2 W) | 1.64 (t = 2 W) | 87.8 (t = 1 M) | 1.57 (t = 1 M) |
| | 89.7 (t = 1 M) | 1.72 (t = 1 M) | 83.8 (t = 3 M) | 1.79 (t = 3 M) |
| | 89.4 (t = 3 M) | 1.86 (t = 3 M) | | |
| | 91.7 (t = 6 M) | 1.69 (t = 6 M) | | |
| F6 low HS | 91.0 (t = 0) | 1.73 (t = 0) | 89.9 (t = 2 W) | 1.72 (t = 2 W) |
| | 89.2 (t = 2 W) | 1.72 (t = 2 W) | 88.7 (t = 1 M) | 1.69 (t = 1 M) |
| | 89.9 (t = 1 M) | 1.73 (t = 1 M) | 83.6 (t = 3 M) | 1.84 (t = 3 M) |
| | 89.5 (t = 3 M) | 1.71 (t = 3 M) | | |
| | 89.8 (t = 6 M) | 1.69 (t = 6 M) | | |
| F6 high HS | 90.6 (t = 0) | 1.78 (t = 0) | 88.0 (t = 2 W) | 1.69 (t = 2 W) |
| | 89.2 (t = 2 W) | 1.75 (t = 2 W) | 88.4 (t = 1 M) | 1.77 (t = 1 M) |
| | 88.9 (t = 1 M) | 1.66 (t = 1 M) | 84.7 (t = 3 M) | 1.73 (t = 3 M) |
| | 89.5 (t = 3 M) | 1.72 (t = 3 M) | | |
| | 90.2 (t = 6 M) | 1.78 (t = 6 M) | | |
| F7 no HS | 90.6 (t = 0) | 1.65 (t = 0) | 89.1 (t = 2 W) | 1.54 (t = 2 W) |
| | 89.4 (t = 2 W) | 1.52 (t = 2 W) | 88.8 (t = 1 M) | 1.57 (t = 1 M) |
| | 89.9 (t = 1 M) | 1.58 (t = 1 M) | 83.7 (t = 3 M) | 1.62 (t = 3 M) |
| | 89.7 (t = 3 M) | 1.59 (t = 3 M) | | |
| | 91.2 (t = 6 M) | 1.56 (t = 6 M) | | |
| F7 low HS | 90.2 (t = 0) | 1.72 (t = 0) | 89.3 (t = 2 W) | 1.53 (t = 2 W) |
| | 90.1 (t = 2 W) | 1.49 (t = 2 W) | 89.0 (t = 1 M) | 1.58 (t = 1 M) |
| | 89.3 (t = 1 M) | 1.48 (t = 1 M) | 83.9 (t = 3 M) | 1.62 (t = 3 M) |
| | 89.1 (t = 3 M) | 1.59 (t = 3 M) | | |
| | 90.6 (t = 6 M) | 1.59 (t = 6 M) | | |
| F7 high HS | 91.2 (t = 0) | 1.55 (t = 0) | 89.4 (t = 2 W) | 1.57 (t = 2 W) |
| | 89.5 (t = 2 W) | 1.55 (t = 2 W) | 89.2 (t = 1 M) | 1.50 (t = 1 M) |
| | 90.2 (t = 1 M) | 1.56 (t = 1 M) | 84.5 (t = 3 M) | 1.61 (t = 3 M) |
| | 89.7 (t = 3 M) | 1.59 (t = 3 M) | | |
| | 91.1 (t = 6 M) | 1.53 (t = 6 M) | | |
| F8 no HS | 91.4 (t = 0) | 1.50 (t = 0) | 89.3 (t = 2 W) | 1.51 (t = 2 W) |
| | 90.0 (t = 2 W) | 1.51 (t = 2 W) | 88.9 (t = 1 M) | 1.38 (t = 1 M) |
| | 91.0 (t = 1 M) | 1.52 (t = 1 M) | 84.3 (t = 3 M) | 1.48 (t = 3 M) |
| | 89.6 (t = 3 M) | 1.50 (t = 3 M) | | |
| | 91.0 (t = 6 M) | 1.49 (t = 6 M) | | |

TABLE 6-continued

Purity of free PTH (1-34) after liberation

|  | 2-8° C. % of total integrated area for free PTH (1-34) peak | 2-8° C. (% impurity) Oxidation | 25° C./60% RH % of total integrated area for free PTH (1-34) peak | 25° C./60% RH (% impurity) Oxidation |
|---|---|---|---|---|
| F8 low HS | 90.9 (t = 0) | 1.57 (t = 0) | 89.4 (t = 2 W) | 1.51 (t = 2 W) |
|  | 90.4 (t = 2 W) | 1.42 (t = 2 W) | 89.2 (t = 1 M) | 1.46 (t = 1 M) |
|  | 90.7 (t = 1 M) | 1.48 (t = 1 M) | 84.6 (t = 3 M) | 1.54 (t = 3 M) |
|  | 89.7 (t = 3 M) | 1.48 (t = 3 M) |  |  |
|  | 90.9 (t = 6 M) | 1.47 (t = 6 M) |  |  |
| F8 high HS | 90.3 (t = 0) | 1.56 (t = 0) | 89.6 (t = 2 W) | 1.58 (t = 2 W) |
|  | 90.5 (t = 2 W) | 1.47 (t = 2 W) | 88.9 (t = 1 M) | 1.49 (t = 1 M) |
|  | 90.6 (t = 1 M) | 1.45 (t = 1 M) | 84.1 (t = 3 M) | 1.53 (t = 3 M) |
|  | 89.6 (t = 3 M) | 1.43 (t = 3 M) |  |  |
|  | 90.2 (t = 6 M) | 1.46 (t = 6 M) |  |  |

Example 4

Influence of the Preservative Concentration on the Stability of Compound 1

The influence of the preservative concentration and preservative type on compound 1 and peptide stability was investigated. Towards this goal, four different formulations (F9, F10, F11, F12) comprising compound 1 at pH 4.0 were prepared. Each formulation contained 0.4 mg PTH(1-34)/mL. Formulations were filled in cartridges and incubated in incubators set at 5° C. and 40° C./75% RH for up to 6 months. After 1 month, 3 months and 6 months one cartridge per formulation and storage condition was removed from the respective incubator and subjected to analysis.

TABLE 7

|  | Compound 1 (mg PTH(1-34)/mL) | Succinic acid (mg/mL) | Mannitol (mg/mL) | m-cresol (mg/mL) | Phenol (mg/mL) | Base | pH |
|---|---|---|---|---|---|---|---|
| F9 | 0.4 | 1.18 | 41 | — | — | NaOH | 4.0 |
| F10 | 0.4 | 1.18 | 41 | — | 3.30 | NaOH | 4.0 |
| F11 | 0.4 | 1.18 | 41 | — | 1.83 | NaOH | 4.0 |
| F12 | 0.4 | 1.18 | 41 | 0.53 | 0.22 | NaOH | 4.0 |

RP-HPLC analysis revealed no free PTH for all formulations that were stored at 5° C. over 6 months. For the formulations stored at 40° C. free PTH levels increased to 5.0% and 5.5% after 3 months. Table 8 shows that no significant differences were found for the tested formulations.

TABLE 8

Free PTH/% of total integrated area for free PTH(1-34) peak

|  | 5° C. | 40° C./75% RH |
|---|---|---|
| F9 | n.d. (t = 0) | 2.14 (t = 1 M) |
|  | n.d. (t = 1 M) | 4.99 (t = 3 M) |
|  | n.d. (t = 3 M) |  |
|  | n.d. (t = 6 M) |  |
| F10 | n.d. (t = 0) | 2.27 (t = 1 M) |
|  | n.d. (t = 1 M) | 5.44 (t = 3 M) |
|  | n.d. (t = 3 M) |  |
|  | n.d. (t = 6 M) |  |

TABLE 8-continued

Free PTH/% of total integrated area for free PTH(1-34) peak

|  | 5° C. | 40° C./75% RH |
|---|---|---|
| F11 | n.d. (t = 0) | 2.24 (t = 1 M) |
|  | n.d. (t = 1 M) | 5.48 (t = 3 M) |
|  | n.d. (t = 3 M) |  |
|  | n.d. (t = 6 M) |  |
| F12 | n.d. (t = 0) | 2.18 (t = 1 M) |
|  | n.d. (t = 1 M) | 5.42 (t = 3 M) |
|  | n.d. (t = 3 M) |  |
|  | n.d. (t = 6 M) |  | n.d. = below LOQ

After release of PTH from compound 1 (pH 10.1 and 5° C.) the resulting solutions were subjected to RP-HPLC analyses. As shown in Table 9, RP-HPLC analysis did not show a decrease in peptide purity for all formulations stored at 5° C. The levels of deamidation, truncation, i.e. amount of PTH(1-30) and oxidation were unchanged after 6 months storage at 5° C. The formulations stored at 40° C. for 3 months showed a decrease in peptide purity from approximately 90% at t0 to 56-58% after 3 months. Deamidation increased from 2% to approximately 17%, PTH(1-30) increased from 0.1-0.2% to 10%. The level of oxidation was unchanged, except for a slight increase for formulation F9. No substantial differences between the analyzed formulations were observed. Therefore, the concentration or type of preservative does not have a significant influence on the stability of compound 1 and the purity of the peptide.

TABLE 9

Purity of free PTH after liberation

|   | % of total integrated area for free PTH(1-34) peak | (% impurity) Deamidated | (% impurity) PTH(1-30) | (% impurity) Oxidation |
|---|---|---|---|---|
| F9 | 90.4 (t = 0) | 1.79 (t = 0) | 0.15 (t = 0) | 1.86 (t = 0) |
| 5° C. | 90.4 (t = 1 M) | 1.89 (t = 1 M) | 0.21 (t = 1 M) | 1.75 (t = 1 M) |
|  | 89.6 (t = 3 M) | 2.32 (t = 3 M) | 0.36 (t = 3 M) | 1.72 (t = 3 M) |
|  | 90.7 (t = 6 M) | 2.10 (t = 6 M) | 0.49 (t = 6 M) | 1.83 (t = 6 M) |
| F10 | 90.9 (t = 0) | 2.00 (t = 0) | 0.11 (t = 0) | 1.77 (t = 0) |
| 5° C. | 90.2 (t = 1 M) | 2.24 (t = 1 M) | 0.19 (t = 1 M) | 1.62 (t = 1 M) |
|  | 89.1 (t = 3 M) | 2.61 (t = 3 M) | 0.33 (t = 3 M) | 1.64 (t = 3 M) |
|  | 90.2 (t = 6 M) | 2.51 (t = 6 M) | 0.42 (t = 6 M) | 1.73 (t = 6 M) |
| F11 | 90.4 (t = 0) | 1.88 (t = 0) | 0.18 (t = 0) | 1.84 (t = 0) |
| 5° C. | 90.6 (t = 1 M) | 2.07 (t = 1 M) | 0.21 (t = 1 M) | 1.64 (t = 1 M) |
|  | 89.6 (t = 3 M) | 2.48 (t = 3 M) | 0.33 (t = 3 M) | 1.67 (t = 3 M) |
|  | 90.6 (t = 6 M) | 2.34 (t = 6 M) | 0.40 (t = 6 M) | 1.70 (t = 6 M) |
| F12 | 90.3 (t = 0) | 1.89 (t = 0) | 0.16 (t = 0) | 1.82 (t = 0) |
| 5° C. | 90.4 (t = 1 M) | 2.06 (t = 1 M) | 0.22 (t = 1 M) | 1.64 (t = 1 M) |
|  | 89.5 (t = 3 M) | 2.40 (t = 3 M) | 0.29 (t = 3 M) | 1.72 (t = 3 M) |
|  | 90.4 (t = 6 M) | 2.27 (t = 6 M) | 0.43 (t = 6 M) | 1.73 (t = 6 M) |
| F9 40° C./75% RH | 77.7 (t = 1 M) 55.9 (t = 3 M) | 7.42 (t = 1 M) 16.91 (t = 3 M) | 4.09 (t = 1 M) 10.67 (t = 3 M) | 2.27 (t = 1 M) 2.91 (t = 3 M) |
| F10 40° C./75% RH | 78.7 (t = 1 M) 56.5 (t = 3 M) | 7.65 (t = 1 M) 16.90 (t = 3 M) | 3.75 (t = 1 M) 9.94 (t = 3 M) | 1.78 (t = 1 M) 1.71 (t = 3 M) |
| F11 40° C./75% RH | 79.1 (t = 1 M) 56.9 (t = 3 M) | 7.57 (t = 1 M) 17.14 (t = 3 M) | 3.85 (t = 1 M) 10.04 (t = 3 M) | 1.70 (t = 1 M) 1.66 (t = 3 M) |
| F12 40° C./75% RH | 79.5 (t = 1 M) 57.6 (t = 3 M) | 7.55 (t = 1 M) 17.37 (t = 3 M) | 3.92 (t = 1 M) 10.26 (t = 3 M) | 1.80 (t = 1 M) 1.89 (t = 3 M) |

Example 5

Stability Testing of Formulations Containing Compound 1

The influence of the concentration of compound 1 and the excipients, as well as the effect of the pH were evaluated. For this purpose, 19 formulations (F13-F31, see Table 10) comprising compound 1 at pH in the range of 3.5-4.5 were prepared. Each formulation contained 0.2-0.8 mg PTH(1-34)/mL.

TABLE 10

|  | Compound 1 (mg PTH(1-34)/mL) | Succinic acid (mg/mL) | Mannitol (mg/mL) | m-cresol (mg/mL) | Base | pH |
|---|---|---|---|---|---|---|
| F13 | 0.2 | 1.18 | 32.8 | 1.6 | NaOH | 3.5 |
| F14 | 0.8 | 1.18 | 32.8 | 1.6 | NaOH | 3.5 |
| F15 | 0.2 | 1.18 | 49.2 | 1.6 | NaOH | 3.5 |
| F16 | 0.8 | 1.18 | 49.2 | 1.6 | NaOH | 3.5 |
| F17 | 0.2 | 1.18 | 32.8 | 1.6 | NaOH | 4.5 |
| F18 | 0.8 | 1.18 | 32.8 | 1.6 | NaOH | 4.5 |
| F19 | 0.2 | 1.18 | 49.2 | 1.6 | NaOH | 4.5 |
| F20 | 0.8 | 1.18 | 49.2 | 1.6 | NaOH | 4.5 |
| F21 | 0.2 | 1.18 | 32.8 | 4.4 | NaOH | 3.5 |
| F22 | 0.8 | 1.18 | 32.8 | 4.4 | NaOH | 3.5 |
| F23 | 0.2 | 1.18 | 49.2 | 4.4 | NaOH | 3.5 |
| F24 | 0.8 | 1.18 | 49.2 | 4.4 | NaOH | 3.5 |
| F25 | 0.2 | 1.18 | 32.8 | 4.4 | NaOH | 4.5 |
| F26 | 0.8 | 1.18 | 32.8 | 4.4 | NaOH | 4.5 |
| F27 | 0.2 | 1.18 | 49.2 | 4.4 | NaOH | 4.5 |
| F28 | 0.8 | 1.18 | 49.2 | 4.4 | NaOH | 4.5 |
| F29 | 0.5 | 1.18 | 41.0 | 3.0 | NaOH | 4.0 |
| F30 | 0.5 | 1.18 | 41.0 | 3.0 | NaOH | 4.0 |
| F31 | 0.5 | 1.18 | 41.0 | 3.0 | NaOH | 4.0 |

Formulations were filled in cartridges and incubated in incubators set at 5° C., 25° C./60% RH 30° C./65% RH, and 40° C./75% RH for up to 6 months. After 1 month, 3 months and 6 months one cartridge per formulation and storage condition was removed from the respective incubator and subjected to analysis. Visual inspection results showed that for all liquid pharmaceutical formulations F13 to F31, the samples were clear, colorless and free of particles during the stability study (6 months). Only sporadically some visible particles were detected. Also, under the chosen conditions no visible aggregates were formed.

The pH of liquid pharmaceutical formulations F13 to F31 was monitored throughout 24 months when stored at 5° C., throughout 6 months when stored at 25° C. and 30° C., and throughout 3 months when stored at 40° C. and it was observed that the pH values stayed within specification of ±0.1 from the target value. No differences in the formulations were observed.

Next, different osmolality values were measured for liquid pharmaceutical formulations F13 to F31 due to different amounts of excipient in the formulations. Unchanged osmolality values were detected for all formulations after 24 months storage at 5° C., after 6 months storage at 25° C. and 30° C., as well as after 3 months storage at 40° C.

Regarding the Micro Flow-Imaging (MFI) results, it was observed that very low particle concentrations were measured for all formulations at T0 and during the stability study for up to 24 months when the formulations were stored at 5° C., for up to 6 months when the formulations were stored at 25° C. and 30° C. and for up to 3 months when the formulations were stored at 40° C. Silicone oil droplet-like particles were detected only sporadically.

Also, a photostability study with test of light exposure was performed where a liquid formulation comprising 0.3 mg PTH (1-34)/mL, 1.18 mg/mL succinic acid, 41.7 mg/mL mannitol, 2.5 mg/mL m-cresol at pH 4.0 was exposed to an illumination of 71798 lux hours combined with an UV light exposure of 8 wh/m$^2$. No differences were observed between the exposed formulation and the reference.

According to HP-SEC analyses, the fraction of high molecular weight species was unchanged within 24 months when the formulations were stored at 5° C. and within 6 months of stability study when the formulations were stored at 25° C., 30° C. and 40° C. A constant amount of HMW species indicate that no aggregates are formed within 24 months when the formulations were stored at 5° C. and within 6 months when the formulations were stored at 25° C., 30° C. and 40° C.

Analysis by RP-HPLC showed that the compound 1 content was unchanged when the formulations were stored at 5° C. for up to 24 months (Table 11). A minor decrease in content was observed for some formulations when stored for 6 months at 25° C. As shown in Table 12, this trend was more pronounced after storage at higher temperatures. Formulations with a higher pH value showed a slightly more pronounced decrease in compound 1 content than formulations with a lower pH.

TABLE 11

Compound 1 content by RP-HPLC [mg PTH(1-34)/mL]

| | 5° C. | | | | |
|---|---|---|---|---|---|
| | at t = 0 | t = 6 M | t = 12 M | t = 18 M | t = 24 M |
| F13 | 0.22 | 0.22 | 0.22 | 0.22 | 0.22 |
| F14 | 0.88 | 0.87 | 0.88 | 0.87 | 0.87 |
| F15 | 0.22 | 0.22 | 0.22 | 0.21 | 0.21 |
| F16 | 0.88 | 0.86 | 0.89 | 0.87 | 0.87 |
| F17 | 0.22 | 0.22 | 0.22 | 0.22 | 0.22 |
| F18 | 0.89 | 0.87 | 0.90 | 0.87 | 0.88 |
| F19 | 0.22 | 0.22 | 0.22 | 0.22 | 0.22 |
| F20 | 0.88 | 0.87 | 0.89 | 0.87 | 0.87 |
| F21 | 0.22 | 0.22 | 0.22 | 0.22 | 0.22 |
| F22 | 0.89 | 0.87 | 0.89 | 0.86 | 0.87 |
| F23 | 0.22 | 0.21 | 0.21 | 0.21 | 0.21 |
| F24 | 0.88 | 0.87 | 0.88 | 0.86 | 0.87 |
| F25 | 0.22 | 0.22 | 0.22 | 0.22 | 0.22 |
| F26 | 0.87 | 0.86 | 0.86 | 0.86 | 0.86 |
| F27 | 0.21 | 0.21 | 0.21 | 0.21 | 0.21 |
| F28 | 0.88 | 0.86 | 0.89 | 0.87 | 0.87 |
| F29 | 0.54 | 0.54 | 0.55 | 0.54 | 0.55 |
| F30 | 0.55 | 0.54 | 0.55 | 0.54 | 0.55 |
| F31 | 0.53 | 0.53 | 0.53 | 0.52 | 0.53 |

TABLE 12

Compound 1 content by RP-HPLC[mg PTH(1-34)/mL]

| | at 25° C. | | 30° C. | | 40° C. | |
|---|---|---|---|---|---|---|
| | t = 0 | t = 6 M | t = 1 M | t = 3 M | t = 6 M | t = 1 M | t = 3 M |
| F13 | 0.22 | 0.21 | 0.22 | 0.21 | 0.20 | 0.21 | 0.19 |
| F14 | 0.88 | 0.84 | 0.85 | 0.84 | 0.81 | 0.83 | 0.76 |
| F15 | 0.22 | 0.21 | 0.22 | 0.21 | 0.20 | 0.21 | 0.19 |
| F16 | 0.88 | 0.83 | 0.84 | 0.83 | 0.80 | 0.82 | 0.75 |
| F17 | 0.22 | 0.21 | 0.22 | 0.20 | 0.19 | 0.20 | 0.17 |
| F18 | 0.89 | 0.82 | 0.84 | 0.81 | 0.77 | 0.81 | 0.67 |
| F19 | 0.22 | 0.21 | 0.22 | 0.20 | 0.19 | 0.20 | 0.16 |
| F20 | 0.88 | 0.83 | 0.85 | 0.81 | 0.76 | 0.80 | 0.66 |
| F21 | 0.22 | 0.21 | 0.22 | 0.21 | 0.21 | 0.21 | 0.19 |
| F22 | 0.89 | 0.85 | 0.85 | 0.84 | 0.81 | 0.83 | 0.77 |
| F23 | 0.22 | 0.21 | 0.21 | 0.21 | 0.20 | 0.21 | 0.19 |
| F24 | 0.88 | 0.84 | 0.81 | 0.82 | 0.81 | 0.80 | 0.76 |
| F25 | 0.22 | 0.21 | 0.22 | 0.21 | 0.19 | 0.20 | 0.17 |

TABLE 12-continued

Compound 1 content by RP-HPLC[mg PTH(1-34)/mL]

| | at 25° C. | | 30° C. | | 40° C. | |
|---|---|---|---|---|---|---|
| | t = 0 | t = 6 M | t = 1 M | t = 3 M | t = 6 M | t = 1 M | t = 3 M |
| F26 | 0.87 | 0.80 | 0.84 | 0.80 | 0.74 | 0.78 | 0.65 |
| F27 | 0.21 | 0.20 | 0.21 | 0.20 | 0.19 | 0.20 | 0.16 |
| F28 | 0.88 | 0.82 | 0.84 | 0.81 | 0.76 | 0.79 | 0.65 |
| F29 | 0.54 | 0.52 | 0.54 | 0.52 | 0.49 | 0.51 | 0.46 |
| F30 | 0.55 | 0.53 | 0.53 | 0.52 | 0.50 | 0.52 | 0.46 |
| F31 | 0.53 | 0.51 | 0.52 | 0.51 | 0.48 | 0.50 | 0.44 |

The purity of compound 1 showed only a slight decrease when the formulations were stored at 5° C. for up to 24 months (Table 13). The purity decrease was more pronounced at higher temperatures for all formulations (Table 14). Formulations with higher pH values were more affected than formulations at lower pH.

TABLE 13

Compound 1 purity by RP-HPLC [% of total integrated area]

| | 5° C. | | | | |
|---|---|---|---|---|---|
| | at t = 0 | t = 6 M | t = 12 M | t = 18 M | t = 24 M |
| F13 | 99.6 | 99.6 | 99.4 | 99.5 | 99.5 |
| F14 | 99.7 | 99.6 | 99.1 | 99.5 | 99.1 |
| F15 | 99.6 | 99.4 | 99.2 | 99.6 | 99.2 |
| F16 | 99.6 | 99.6 | 99.3 | 99.5 | 99.4 |
| F17 | 99.6 | 99.5 | 98.7 | 99.4 | 97.9 |
| F18 | 99.6 | 99.5 | 99.3 | 99.3 | 99.3 |
| F19 | 99.6 | 99.5 | 99.3 | 99.3 | 99.4 |
| F20 | 99.6 | 99.5 | 99.0 | 99.3 | 99.4 |
| F21 | 99.6 | 99.5 | 99.2 | 99.5 | 99.4 |
| F22 | 99.6 | 99.6 | 99.0 | 99.6 | 99.4 |
| F23 | 99.7 | 99.6 | 99.0 | 99.5 | 99.5 |
| F24 | 99.7 | 99.5 | 99.2 | 99.6 | 99.3 |
| F25 | 99.6 | 99.4 | 99.0 | 99.3 | 99.5 |
| F26 | 99.7 | 99.5 | 98.4 | 98.1 | 97.7 |
| F27 | 99.6 | 99.2 | 98.9 | 98.4 | 99.2 |
| F28 | 99.6 | 99.5 | 98.8 | 99.2 | 99.2 |
| F29 | 99.7 | 99.5 | 99.0 | 99.4 | 99.2 |
| F30 | 99.7 | 99.5 | 99.2 | 99.4 | 99.2 |
| F31 | 99.6 | 99.6 | 99.2 | 99.4 | 99.5 |

TABLE 14

Compound 1 purity by RP-HPLC [% of total integrated area]

| | at 25° C. | | 30° C. | | 40° C. | |
|---|---|---|---|---|---|---|
| | t = 0 | t = 6 M | t = 1 M | t = 3 M | t = 6 M | t = 1 M | t = 3 M |
| F13 | 99.6 | 98.4 | 99.3 | 98.5 | 96.7 | 97.8 | 93.3 |
| F14 | 99.7 | 98.5 | 99.2 | 98.4 | 96.9 | 97.9 | 93.4 |
| F15 | 99.6 | 98.3 | 99.3 | 98.5 | 96.6 | 97.8 | 93.0 |
| F16 | 99.6 | 98.4 | 99.4 | 98.5 | 96.9 | 97.9 | 93.2 |
| F17 | 99.6 | 95.5 | 98.2 | 95.2 | 90.3 | 92.9 | 79.2 |
| F18 | 99.6 | 95.5 | 98.2 | 95.0 | 90.3 | 92.9 | 79.7 |
| F19 | 99.6 | 95.5 | 98.2 | 95.1 | 90.0 | 93.0 | 79.4 |
| F20 | 99.6 | 95.6 | 98.2 | 95.1 | 90.2 | 93.2 | 79.6 |
| F21 | 99.6 | 98.4 | 99.3 | 98.4 | 96.6 | 97.7 | 93.1 |
| F22 | 99.6 | 98.3 | 99.2 | 98.3 | 96.7 | 97.8 | 93.3 |
| F23 | 99.7 | 98.4 | 99.3 | 98.4 | 96.8 | 97.8 | 93.3 |
| F24 | 99.7 | 98.4 | 99.3 | 98.4 | 96.8 | 97.8 | 93.5 |
| F25 | 99.6 | 95.3 | 98.2 | 95.0 | 90.0 | 92.7 | 79.7 |
| F26 | 99.7 | 95.8 | 97.3 | 93.2 | 91.0 | 91.7 | 77.6 |
| F27 | 99.6 | 94.3 | 97.8 | 94.5 | 89.6 | 93.2 | 80.4 |
| F28 | 99.6 | 95.2 | 98.2 | 94.8 | 90.1 | 92.8 | 77.9 |
| F29 | 99.7 | 97.5 | 98.8 | 97.2 | 94.5 | 96.1 | 88.7 |

TABLE 14-continued

Compound 1 purity by RP-HPLC
[% of total integrated area]

|  | at 25° C. | | 30° C. | | | 40° C. | |
|---|---|---|---|---|---|---|---|
|  | t = 0 | t = 6 M | t = 1 M | t = 3 M | t = 6 M | t = 1 M | t = 3 M |
| F30 | 99.7 | 97.4 | 98.9 | 97.5 | 94.6 | 96.0 | 88.7 |
| F31 | 99.6 | 97.4 | 98.9 | 97.2 | 94.5 | 96.2 | 88.9 |

No free PTH was detected in formulations stored at 5° C. for 24 months. For formulations stored at higher temperatures a slight increase of free PTH was observed over time.

TABLE 15

Free PTH(1-34)
[% of total integrated area for free PTH(1-34) peak]

5° C.

|  | at t = 0 | t = 6 M | t = 12 M | t = 18 M | t = 24 M |
|---|---|---|---|---|---|
| F13 | n.d. | n.d. | n.d. | n.d. | n.d. |
| F14 | n.d. | n.d. | 0.2 | n.d. | 0.4 |
| F15 | n.d. | n.d. | 0.2 | n.d. | 0.3 |
| F16 | n.d. | n.d. | n.d. | n.d. | 0.1 |
| F17 | n.d. | n.d. | 0.2 | 0.1 | 0.3 |
| F18 | n.d. | n.d. | 0.1 | 0.2 | 0.2 |
| F19 | n.d. | n.d. | n.d. | 0.2 | 0.1 |
| F20 | n.d. | n.d. | n.d. | 0.2 | 0.1 |
| F21 | n.d. | n.d. | 0.1 | n.d. | 0.2 |
| F22 | n.d. | n.d. | n.d. | n.d. | n.d. |
| F23 | n.d. | n.d. | n.d. | n.d. | n.d. |
| F24 | n.d. | n.d. | 0.1 | n.d. | 0.2 |
| F25 | n.d. | n.d. | n.d. | 0.2 | n.d. |
| F26 | n.d. | 0.1 | 0.2 | 0.3 | 0.4 |
| F27 | n.d. | n.d. | 0.1 | 0.2 | 0.3 |
| F28 | n.d. | 0.1 | 0.2 | 0.3 | 0.3 |
| F29 | n.d. | n.d. | 0.1 | 0.1 | 0.2 |
| F30 | n.d. | n.d. | 0.1 | 0.1 | 0.3 |
| F31 | n.d. | n.d. | 0.1 | 0.1 | 0.1 | n.d. = below LOQ

TABLE 16

Free PTH(1-34)
[% of total integrated area for free PTH(1-34) peak]

|  | at 25° C. | | 30° C. | | | 40° C. | |
|---|---|---|---|---|---|---|---|
|  | t = 0 | t = 6 M | t = 1 M | t = 3 M | t = 6 M | t = 1 M | t = 3 M |
| F13 | n.d. | 0.8 | 0.3 | 0.8 | 1.4 | 1.2 | 2.7 |
| F14 | n.d. | 0.7 | 0.3 | 0.8 | 1.4 | 1.2 | 2.5 |
| F15 | n.d. | 0.8 | 0.3 | 0.9 | 1.5 | 1.3 | 2.9 |
| F16 | n.d. | 0.7 | 0.2 | 0.7 | 1.4 | 1.2 | 2.6 |
| F17 | n.d. | 3.2 | 1.2 | 3.5 | 6.2 | 5.3 | 11.3 |
| F18 | n.d. | 3.2 | 1.2 | 3.7 | 6.3 | 5.3 | 11.1 |
| F19 | n.d. | 3.1 | 1.2 | 3.7 | 6.3 | 5.2 | 11.4 |
| F20 | n.d. | 3.1 | 1.1 | 3.6 | 6.2 | 5.0 | 11.1 |
| F21 | n.d. | 0.8 | 0.3 | 0.9 | 1.7 | 1.3 | 2.9 |
| F22 | n.d. | 0.8 | 0.3 | 0.9 | 1.6 | 1.3 | 2.8 |
| F23 | n.d. | 0.8 | 0.3 | 0.9 | 1.5 | 1.3 | 2.8 |
| F24 | n.d. | 0.8 | 0.3 | 0.8 | 1.5 | 1.3 | 2.7 |
| F25 | n.d. | 3.3 | 1.3 | 3.7 | 6.4 | 5.5 | 11.2 |
| F26 | n.d. | 3.1 | 1.3 | 3.5 | 6.0 | 5.1 | 10.6 |
| F27 | n.d. | 2.9 | 1.2 | 3.4 | 6.0 | 5.1 | 10.8 |
| F28 | n.d. | 3.4 | 1.2 | 3.8 | 6.6 | 5.4 | 11.8 |
| F29 | n.d. | 1.5 | 0.7 | 1.8 | 3.2 | 2.6 | 5.8 |
| F30 | n.d. | 1.6 | 0.6 | 1.7 | 3.1 | 2.7 | 5.8 |
| F31 | n.d. | 1.6 | 0.6 | 1.9 | 3.2 | 2.6 | 5.8 | n.d. = below LOQ

Formulations with higher pH values showed a stronger increase in free PTH species than formulations with lower pH values, but no substantial differences were observed between the analyzed formulations.

TABLE 17

Free PTH related species
[% of total integrated area]

5° C.

|  | at t = 0 | t = 6 M | t = 12 M | t = 18 M | t = 24 M |
|---|---|---|---|---|---|
| F13 | n.d. | n.d. | n.d. | n.d. | n.d. |
| F14 | n.d. | n.d. | n.d. | n.d. | n.d. |
| F15 | n.d. | n.d. | n.d. | n.d. | n.d. |
| F16 | n.d. | n.d. | n.d. | n.d. | n.d. |
| F17 | n.d. | n.d. | n.d. | n.d. | n.d. |
| F18 | n.d. | n.d. | n.d. | n.d. | n.d. |
| F19 | n.d. | n.d. | n.d. | n.d. | n.d. |
| F20 | n.d. | n.d. | n.d. | n.d. | n.d. |
| F21 | n.d. | n.d. | n.d. | n.d. | n.d. |
| F22 | n.d. | n.d. | n.d. | n.d. | n.d. |
| F23 | n.d. | n.d. | n.d. | n.d. | n.d. |
| F24 | n.d. | n.d. | n.d. | n.d. | n.d. |
| F25 | n.d. | n.d. | n.d. | n.d. | n.d. |
| F26 | n.d. | n.d. | n.d. | n.d. | n.d. |
| F27 | n.d. | n.d. | n.d. | n.d. | n.d. |
| F28 | n.d. | n.d. | n.d. | n.d. | n.d. |
| F29 | n.d. | n.d. | n.d. | n.d. | n.d. |
| F30 | n.d. | n.d. | n.d. | n.d. | n.d. |
| F31 | n.d. | n.d. | n.d. | n.d. | n.d. | n.d. = below LOQ

TABLE 18

Free PTH related species
[% of total integrated area]

|  | at 25° C. | | 30° C. | | | 40° C. | |
|---|---|---|---|---|---|---|---|
|  | t = 0 | t = 6 M | t = 1 M | t = 3 M | t = 6 M | t = 1 M | t = 3 M |
| F13 | n.d. | n.d. | n.d. | n.d. | 0.7 | 0.1 | 2.2 |
| F14 | n.d. | n.d. | n.d. | n.d. | 0.5 | 0.1 | 2.1 |
| F15 | n.d. | 0.1 | n.d. | n.d. | 0.7 | 0.1 | 2.3 |
| F16 | n.d. | 0.1 | n.d. | n.d. | 0.5 | 0.1 | 2.2 |
| F17 | n.d. | 0.2 | n.d. | 0.2 | 1.7 | 0.6 | 6.5 |
| F18 | n.d. | 0.2 | n.d. | 0.3 | 1.7 | 0.5 | 6.1 |
| F19 | n.d. | 0.2 | n.d. | 0.2 | 1.7 | 0.5 | 6.3 |
| F20 | n.d. | 0.3 | n.d. | 0.2 | 1.7 | 0.5 | 6.3 |
| F21 | n.d. | n.d. | n.d. | n.d. | 0.6 | 0.2 | 2.1 |
| F22 | n.d. | 0.1 | n.d. | 0.1 | 0.6 | 0.1 | 2.1 |
| F23 | n.d. | n.d. | n.d. | n.d. | 0.6 | 0.2 | 2.1 |
| F24 | n.d. | n.d. | n.d. | n.d. | 0.5 | 0.2 | 2.1 |
| F25 | n.d. | 0.3 | n.d. | 0.2 | 1.7 | 0.6 | 6.1 |
| F26 | n.d. | 0.3 | n.d. | 0.2 | 1.7 | 0.6 | 6.1 |
| F27 | n.d. | 0.1 | n.d. | 0.2 | 1.3 | 0.5 | 5.7 |
| F28 | n.d. | 0.3 | n.d. | 0.2 | 1.6 | 0.5 | 7.1 |
| F29 | n.d. | 0.1 | n.d. | 0.1 | 0.9 | 0.4 | 3.3 |
| F30 | n.d. | 0.1 | n.d. | n.d. | 0.9 | 0.3 | 3.3 |
| F31 | n.d. | 0.1 | n.d. | 0.1 | 0.9 | 0.3 | 3.2 | n.d. = below LOQ

RP-HPLC after release of PTH (pH 10.1 and 5° C.) showed no significant changes in the purity of free PTH for formulations stored at 5° C. for up to 24 months. At higher temperatures a time and temperature dependent decrease in purity was found. Formulations with lower pH values were characterized by slightly lower purities than formulations with higher pH.

TABLE 19

Free PTH(1-34) purity after liberation
[% of total integrated area for free PTH(1-34) peak]

| | 5° C. | | | | |
|---|---|---|---|---|---|
| | at t = 0 | t = 6 M | t = 12 M | t = 18 M | t = 24 M |
| F13 | 93.2 | 92.8 | 92.2 | 91.4 | 90.4 |
| F14 | 93.6 | 92.4 | 93.1 | 91.4 | 90.6 |
| F15 | 93.4 | 92.2 | 92.4 | 91.0 | 89.4 |
| F16 | 92.9 | 92.9 | 93.1 | 90.7 | 90.6 |
| F17 | 93.4 | 92.7 | 92.7 | 92.2 | 91.8 |
| F18 | 93.4 | 93.5 | 93.9 | 92.4 | 91.7 |
| F19 | 93.9 | 93.4 | 92.8 | 91.5 | 91.2 |
| F20 | 94.0 | 92.8 | 94.1 | 92.7 | 90.5 |
| F21 | 92.9 | 92.9 | 92.0 | 91.2 | 89.8 |
| F22 | 93.3 | 92.4 | 93.1 | 91.1 | 89.0 |
| F23 | 93.1 | 92.7 | 91.7 | 91.2 | 90.3 |
| F24 | 93.1 | 92.4 | 92.9 | 91.3 | 89.7 |
| F25 | 93.2 | 93.0 | 92.6 | 92.0 | 90.9 |
| F26 | 93.6 | 92.3 | 93.1 | 90.8 | 90.4 |
| F27 | 93.2 | 92.6 | 91.6 | 91.6 | 90.4 |
| F28 | 93.1 | 92.5 | 93.4 | 92.2 | 92.0 |
| F29 | 93.6 | 92.3 | 92.7 | 91.6 | 90.7 |
| F30 | 93.3 | 93.4 | 92.8 | 91.6 | 91.2 |
| F31 | 93.4 | 92.9 | 92.6 | 92.1 | 90.8 |

TABLE 20

Free PTH(1-34) purity after liberation
[% of total integrated area for free PTH(1-34) peak]

| | at 25° C. | | 30° C. | | 40° C. | |
|---|---|---|---|---|---|---|
| | t = 0 | t = 6 M | t = 1 M | t = 3 M | t = 6 M | t = 1 M | t = 3 M |
| F13 | 93.2 | 78.9 | 88.2 | 80.0 | 67.8 | 78.9 | 54.5 |
| F14 | 93.6 | 79.4 | 88.7 | 80.1 | 67.4 | 79.4 | 54.1 |
| F15 | 93.4 | 79.6 | 88.0 | 80.2 | 69.0 | 79.2 | 54.5 |
| F16 | 92.9 | 79.7 | 88.7 | 79.5 | 67.5 | 78.7 | 53.6 |
| F17 | 93.4 | 82.9 | 89.6 | 82.9 | 73.3 | 81.1 | 59.2 |
| F18 | 93.4 | 83.0 | 90.0 | 83.2 | 72.9 | 81.6 | 59.5 |
| F19 | 93.9 | 83.1 | 90.1 | 83.0 | 73.0 | 81.2 | 59.2 |
| F20 | 94.0 | 83.3 | 89.7 | 82.8 | 72.9 | 81.8 | 59.6 |
| F21 | 92.9 | 79.7 | 88.4 | 80.2 | 68.0 | 79.1 | 54.9 |
| F22 | 93.3 | 79.2 | 88.8 | 79.8 | 68.0 | 79.2 | 54.9 |
| F23 | 93.1 | 79.6 | 88.3 | 80.3 | 68.3 | 78.6 | 55.4 |
| F24 | 93.1 | 78.8 | 88.7 | 79.5 | 67.8 | 78.7 | 54.6 |
| F25 | 93.2 | 82.7 | 89.2 | 82.8 | 73.1 | 80.9 | 59.5 |
| F26 | 93.6 | 79.5 | 88.6 | 80.1 | 69.5 | 80.1 | 57.4 |
| F27 | 93.2 | 81.0 | 89.2 | 82.2 | 71.9 | 80.8 | 60.3 |
| F28 | 93.1 | 82.8 | 90.2 | 83.4 | 72.8 | 81.5 | 59.2 |
| F29 | 93.6 | 82.4 | 89.6 | 82.5 | 71.6 | 81.0 | 59.3 |
| F30 | 93.3 | 82.3 | 89.5 | 82.1 | 72.4 | 80.6 | 59.3 |
| F31 | 93.4 | 81.9 | 88.9 | 82.4 | 72.1 | 81.8 | 59.7 |

As shown in Tables 21 and 22, after liberation of PTH no substantial increase of oxidized species was found for any formulations or storage conditions. Only a minor increase of one oxidized species was found in all formulations. This increase was slightly more pronounced at higher temperature.

TABLE 21

Free PTH(1-34) purity after liberation [% impurity]
total oxidation

| | 5° C. | | | | |
|---|---|---|---|---|---|
| | at t = 0 | t = 6 M | t = 12 M | t = 18 M | t = 24 M |
| F13 | 0.57 | 0.62 | 0.70 | 0.69 | 0.68 |
| F14 | 0.49 | 0.63 | 0.53 | 0.52 | 0.54 |
| F15 | 0.58 | 0.71 | 0.69 | 0.64 | 0.84 |

TABLE 21-continued

Free PTH(1-34) purity after liberation [% impurity]
total oxidation

| | 5° C. | | | | |
|---|---|---|---|---|---|
| | at t = 0 | t = 6 M | t = 12 M | t = 18 M | t = 24 M |
| F16 | 0.54 | 0.62 | 0.55 | 0.67 | 0.63 |
| F17 | 0.59 | 0.66 | 0.71 | 0.70 | 0.78 |
| F18 | 0.44 | 0.7 | 0.58 | 0.64 | 0.63 |
| F19 | 0.56 | 0.66 | 0.61 | 0.74 | 0.81 |
| F20 | 0.5 | 0.56 | 0.61 | 0.67 | 0.90 |
| F21 | 0.56 | 0.75 | 0.74 | 0.75 | 0.75 |
| F22 | 0.56 | 0.62 | 0.58 | 0.65 | 0.72 |
| F23 | 0.6 | 0.77 | 0.79 | 0.80 | 0.85 |
| F24 | 0.54 | 0.60 | 0.65 | 0.72 | 0.79 |
| F25 | 0.66 | 0.69 | 0.76 | 0.75 | 0.76 |
| F26 | 0.64 | 0.78 | 0.69 | 0.81 | 0.82 |
| F27 | 0.54 | 0.66 | 0.80 | 0.82 | 0.93 |
| F28 | 0.54 | 0.76 | 0.62 | 0.72 | 0.57 |
| F29 | 0.56 | 0.75 | 0.65 | 0.74 | 0.78 |
| F30 | 0.53 | 0.62 | 0.59 | 0.76 | 0.68 |
| F31 | 0.43 | 0.51 | 0.56 | 0.68 | 0.67 |

TABLE 22

Free PTH(1-34) purity after liberation [% impurity]
total oxidation

| | at 25° C. | | 30° C. | | 40° C. | |
|---|---|---|---|---|---|---|
| | t = 0 | t = 6 M | t = 1 M | t = 3 M | t = 6 M | t = 1 M | t = 3 M |
| F13 | 0.57 | 0.93 | 0.76 | 0.81 | 1.13 | 0.9 | 1.19 |
| F14 | 0.49 | 0.76 | 0.57 | 0.73 | 1.55 | 0.69 | 1.09 |
| F15 | 0.58 | 0.86 | 0.75 | 0.82 | 1.02 | 0.87 | 1.15 |
| F16 | 0.54 | 0.73 | 0.69 | 0.87 | 1.31 | 0.72 | 1.14 |
| F17 | 0.59 | 0.75 | 0.72 | 0.61 | 0.73 | 0.7 | 0.96 |
| F18 | 0.44 | 0.71 | 0.63 | 0.61 | 0.85 | 0.65 | 0.88 |
| F19 | 0.56 | 0.71 | 0.7 | 0.66 | 0.83 | 0.64 | 0.9 |
| F20 | 0.5 | 0.68 | 0.55 | 0.66 | 0.74 | 0.6 | 0.89 |
| F21 | 0.56 | 0.96 | 0.8 | 0.81 | 1.2 | 0.93 | 1.31 |
| F22 | 0.56 | 0.75 | 0.72 | 0.74 | 0.97 | 0.76 | 1.17 |
| F23 | 0.6 | 1.03 | 0.89 | 0.83 | 1.11 | 0.88 | 1.2 |
| F24 | 0.54 | 1.09 | 0.66 | 0.79 | 0.96 | 0.75 | 1.09 |
| F25 | 0.66 | 0.89 | 0.77 | 0.74 | 0.87 | 0.76 | 1.04 |
| F26 | 0.64 | 1.22 | 0.83 | 1.33 | 1.3 | 0.92 | 1.11 |
| F27 | 0.54 | 0.91 | 0.61 | 0.81 | 0.93 | 0.82 | 0.97 |
| F28 | 0.54 | 0.84 | 0.57 | 0.69 | 0.87 | 0.73 | 0.87 |
| F29 | 0.56 | 0.72 | 0.7 | 0.75 | 0.88 | 0.77 | 1.08 |
| F30 | 0.53 | 0.83 | 0.67 | 0.85 | 0.86 | 0.75 | 0.99 |
| F31 | 0.43 | 0.74 | 0.65 | 0.72 | 0.81 | 0.64 | 0.94 |

RP-HPLC analyses showed a time and temperature dependent increase of PTH(1-30) for all formulations. Formulations with lower pH were characterized by a slightly higher amount of PTH(1-30) as compared to the formulations with higher pH values.

TABLE 23

Free PTH(1-34) purity after liberation [% impurity]
PTH(1-30)

| at | 5° C. | 25° C. | 30° C. | | | 40° C. | |
|---|---|---|---|---|---|---|---|
| | t = 0 | t = 6 M | t = 6 M | t = 1 M | t = 3 M | t = 6 M | t = 1 M | t = 3 M |

| | t = 0 | t = 6 M | t = 6 M | t = 1 M | t = 3 M | t = 6 M | t = 1 M | t = 3 M |
|---|---|---|---|---|---|---|---|---|
| F13 | 0.24 | 0.66 | 6.94 | 2.27 | 6.71 | 12.25 | 6.72 | 18.19 |
| F14 | 0.19 | 0.63 | 7.31 | 2.39 | 7.09 | 12.67 | 7.12 | 18.89 |
| F15 | 0.18 | 0.59 | 6.69 | 2.22 | 6.35 | 11.64 | 6.59 | 17.57 |
| F16 | 0.23 | 0.58 | 7.23 | 2.42 | 6.98 | 12.60 | 7.40 | 18.89 |
| F17 | 0.18 | 0.30 | 2.00 | 0.71 | 1.98 | 3.35 | 1.95 | 4.66 |
| F18 | 0.17 | 0.31 | 2.11 | 0.74 | 1.98 | 3.50 | 2.03 | 4.82 |
| F19 | 0.20 | 0.33 | 1.96 | 0.70 | 1.88 | 3.32 | 1.92 | 4.52 |
| F20 | 0.18 | 0.38 | 2.03 | 0.76 | 1.91 | 3.41 | 1.95 | 4.68 |
| F21 | 0.21 | 0.60 | 6.46 | 2.18 | 6.26 | 11.35 | 6.47 | 17.22 |
| F22 | 0.22 | 0.60 | 6.68 | 2.23 | 6.49 | 11.75 | 6.61 | 17.52 |
| F23 | 0.17 | 0.60 | 6.56 | 2.22 | 6.35 | 11.44 | 6.53 | 17.25 |
| F24 | 0.21 | 0.60 | 6.91 | 2.31 | 6.69 | 12.07 | 6.79 | 17.82 |
| F25 | 0.20 | 0.29 | 2.00 | 0.74 | 1.85 | 3.28 | 1.94 | 4.44 |
| F26 | 0.16 | 0.29 | 2.04 | 0.78 | 2.00 | 3.30 | 1.96 | 4.60 |
| F27 | 0.13 | 0.30 | 2.08 | 0.73 | 1.89 | 3.46 | 1.93 | 4.75 |
| F28 | 0.15 | 0.36 | 1.97 | 0.68 | 1.84 | 3.28 | 1.83 | 4.59 |
| F29 | 0.20 | 0.46 | 3.89 | 1.36 | 3.78 | 6.89 | 3.75 | 10.11 |
| F30 | 0.15 | 0.36 | 3.95 | 1.41 | 3.81 | 6.88 | 3.91 | 10.10 |
| F31 | 0.18 | 0.42 | 3.91 | 1.28 | 3.76 | 6.79 | 3.72 | 9.83 |

Tables 24 and 25 indicate a temperature and time dependent increase of deamidated species for all formulations. For formulations stored at 5° C., the amount of deamidated species was not significantly changed after 24 months storage.

TABLE 24

Free PTH(1-34) purity after liberation [% impurity]
total deamidation

5° C.

| | at t = 0 | t = 6 M | t = 12 M | t = 18 M | t = 24 M |
|---|---|---|---|---|---|
| F13 | 1.67 | 1.92 | 2.30 | 2.09 | 2.44 |
| F14 | 1.59 | 1.99 | 2.23 | 1.98 | 2.44 |
| F15 | 1.87 | 1.79 | 2.06 | 2.00 | 2.48 |
| F16 | 1.63 | 1.70 | 1.89 | 1.99 | 2.37 |
| F17 | 1.69 | 2.03 | 2.50 | 2.19 | 2.77 |
| F18 | 1.65 | 1.95 | 2.26 | 2.18 | 2.79 |
| F19 | 1.50 | 1.73 | 2.29 | 2.16 | 2.64 |
| F20 | 1.45 | 1.89 | 2.10 | 1.89 | 2.74 |
| F21 | 1.88 | 2.02 | 2.31 | 2.16 | 2.59 |
| F22 | 1.76 | 2.01 | 2.27 | 2.03 | 2.82 |
| F23 | 1.73 | 1.79 | 2.31 | 1.93 | 2.46 |
| F24 | 1.73 | 1.86 | 2.14 | 1.86 | 2.55 |
| F25 | 1.81 | 2.04 | 2.48 | 2.29 | 3.04 |
| F26 | 1.74 | 1.94 | 2.48 | 2.22 | 3.34 |
| F27 | 1.72 | 2.02 | 2.39 | 2.13 | 3.01 |
| F28 | 1.72 | 1.94 | 2.22 | 2.46 | 2.61 |
| F29 | 1.70 | 2.03 | 2.34 | 2.07 | 2.66 |
| F30 | 1.78 | 1.84 | 2.22 | 2.01 | 2.43 |
| F31 | 1.70 | 1.96 | 2.28 | 2.01 | 2.49 |

TABLE 25

Free PTH(1-34) purity after liberation [% impurity]
total deamidation

| at | 25° C. | 30° C. | | | 40° C. | |
|---|---|---|---|---|---|---|
| | t = 0 | t = 6 M | t = 1 M | t = 3 M | t = 6 M | t = 1 M | t = 3 M |
| F13 | 1.67 | 6.06 | 3.16 | 5.88 | 9.32 | 6.23 | 13.69 |
| F14 | 1.59 | 5.91 | 3.03 | 5.79 | 9.22 | 6.11 | 13.34 |
| F15 | 1.87 | 5.86 | 3.08 | 5.99 | 9.27 | 6.32 | 13.88 |
| F16 | 1.63 | 5.66 | 2.97 | 5.66 | 9.04 | 6.22 | 13.29 |
| F17 | 1.69 | 8.41 | 3.90 | 8.52 | 14.20 | 9.45 | 22.06 |
| F18 | 1.65 | 8.43 | 3.79 | 8.27 | 13.98 | 9.60 | 21.70 |
| F19 | 1.50 | 8.25 | 3.82 | 8.48 | 14.13 | 9.28 | 21.76 |
| F20 | 1.45 | 8.12 | 3.81 | 8.27 | 13.83 | 9.00 | 21.51 |
| F21 | 1.88 | 6.17 | 3.26 | 6.08 | 9.54 | 6.50 | 13.82 |
| F22 | 1.76 | 6.18 | 3.19 | 5.91 | 9.41 | 6.38 | 13.49 |
| F23 | 1.73 | 5.93 | 3.13 | 5.87 | 9.17 | 6.34 | 13.59 |
| F24 | 1.73 | 5.89 | 2.99 | 5.94 | 9.14 | 6.17 | 13.32 |
| F25 | 1.81 | 8.44 | 4.02 | 8.46 | 14.11 | 9.60 | 21.59 |
| F26 | 1.74 | 7.91 | 3.94 | 8.06 | 13.04 | 9.23 | 20.74 |
| F27 | 1.72 | 7.77 | 3.64 | 8.00 | 13.11 | 9.08 | 20.78 |
| F28 | 1.72 | 8.08 | 3.75 | 8.18 | 13.67 | 9.40 | 22.07 |
| F29 | 1.70 | 6.71 | 3.30 | 6.97 | 11.20 | 7.70 | 16.89 |
| F30 | 1.78 | 6.74 | 3.33 | 6.91 | 11.14 | 7.67 | 17.08 |
| F31 | 1.70 | 6.79 | 3.50 | 6.87 | 11.21 | 7.50 | 16.87 |

Abbreviations

CHAPS—3-[(3-Cholamidopropyl)dimethylammonio]-1-propanesulfonate
EDTA—ethylenediaminetetraacetic acid
HEPES—4-(2-hydroxyethyl)-1-piperazineethanesulfonic acid
LC-MS—liquid chromatography-coupled mass spectrometry
M—month
n.d.—not determinable or below the limit of quantification (LOQ)
pH—potential Hydrogenii
PTH—parathyroid hormone
RH—relative humidity
RP-HPLC—reversed phase high performance liquid chromatography
SEC—size-exclusion chromatography
sec—seconds TFA—trifluoroacetic acid
TRIS—tris(hydroxymethyl)aminomethane UPLC—ultra performance liquid chromatography
W—week

The invention claimed is:

1. A liquid pharmaceutical formulation, wherein the pharmaceutical formulation comprises a PTH conjugate of formula

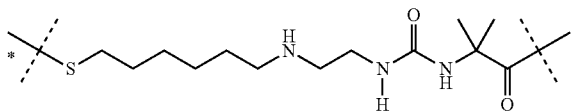

or a pharmaceutically acceptable salt thereof,
wherein
the unmarked dashed line indicates attachment by an amide bond to an N-terminal amine of a PTH moiety, which is PTH1-34 (SEQ ID NO:51); and
the dashed line marked with the asterisk indicates attachment to a moiety

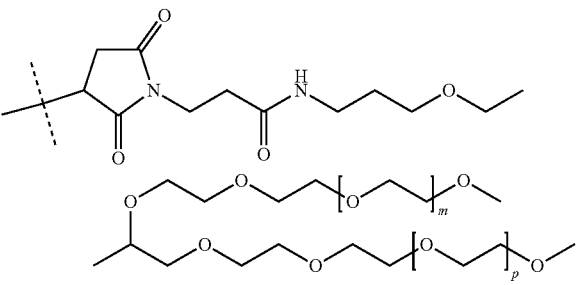

wherein m and p are independently an integer from 400-500,
succinic acid, D-mannitol and m-cresol, wherein the PTH moiety is at about 0.3 mg/ml mg/ml, the succinic acid is at about 1.18 mg/ml, the D-mannitol is at about 41.7 mg/ml, and the m-cresol is at about 2.5 mg/ml and wherein the pH is about 4.0, wherein about indicates variation of +/−10% of a stated value.

2. A method of manufacturing the liquid pharmaceutical formulation of claim 1, wherein the method comprises the steps of (i) admixing the PTH conjugate with the succinic acid, D-mannitol and m-cresol;

(ii) adjusting the pH of the admixture of step (i);

(iii) optionally, filtering the admixture from step (ii);

(iv) transferring amounts of the admixture from step (ii) or (iii) equivalent to the desired number of dosages into a container;

(v) sealing the container; and wherein the order of steps (ii) and (iii) may optionally be reversed.

3. The method of manufacturing of claim 2, wherein steps (ii) and (iii) are not reversed.

4. A method of treating, controlling, delaying or preventing in a patient one or more diseases which can be treated by PTH, the method comprising administering to the patient a therapeutically pharmaceutical formulation of claim 1.

5. The method of claim 4, wherein the disease is selected from the group consisting of hypoparathyroidism, hyperphosphatemia, osteoporosis, fracture repair, osteomalacia, osteomalacia and osteoporosis in patients with hypophosphatasia, steroid-induced osteoporosis, male osteoporosis, arthritis, osteoarthritis, osteogenesis imperfecta, fibrous dysplasia, rheumatoid arthritis, Paget's disease, humoral hypercalcemia associated with malignancy, osteopenia, periodontal disease, bone fracture, alopecia, chemotherapy-induced alopecia and thrombocytopenia, chronic periodontitis, osteonecrosis of jaw and poorly healing fractures due to ALPL gene mutations.

6. The method of claim 4, wherein the disease is hypoparathyroidism.

7. The liquid pharmaceutical formulation of claim 1, wherein the PTH conjugate is of the formula

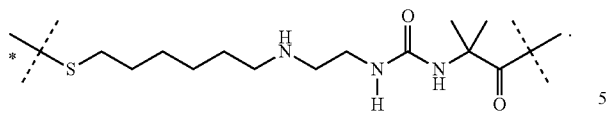
wherein
the unmarked dashed line indicates attachment by an amide bond to an N-terminal amine of a PTH moiety, which is PTH1-34 (SEQ ID NO:51); and
the dashed line marked with the asterisk indicates attachment to a moiety
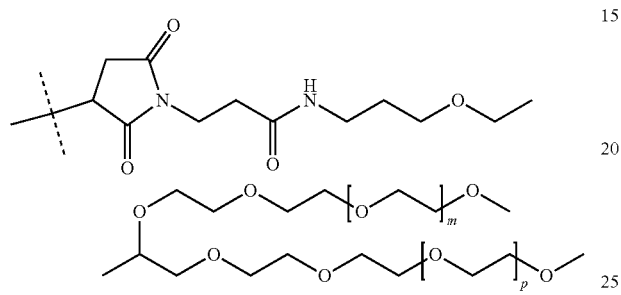
wherein m and p are independently an integer from 400-500.
8. The liquid pharmaceutical formulation of claim 1, which is free of an antioxidant.

UNITED STATES PATENT AND TRADEMARK OFFICE
CERTIFICATE OF CORRECTION

PATENT NO. : 12,403,182 B2  
APPLICATION NO. : 17/428608  
DATED : September 2, 2025  
INVENTOR(S) : Anja R. H. Skands et al.

Page 1 of 2

It is certified that error appears in the above-identified patent and that said Letters Patent is hereby corrected as shown below:

In the Claims

In Column 173, Lines 31-37, Claim 1, delete

"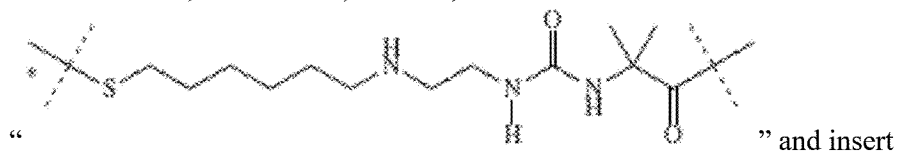" and insert

--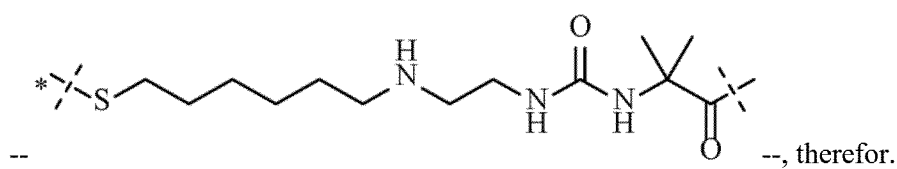--, therefor.

In Column 173, Line 63, Claim 1, delete "mg/ml mg/ml," and insert -- mg/ml, --, therefor.

In Column 174, Line 48, Claim 4, delete "therapeutically pharmaceutical" and insert -- therapeutically effective amount of the pharmaceutical --, therefor.

In Column 175, Lines 1-6, Claim 7, delete

"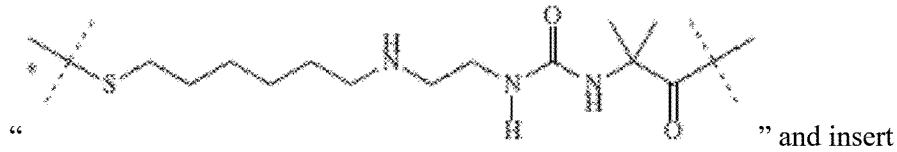" and insert

--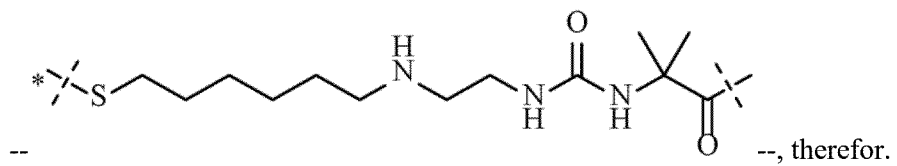--, therefor.

Signed and Sealed this  
Sixteenth Day of December, 2025

John A. Squires  
*Director of the United States Patent and Trademark Office*

In Column 175, Line 10, Claim 7, delete "an N-terminal amine" and insert -- the N-terminal amine --, therefor.

```
                          SEQUENCE LISTING

<160> NUMBER OF SEQ ID NOS: 122

<210> SEQ ID NO 1
<211> LENGTH: 84
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 2
<211> LENGTH: 83
<212> TYPE: PRT
<213> ORGANISM: Artificial Sequence
<220> FEATURE:
<223> OTHER INFORMATION: Human PTH 1-83

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser

<210> SEQ ID NO 3
<211> LENGTH: 82
<212> TYPE: PRT
<213> ORGANISM: Artificial Sequence
<220> FEATURE:
<223> OTHER INFORMATION: human PTH 1-82

<400> SEQUENCE: 3

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60
```

```
Lys Ser Leu Gly Glu Ala Asp Lys Ala Asp Val Asn Val Leu Thr Lys
 65                  70                  75                  80

Ala Lys

<210> SEQ ID NO 4
<211> LENGTH: 81
<212> TYPE: PRT
<213> ORGANISM: Artificial Sequence
<220> FEATURE:
<223> OTHER INFORMATION: human PTH 1-81

<400> SEQUENCE: 4

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
             35                  40                  45

Gln Arg Pro Arg Lys Lys Glu Asp Asn Val Leu Val Glu Ser His Glu
         50                  55                  60

Lys Ser Leu Gly Glu Ala Asp Lys Ala Asp Val Asn Val Leu Thr Lys
 65                  70                  75                  80

Ala

<210> SEQ ID NO 5
<211> LENGTH: 80
<212> TYPE: PRT
<213> ORGANISM: Artificial Sequence
<220> FEATURE:
<223> OTHER INFORMATION: human PTH 1-80

<400> SEQUENCE: 5

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
             35                  40                  45

Gln Arg Pro Arg Lys Lys Glu Asp Asn Val Leu Val Glu Ser His Glu
         50                  55                  60

Lys Ser Leu Gly Glu Ala Asp Lys Ala Asp Val Asn Val Leu Thr Lys
 65                  70                  75                  80

<210> SEQ ID NO 6
<211> LENGTH: 79
<212> TYPE: PRT
<213> ORGANISM: Artificial Sequence
<220> FEATURE:
<223> OTHER INFORMATION: human PTH 1-79

<400> SEQUENCE: 6

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
             35                  40                  45

Gln Arg Pro Arg Lys Lys Glu Asp Asn Val Leu Val Glu Ser His Glu
         50                  55                  60
```

Lys Ser Leu Gly Glu Ala Asp Lys Ala Asp Val Asn Val Leu Thr
65                  70                  75

<210> SEQ ID NO 7
<211> LENGTH: 78
<212> TYPE: PRT
<213> ORGANISM: Artificial Sequence
<220> FEATURE:
<223> OTHER INFORMATION: human PTH 1-78

<400> SEQUENCE: 7

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu
65                  70                  75

<210> SEQ ID NO 8
<211> LENGTH: 77
<212> TYPE: PRT
<213> ORGANISM: Artificial Sequence
<220> FEATURE:
<223> OTHER INFORMATION: human PTH 1-77

<400> SEQUENCE: 8

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val
65                  70                  75

<210> SEQ ID NO 9
<211> LENGTH: 76
<212> TYPE: PRT
<213> ORGANISM: Artificial Sequence
<220> FEATURE:
<223> OTHER INFORMATION: human PTH 1-76

<400> SEQUENCE: 9

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn
65                  70                  75

<210> SEQ ID NO 10
<211> LENGTH: 75
<212> TYPE: PRT
<213> ORGANISM: Artificial Sequence
<220> FEATURE:
<223> OTHER INFORMATION: human PTH 1-75

<400> SEQUENCE: 10

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val
65                  70                  75

<210> SEQ ID NO 11
<211> LENGTH: 74
<212> TYPE: PRT
<213> ORGANISM: Artificial Sequence
<220> FEATURE:
<223> OTHER INFORMATION: human PTH 1-74

<400> SEQUENCE: 11

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp
65                  70

<210> SEQ ID NO 12
<211> LENGTH: 73
<212> TYPE: PRT
<213> ORGANISM: Artificial Sequence
<220> FEATURE:
<223> OTHER INFORMATION: human PTH 1-73

<400> SEQUENCE: 12

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala
65                  70

<210> SEQ ID NO 13
<211> LENGTH: 72
<212> TYPE: PRT
<213> ORGANISM: Artificial Sequence

```
<220> FEATURE:
<223> OTHER INFORMATION: human PTH 1-72

<400> SEQUENCE: 13

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys
65                  70

<210> SEQ ID NO 14
<211> LENGTH: 71
<212> TYPE: PRT
<213> ORGANISM: Artificial Sequence
<220> FEATURE:
<223> OTHER INFORMATION: human PTH 1-71

<400> SEQUENCE: 14

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp
65                  70

<210> SEQ ID NO 15
<211> LENGTH: 70
<212> TYPE: PRT
<213> ORGANISM: Artificial Sequence
<220> FEATURE:
<223> OTHER INFORMATION: human PTH 1-70

<400> SEQUENCE: 15

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala
65                  70

<210> SEQ ID NO 16
<211> LENGTH: 69
<212> TYPE: PRT
<213> ORGANISM: Artificial Sequence
<220> FEATURE:
<223> OTHER INFORMATION: human PTH 1-69

<400> SEQUENCE: 16
```

-continued

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu
65

<210> SEQ ID NO 17
<211> LENGTH: 68
<212> TYPE: PRT
<213> ORGANISM: Artificial Sequence
<220> FEATURE:
<223> OTHER INFORMATION: human PTH 1-68

<400> SEQUENCE: 17

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly
65

<210> SEQ ID NO 18
<211> LENGTH: 67
<212> TYPE: PRT
<213> ORGANISM: Artificial Sequence
<220> FEATURE:
<223> OTHER INFORMATION: human PTH 1-67

<400> SEQUENCE: 18

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu
65

<210> SEQ ID NO 19
<211> LENGTH: 66
<212> TYPE: PRT
<213> ORGANISM: Artificial Sequence
<220> FEATURE:
<223> OTHER INFORMATION: human PTH 1-66

<400> SEQUENCE: 19

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser
65

<210> SEQ ID NO 20
<211> LENGTH: 65
<212> TYPE: PRT
<213> ORGANISM: Artificial Sequence
<220> FEATURE:
<223> OTHER INFORMATION: human PTH 1-65

<400> SEQUENCE: 20

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys
65

<210> SEQ ID NO 21
<211> LENGTH: 64
<212> TYPE: PRT
<213> ORGANISM: Artificial Sequence
<220> FEATURE:
<223> OTHER INFORMATION: human PTH 1-64

<400> SEQUENCE: 21

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

<210> SEQ ID NO 22
<211> LENGTH: 63
<212> TYPE: PRT
<213> ORGANISM: Artificial Sequence
<220> FEATURE:
<223> OTHER INFORMATION: human PTH 1-63

<400> SEQUENCE: 22

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His
    50                  55                  60

<210> SEQ ID NO 23
<211> LENGTH: 62
<212> TYPE: PRT
<213> ORGANISM: Artificial Sequence
<220> FEATURE:
<223> OTHER INFORMATION: human PTH 1-62

<400> SEQUENCE: 23

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser
        50                  55                  60
```

<210> SEQ ID NO 24
<211> LENGTH: 61
<212> TYPE: PRT
<213> ORGANISM: Artificial Sequence
<220> FEATURE:
<223> OTHER INFORMATION: human PTH 1-61

<400> SEQUENCE: 24

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu
        50                  55                  60
```

<210> SEQ ID NO 25
<211> LENGTH: 60
<212> TYPE: PRT
<213> ORGANISM: Artificial Sequence
<220> FEATURE:
<223> OTHER INFORMATION: human PTH 1-60

<400> SEQUENCE: 25

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val
        50                  55                  60
```

<210> SEQ ID NO 26
<211> LENGTH: 59
<212> TYPE: PRT
<213> ORGANISM: Artificial Sequence
<220> FEATURE:
<223> OTHER INFORMATION: human PTH 1-59

<400> SEQUENCE: 26

```
Ser Val Ser Glu Ile Gln Leu Met His Asn Leu Gly Lys His Leu Asn
```

-continued

```
                1               5                  10                  15
Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu
        50                  55

<210> SEQ ID NO 27
<211> LENGTH: 58
<212> TYPE: PRT
<213> ORGANISM: Artificial Sequence
<220> FEATURE:
<223> OTHER INFORMATION: human PTH 1-58

<400> SEQUENCE: 27

Ser Val Ser Glu Ile Gln Leu Met His Asn Leu Gly Lys His Leu Asn
1               5                  10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val
        50                  55

<210> SEQ ID NO 28
<211> LENGTH: 57
<212> TYPE: PRT
<213> ORGANISM: Artificial Sequence
<220> FEATURE:
<223> OTHER INFORMATION: human PTH 1-57

<400> SEQUENCE: 28

Ser Val Ser Glu Ile Gln Leu Met His Asn Leu Gly Lys His Leu Asn
1               5                  10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn
        50                  55

<210> SEQ ID NO 29
<211> LENGTH: 56
<212> TYPE: PRT
<213> ORGANISM: Artificial Sequence
<220> FEATURE:
<223> OTHER INFORMATION: human PTH 1-56

<400> SEQUENCE: 29

Ser Val Ser Glu Ile Gln Leu Met His Asn Leu Gly Lys His Leu Asn
1               5                  10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp
        50                  55

<210> SEQ ID NO 30
```

```
<211> LENGTH: 55
<212> TYPE: PRT
<213> ORGANISM: Artificial Sequence
<220> FEATURE:
<223> OTHER INFORMATION: human PTH 1-55

<400> SEQUENCE: 30

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu
    50                  55

<210> SEQ ID NO 31
<211> LENGTH: 54
<212> TYPE: PRT
<213> ORGANISM: Artificial Sequence
<220> FEATURE:
<223> OTHER INFORMATION: human PTH 1-54

<400> SEQUENCE: 31

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys
    50

<210> SEQ ID NO 32
<211> LENGTH: 53
<212> TYPE: PRT
<213> ORGANISM: Artificial Sequence
<220> FEATURE:
<223> OTHER INFORMATION: human PTH 1-53

<400> SEQUENCE: 32

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys
    50

<210> SEQ ID NO 33
<211> LENGTH: 52
<212> TYPE: PRT
<213> ORGANISM: Artificial Sequence
<220> FEATURE:
<223> OTHER INFORMATION: human PTH 1-52

<400> SEQUENCE: 33

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30
```

Asn Phe Val Ala Leu Gly Ala Pro Leu Ala Pro Arg Asp Ala Gly Ser
        35                  40                  45

Gln Arg Pro Arg
    50

<210> SEQ ID NO 34
<211> LENGTH: 51
<212> TYPE: PRT
<213> ORGANISM: Artificial Sequence
<220> FEATURE:
<223> OTHER INFORMATION: human PTH 1-51

<400> SEQUENCE: 34

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro
    50

<210> SEQ ID NO 35
<211> LENGTH: 50
<212> TYPE: PRT
<213> ORGANISM: Artificial Sequence
<220> FEATURE:
<223> OTHER INFORMATION: human PTH 1-50

<400> SEQUENCE: 35

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg
    50

<210> SEQ ID NO 36
<211> LENGTH: 49
<212> TYPE: PRT
<213> ORGANISM: Artificial Sequence
<220> FEATURE:
<223> OTHER INFORMATION: human PTH 1-49

<400> SEQUENCE: 36

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln

<210> SEQ ID NO 37
<211> LENGTH: 48
<212> TYPE: PRT
<213> ORGANISM: Artificial Sequence
<220> FEATURE:
<223> OTHER INFORMATION: human PTH 1-48

<400> SEQUENCE: 37

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

<210> SEQ ID NO 38
<211> LENGTH: 47
<212> TYPE: PRT
<213> ORGANISM: Artificial Sequence
<220> FEATURE:
<223> OTHER INFORMATION: human PTH 1-47

<400> SEQUENCE: 38

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly
            35                  40                  45

<210> SEQ ID NO 39
<211> LENGTH: 46
<212> TYPE: PRT
<213> ORGANISM: Artificial Sequence
<220> FEATURE:
<223> OTHER INFORMATION: human PTH 1-46

<400> SEQUENCE: 39

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala
            35                  40                  45

<210> SEQ ID NO 40
<211> LENGTH: 45
<212> TYPE: PRT
<213> ORGANISM: Artificial Sequence
<220> FEATURE:
<223> OTHER INFORMATION: human PTH 1-45

<400> SEQUENCE: 40

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp
            35                  40                  45

<210> SEQ ID NO 41
<211> LENGTH: 44
<212> TYPE: PRT
<213> ORGANISM: Artificial Sequence
<220> FEATURE:
<223> OTHER INFORMATION: human PTH 1-44

<400> SEQUENCE: 41

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg
        35                  40
```

<210> SEQ ID NO 42
<211> LENGTH: 43
<212> TYPE: PRT
<213> ORGANISM: Artificial Sequence
<220> FEATURE:
<223> OTHER INFORMATION: human PTH 1-43

<400> SEQUENCE: 42

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro
        35                  40
```

<210> SEQ ID NO 43
<211> LENGTH: 42
<212> TYPE: PRT
<213> ORGANISM: Artificial Sequence
<220> FEATURE:
<223> OTHER INFORMATION: human PTH 1-42

<400> SEQUENCE: 43

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala
        35                  40
```

<210> SEQ ID NO 44
<211> LENGTH: 41
<212> TYPE: PRT
<213> ORGANISM: Artificial Sequence
<220> FEATURE:
<223> OTHER INFORMATION: human PTH-41

<400> SEQUENCE: 44

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu
        35                  40
```

<210> SEQ ID NO 45
<211> LENGTH: 40
<212> TYPE: PRT
<213> ORGANISM: Artificial Sequence
<220> FEATURE:
<223> OTHER INFORMATION: human PTH 1-40

<400> SEQUENCE: 45

```
Ser Val Ser Glu Ile Gln Leu Met His Asn Leu Gly Lys His Leu Asn
1               5                   10                  15
```

```
Ser Met Glu Arg Val Glu Trp Leu Arg Lys Lys Leu Gln Asp Val His
            20                  25                  30

Asn Phe Val Ala Leu Gly Ala Pro
            35                  40

<210> SEQ ID NO 46
<211> LENGTH: 39
<212> TYPE: PRT
<213> ORGANISM: Artificial Sequence
<220> FEATURE:
<223> OTHER INFORMATION: human PTH 1-39

<400> SEQUENCE: 46

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala
            35

<210> SEQ ID NO 47
<211> LENGTH: 38
<212> TYPE: PRT
<213> ORGANISM: Artificial Sequence
<220> FEATURE:
<223> OTHER INFORMATION: human PTH 1-38

<400> SEQUENCE: 47

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly
            35

<210> SEQ ID NO 48
<211> LENGTH: 37
<212> TYPE: PRT
<213> ORGANISM: Artificial Sequence
<220> FEATURE:
<223> OTHER INFORMATION: human PTH 1-37

<400> SEQUENCE: 48

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu
            35

<210> SEQ ID NO 49
<211> LENGTH: 36
<212> TYPE: PRT
<213> ORGANISM: Artificial Sequence
<220> FEATURE:
<223> OTHER INFORMATION: human PTH 1-36

<400> SEQUENCE: 49

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30
```

Asn Phe Val Ala
        35

<210> SEQ ID NO 50
<211> LENGTH: 35
<212> TYPE: PRT
<213> ORGANISM: Artificial Sequence
<220> FEATURE:
<223> OTHER INFORMATION: human PTH 1-35

<400> SEQUENCE: 50

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val
        35

<210> SEQ ID NO 51
<211> LENGTH: 34
<212> TYPE: PRT
<213> ORGANISM: Artificial Sequence
<220> FEATURE:
<223> OTHER INFORMATION: human PTH 1-34

<400> SEQUENCE: 51

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 52
<211> LENGTH: 33
<212> TYPE: PRT
<213> ORGANISM: Artificial Sequence
<220> FEATURE:
<223> OTHER INFORMATION: human PTH 1-33

<400> SEQUENCE: 52

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn

<210> SEQ ID NO 53
<211> LENGTH: 32
<212> TYPE: PRT
<213> ORGANISM: Artificial Sequence
<220> FEATURE:
<223> OTHER INFORMATION: human PTH 1-32

<400> SEQUENCE: 53

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

<210> SEQ ID NO 54
<211> LENGTH: 31
<212> TYPE: PRT
<213> ORGANISM: Artificial Sequence
<220> FEATURE:
<223> OTHER INFORMATION: human PTH 1-31

<400> SEQUENCE: 54

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: human PTH 1-30

<400> SEQUENCE: 55

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp
            20                  25                  30

<210> SEQ ID NO 56
<211> LENGTH: 29
<212> TYPE: PRT
<213> ORGANISM: Artificial Sequence
<220> FEATURE:
<223> OTHER INFORMATION: human PTH 1-29

<400> SEQUENCE: 56

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln
            20                  25

<210> SEQ ID NO 57
<211> LENGTH: 28
<212> TYPE: PRT
<213> ORGANISM: Artificial Sequence
<220> FEATURE:
<223> OTHER INFORMATION: human PTH 1-28

<400> SEQUENCE: 57

Ser Val Ser Glu Ile Gln Leu Met His Asn Leu Gly Lys His Leu Asn
1               5                   10                  15

Ser Met Glu Arg Val Glu Trp Leu Arg Lys Lys Leu
            20                  25

<210> SEQ ID NO 58
<211> LENGTH: 27
<212> TYPE: PRT
<213> ORGANISM: Artificial Sequence
<220> FEATURE:
<223> OTHER INFORMATION: human PTH 1-27

<400> SEQUENCE: 58

Ser Val Ser Glu Ile Gln Leu Met His Asn Leu Gly Lys His Leu Asn
1               5                   10                  15

Ser Met Glu Arg Val Glu Trp Leu Arg Lys Lys
            20                  25

<210> SEQ ID NO 59
<211> LENGTH: 26
<212> TYPE: PRT

```
<213> ORGANISM: Artificial Sequence
<220> FEATURE:
<223> OTHER INFORMATION: human PTH 1-26

<400> SEQUENCE: 59

Ser Val Ser Glu Ile Gln Leu Met His Asn Leu Gly Lys His Leu Asn
1               5                   10                  15

Ser Met Glu Arg Val Glu Trp Leu Arg Lys
            20                  25

<210> SEQ ID NO 60
<211> LENGTH: 25
<212> TYPE: PRT
<213> ORGANISM: Artificial Sequence
<220> FEATURE:
<223> OTHER INFORMATION: human PTH 1-25

<400> SEQUENCE: 60

Ser Val Ser Glu Ile Gln Leu Met His Asn Leu Gly Lys His Leu Asn
1               5                   10                  15

Ser Met Glu Arg Val Glu Trp Leu Arg
            20                  25

<210> SEQ ID NO 61
<211> LENGTH: 84
<212> TYPE: PRT
<213> ORGANISM: Artificial Sequence
<220> FEATURE:
<223> OTHER INFORMATION: amidated human PTH 1-84
<220> FEATURE:
<221> NAME/KEY: MOD_RES
<222> LOCATION: (84)..(84)
<223> OTHER INFORMATION: AMIDATION

<400> SEQUENCE: 61

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 62
<211> LENGTH: 83
<212> TYPE: PRT
<213> ORGANISM: Artificial Sequence
<220> FEATURE:
<223> OTHER INFORMATION: amidated human PTH 1-83
<220> FEATURE:
<221> NAME/KEY: MOD_RES
<222> LOCATION: (83)..(83)
<223> OTHER INFORMATION: AMIDATION

<400> SEQUENCE: 62

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30
```

```
Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
     50                  55                  60

Lys Ser Leu Gly Glu Ala Asp Lys Ala Asp Val Asn Val Leu Thr Lys
 65                  70                  75                  80

Ala Lys Ser

<210> SEQ ID NO 63
<211> LENGTH: 82
<212> TYPE: PRT
<213> ORGANISM: Artificial Sequence
<220> FEATURE:
<223> OTHER INFORMATION: amidated human PTH 1-82
<220> FEATURE:
<221> NAME/KEY: MOD_RES
<222> LOCATION: (82)..(82)
<223> OTHER INFORMATION: AMIDATION

<400> SEQUENCE: 63

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
             20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
     50                  55                  60

Lys Ser Leu Gly Glu Ala Asp Lys Ala Asp Val Asn Val Leu Thr Lys
 65                  70                  75                  80

Ala Lys

<210> SEQ ID NO 64
<211> LENGTH: 81
<212> TYPE: PRT
<213> ORGANISM: Artificial Sequence
<220> FEATURE:
<223> OTHER INFORMATION: amidated human PTH 1-81
<220> FEATURE:
<221> NAME/KEY: MOD_RES
<222> LOCATION: (81)..(81)
<223> OTHER INFORMATION: AMIDATION

<400> SEQUENCE: 64

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
             20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
     50                  55                  60

Lys Ser Leu Gly Glu Ala Asp Lys Ala Asp Val Asn Val Leu Thr Lys
 65                  70                  75                  80

Ala

<210> SEQ ID NO 65
<211> LENGTH: 80
<212> TYPE: PRT
<213> ORGANISM: Artificial Sequence
<220> FEATURE:
```

<223> OTHER INFORMATION: amidated human PTH 1-80
<220> FEATURE:
<221> NAME/KEY: MOD_RES
<222> LOCATION: (80)..(80)
<223> OTHER INFORMATION: AMIDATION

<400> SEQUENCE: 65

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

<210> SEQ ID NO 66
<211> LENGTH: 79
<212> TYPE: PRT
<213> ORGANISM: Artificial Sequence
<220> FEATURE:
<223> OTHER INFORMATION: amidated human PTH 1-79
<220> FEATURE:
<221> NAME/KEY: MOD_RES
<222> LOCATION: (79)..(79)
<223> OTHER INFORMATION: AMIDATION

<400> SEQUENCE: 66

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr
65                  70                  75

<210> SEQ ID NO 67
<211> LENGTH: 78
<212> TYPE: PRT
<213> ORGANISM: Artificial Sequence
<220> FEATURE:
<223> OTHER INFORMATION: amidated human PTH 1-78
<220> FEATURE:
<221> NAME/KEY: MOD_RES
<222> LOCATION: (78)..(78)
<223> OTHER INFORMATION: AMIDATION

<400> SEQUENCE: 67

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu

<210> SEQ ID NO 68
<211> LENGTH: 77
<212> TYPE: PRT
<213> ORGANISM: Artificial Sequence
<220> FEATURE:
<223> OTHER INFORMATION: amidated human PTH 1-77
<220> FEATURE:
<221> NAME/KEY: MOD_RES
<222> LOCATION: (77)..(77)
<223> OTHER INFORMATION: AMIDATION

<400> SEQUENCE: 68

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val
65                  70                  75

<210> SEQ ID NO 69
<211> LENGTH: 76
<212> TYPE: PRT
<213> ORGANISM: Artificial Sequence
<220> FEATURE:
<223> OTHER INFORMATION: amidated human PTH 1-76
<220> FEATURE:
<221> NAME/KEY: MOD_RES
<222> LOCATION: (76)..(76)
<223> OTHER INFORMATION: AMIDATION

<400> SEQUENCE: 69

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn
65                  70                  75

<210> SEQ ID NO 70
<211> LENGTH: 75
<212> TYPE: PRT
<213> ORGANISM: Artificial Sequence
<220> FEATURE:
<223> OTHER INFORMATION: amidated human PTH 1-75
<220> FEATURE:
<221> NAME/KEY: MOD_RES
<222> LOCATION: (75)..(75)
<223> OTHER INFORMATION: AMIDATION

<400> SEQUENCE: 70

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

```
Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val
65                  70                  75
```

<210> SEQ ID NO 71
<211> LENGTH: 74
<212> TYPE: PRT
<213> ORGANISM: Artificial Sequence
<220> FEATURE:
<223> OTHER INFORMATION: amidated human PTH 1-74
<220> FEATURE:
<221> NAME/KEY: MOD_RES
<222> LOCATION: (74)..(74)
<223> OTHER INFORMATION: AMIDATION

<400> SEQUENCE: 71

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp
65                  70
```

<210> SEQ ID NO 72
<211> LENGTH: 73
<212> TYPE: PRT
<213> ORGANISM: Artificial Sequence
<220> FEATURE:
<223> OTHER INFORMATION: amidated human PTH 1-73
<220> FEATURE:
<221> NAME/KEY: MOD_RES
<222> LOCATION: (73)..(73)
<223> OTHER INFORMATION: AMIDATION

<400> SEQUENCE: 72

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala
65                  70
```

<210> SEQ ID NO 73
<211> LENGTH: 72
<212> TYPE: PRT
<213> ORGANISM: Artificial Sequence
<220> FEATURE:
<223> OTHER INFORMATION: amidated human PTH 1-72
<220> FEATURE:
<221> NAME/KEY: MOD_RES
<222> LOCATION: (72)..(72)
<223> OTHER INFORMATION: AMIDATION

<400> SEQUENCE: 73

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys
65                  70

<210> SEQ ID NO 74
<211> LENGTH: 71
<212> TYPE: PRT
<213> ORGANISM: Artificial Sequence
<220> FEATURE:
<223> OTHER INFORMATION: amidated human PTH 1-71
<220> FEATURE:
<221> NAME/KEY: MOD_RES
<222> LOCATION: (71)..(71)
<223> OTHER INFORMATION: AMIDATION

<400> SEQUENCE: 74

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp
65                  70

<210> SEQ ID NO 75
<211> LENGTH: 70
<212> TYPE: PRT
<213> ORGANISM: Artificial Sequence
<220> FEATURE:
<223> OTHER INFORMATION: amidated human PTH 1-70
<220> FEATURE:
<221> NAME/KEY: MOD_RES
<222> LOCATION: (70)..(70)
<223> OTHER INFORMATION: AMIDATION

<400> SEQUENCE: 75

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala
65                  70

<210> SEQ ID NO 76
<211> LENGTH: 69

```
<212> TYPE: PRT
<213> ORGANISM: Artificial Sequence
<220> FEATURE:
<223> OTHER INFORMATION: amidated human PTH 1-69
<220> FEATURE:
<221> NAME/KEY: MOD_RES
<222> LOCATION: (69)..(69)
<223> OTHER INFORMATION: AMIDATION

<400> SEQUENCE: 76

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu
65

<210> SEQ ID NO 77
<211> LENGTH: 68
<212> TYPE: PRT
<213> ORGANISM: Artificial Sequence
<220> FEATURE:
<223> OTHER INFORMATION: amidated human PTH 1-68
<220> FEATURE:
<221> NAME/KEY: MOD_RES
<222> LOCATION: (68)..(68)
<223> OTHER INFORMATION: AMIDATION

<400> SEQUENCE: 77

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly
65

<210> SEQ ID NO 78
<211> LENGTH: 67
<212> TYPE: PRT
<213> ORGANISM: Artificial Sequence
<220> FEATURE:
<223> OTHER INFORMATION: amidated human PTH 1-67
<220> FEATURE:
<221> NAME/KEY: MOD_RES
<222> LOCATION: (67)..(67)
<223> OTHER INFORMATION: AMIDATION

<400> SEQUENCE: 78

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
```

50                  55                  60

Lys Ser Leu
 65

<210> SEQ ID NO 79
<211> LENGTH: 66
<212> TYPE: PRT
<213> ORGANISM: Artificial Sequence
<220> FEATURE:
<223> OTHER INFORMATION: amidated human PTH 1-66
<220> FEATURE:
<221> NAME/KEY: MOD_RES
<222> LOCATION: (66)..(66)
<223> OTHER INFORMATION: AMIDATION

<400> SEQUENCE: 79

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser
 65

<210> SEQ ID NO 80
<211> LENGTH: 65
<212> TYPE: PRT
<213> ORGANISM: Artificial Sequence
<220> FEATURE:
<223> OTHER INFORMATION: amidated human PTH 1-65
<220> FEATURE:
<221> NAME/KEY: MOD_RES
<222> LOCATION: (65)..(65)
<223> OTHER INFORMATION: AMIDATION

<400> SEQUENCE: 80

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys
 65

<210> SEQ ID NO 81
<211> LENGTH: 64
<212> TYPE: PRT
<213> ORGANISM: Artificial Sequence
<220> FEATURE:
<223> OTHER INFORMATION: amidated human PTH 1-64
<220> FEATURE:
<221> NAME/KEY: MOD_RES
<222> LOCATION: (64)..(64)
<223> OTHER INFORMATION: AMIDATION

<400> SEQUENCE: 81

Ser Val Ser Glu Ile Gln Leu Met His Asn Leu Gly Lys His Leu Asn
 1               5                  10                  15

-continued

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

<210> SEQ ID NO 82
<211> LENGTH: 63
<212> TYPE: PRT
<213> ORGANISM: Artificial Sequence
<220> FEATURE:
<223> OTHER INFORMATION: amidated human PTH 1-63
<220> FEATURE:
<221> NAME/KEY: MOD_RES
<222> LOCATION: (63)..(63)
<223> OTHER INFORMATION: AMIDATION

<400> SEQUENCE: 82

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His
    50                  55                  60

<210> SEQ ID NO 83
<211> LENGTH: 62
<212> TYPE: PRT
<213> ORGANISM: Artificial Sequence
<220> FEATURE:
<223> OTHER INFORMATION: amidated human PTH 1-62
<220> FEATURE:
<221> NAME/KEY: MOD_RES
<222> LOCATION: (62)..(62)
<223> OTHER INFORMATION: AMIDATION

<400> SEQUENCE: 83

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser
    50                  55                  60

<210> SEQ ID NO 84
<211> LENGTH: 61
<212> TYPE: PRT
<213> ORGANISM: Artificial Sequence
<220> FEATURE:
<223> OTHER INFORMATION: amidated human PTH 1-61
<220> FEATURE:
<221> NAME/KEY: MOD_RES
<222> LOCATION: (61)..(61)
<223> OTHER INFORMATION: AMIDATION

<400> SEQUENCE: 84

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu
    50                  55                  60

<210> SEQ ID NO 85
<211> LENGTH: 60
<212> TYPE: PRT
<213> ORGANISM: Artificial Sequence
<220> FEATURE:
<223> OTHER INFORMATION: amidated human PTH 1-60
<220> FEATURE:
<221> NAME/KEY: MOD_RES
<222> LOCATION: (60)..(60)
<223> OTHER INFORMATION: ACETYLATION

<400> SEQUENCE: 85

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val
    50                  55                  60

<210> SEQ ID NO 86
<211> LENGTH: 59
<212> TYPE: PRT
<213> ORGANISM: Artificial Sequence
<220> FEATURE:
<223> OTHER INFORMATION: amidated human PTH 1-59
<220> FEATURE:
<221> NAME/KEY: MOD_RES
<222> LOCATION: (59)..(59)
<223> OTHER INFORMATION: AMIDATION

<400> SEQUENCE: 86

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu
    50                  55

<210> SEQ ID NO 87
<211> LENGTH: 58
<212> TYPE: PRT
<213> ORGANISM: Artificial Sequence
<220> FEATURE:
<223> OTHER INFORMATION: amidated human PTH 1-58
<220> FEATURE:
<221> NAME/KEY: MOD_RES
<222> LOCATION: (58)..(58)
<223> OTHER INFORMATION: AMIDATION

<400> SEQUENCE: 87

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His

```
                    20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val
        50                  55

<210> SEQ ID NO 88
<211> LENGTH: 57
<212> TYPE: PRT
<213> ORGANISM: Artificial Sequence
<220> FEATURE:
<223> OTHER INFORMATION: amidated human PTH 1-57
<220> FEATURE:
<221> NAME/KEY: MOD_RES
<222> LOCATION: (57)..(57)
<223> OTHER INFORMATION: AMIDATION

<400> SEQUENCE: 88

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn
        50                  55

<210> SEQ ID NO 89
<211> LENGTH: 56
<212> TYPE: PRT
<213> ORGANISM: Artificial Sequence
<220> FEATURE:
<223> OTHER INFORMATION: amidated human PTH 1-56
<220> FEATURE:
<221> NAME/KEY: MOD_RES
<222> LOCATION: (56)..(56)
<223> OTHER INFORMATION: AMIDATION

<400> SEQUENCE: 89

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp
        50                  55

<210> SEQ ID NO 90
<211> LENGTH: 55
<212> TYPE: PRT
<213> ORGANISM: Artificial Sequence
<220> FEATURE:
<223> OTHER INFORMATION: amidated human PTH 1-55
<220> FEATURE:
<221> NAME/KEY: MOD_RES
<222> LOCATION: (55)..(55)
<223> OTHER INFORMATION: AMIDATION

<400> SEQUENCE: 90

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30
```

```
Asn Phe Val Ala Leu Gly Ala Pro Leu Ala Pro Arg Asp Ala Gly Ser
        35                  40                  45

Gln Arg Pro Arg Lys Lys Glu
    50                  55

<210> SEQ ID NO 91
<211> LENGTH: 54
<212> TYPE: PRT
<213> ORGANISM: Artificial Sequence
<220> FEATURE:
<223> OTHER INFORMATION: amidated human PTH 1-54
<220> FEATURE:
<221> NAME/KEY: MOD_RES
<222> LOCATION: (54)..(54)
<223> OTHER INFORMATION: AMIDATION

<400> SEQUENCE: 91

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys
    50

<210> SEQ ID NO 92
<211> LENGTH: 53
<212> TYPE: PRT
<213> ORGANISM: Artificial Sequence
<220> FEATURE:
<223> OTHER INFORMATION: amidated human PTH 1-53
<220> FEATURE:
<221> NAME/KEY: MOD_RES
<222> LOCATION: (53)..(53)
<223> OTHER INFORMATION: AMIDATION

<400> SEQUENCE: 92

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys
    50

<210> SEQ ID NO 93
<211> LENGTH: 52
<212> TYPE: PRT
<213> ORGANISM: Artificial Sequence
<220> FEATURE:
<223> OTHER INFORMATION: amidated human PTH 1-52
<220> FEATURE:
<221> NAME/KEY: MOD_RES
<222> LOCATION: (52)..(52)
<223> OTHER INFORMATION: AMIDATION

<400> SEQUENCE: 93

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30
```

```
Asn Phe Val Ala Leu Gly Ala Pro Leu Ala Pro Arg Asp Ala Gly Ser
            35                  40                  45

Gln Arg Pro Arg
    50

<210> SEQ ID NO 94
<211> LENGTH: 51
<212> TYPE: PRT
<213> ORGANISM: Artificial Sequence
<220> FEATURE:
<223> OTHER INFORMATION: amidated human PTH 1-51
<220> FEATURE:
<221> NAME/KEY: MOD_RES
<222> LOCATION: (51)..(51)
<223> OTHER INFORMATION: AMIDATION

<400> SEQUENCE: 94

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
            35                  40                  45

Gln Arg Pro
    50

<210> SEQ ID NO 95
<211> LENGTH: 50
<212> TYPE: PRT
<213> ORGANISM: Artificial Sequence
<220> FEATURE:
<223> OTHER INFORMATION: amidated human PTH 1-50
<220> FEATURE:
<221> NAME/KEY: MOD_RES
<222> LOCATION: (50)..(50)
<223> OTHER INFORMATION: AMIDATION

<400> SEQUENCE: 95

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
            35                  40                  45

Gln Arg
    50

<210> SEQ ID NO 96
<211> LENGTH: 49
<212> TYPE: PRT
<213> ORGANISM: Artificial Sequence
<220> FEATURE:
<223> OTHER INFORMATION: amidated human PTH 1-49
<220> FEATURE:
<221> NAME/KEY: MOD_RES
<222> LOCATION: (49)..(49)
<223> OTHER INFORMATION: AMIDATION

<400> SEQUENCE: 96

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
```

```
                       35                  40                  45

Gln

<210> SEQ ID NO 97
<211> LENGTH: 48
<212> TYPE: PRT
<213> ORGANISM: Artificial Sequence
<220> FEATURE:
<223> OTHER INFORMATION: amidated human PTH 1-48
<220> FEATURE:
<221> NAME/KEY: MOD_RES
<222> LOCATION: (48)..(48)
<223> OTHER INFORMATION: AMIDATION

<400> SEQUENCE: 97

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

<210> SEQ ID NO 98
<211> LENGTH: 47
<212> TYPE: PRT
<213> ORGANISM: Artificial Sequence
<220> FEATURE:
<223> OTHER INFORMATION: amidated human PTH 1-47
<220> FEATURE:
<221> NAME/KEY: MOD_RES
<222> LOCATION: (47)..(47)
<223> OTHER INFORMATION: AMIDATION

<400> SEQUENCE: 98

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly
            35                  40                  45

<210> SEQ ID NO 99
<211> LENGTH: 46
<212> TYPE: PRT
<213> ORGANISM: Artificial Sequence
<220> FEATURE:
<223> OTHER INFORMATION: amidated human PTH 1-46
<220> FEATURE:
<221> NAME/KEY: MOD_RES
<222> LOCATION: (46)..(46)
<223> OTHER INFORMATION: AMIDATION

<400> SEQUENCE: 99

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala
            35                  40                  45

<210> SEQ ID NO 100
<211> LENGTH: 45
<212> TYPE: PRT
<213> ORGANISM: Artificial Sequence
<220> FEATURE:
```

<223> OTHER INFORMATION: amidated human PTH 1-45
<220> FEATURE:
<221> NAME/KEY: MOD_RES
<222> LOCATION: (45)..(45)
<223> OTHER INFORMATION: AMIDATION

<400> SEQUENCE: 100

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp
        35                  40                  45

<210> SEQ ID NO 101
<211> LENGTH: 44
<212> TYPE: PRT
<213> ORGANISM: Artificial Sequence
<220> FEATURE:
<223> OTHER INFORMATION: amidated human PTH 1-44
<220> FEATURE:
<221> NAME/KEY: MOD_RES
<222> LOCATION: (44)..(44)
<223> OTHER INFORMATION: AMIDATION

<400> SEQUENCE: 101

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg
        35                  40

<210> SEQ ID NO 102
<211> LENGTH: 43
<212> TYPE: PRT
<213> ORGANISM: Artificial Sequence
<220> FEATURE:
<223> OTHER INFORMATION: amidated human PTH 1-43
<220> FEATURE:
<221> NAME/KEY: MOD_RES
<222> LOCATION: (43)..(43)
<223> OTHER INFORMATION: AMIDATION

<400> SEQUENCE: 102

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro
        35                  40

<210> SEQ ID NO 103
<211> LENGTH: 42
<212> TYPE: PRT
<213> ORGANISM: Artificial Sequence
<220> FEATURE:
<223> OTHER INFORMATION: amidated human PTH 1-42
<220> FEATURE:
<221> NAME/KEY: MOD_RES
<222> LOCATION: (42)..(42)
<223> OTHER INFORMATION: AMIDATION

<400> SEQUENCE: 103

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala
        35                  40

<210> SEQ ID NO 104
<211> LENGTH: 41
<212> TYPE: PRT
<213> ORGANISM: Artificial Sequence
<220> FEATURE:
<223> OTHER INFORMATION: amidated human PTH 1-41
<220> FEATURE:
<221> NAME/KEY: MOD_RES
<222> LOCATION: (41)..(41)
<223> OTHER INFORMATION: AMIDATION

<400> SEQUENCE: 104

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu
        35                  40

<210> SEQ ID NO 105
<211> LENGTH: 40
<212> TYPE: PRT
<213> ORGANISM: Artificial Sequence
<220> FEATURE:
<223> OTHER INFORMATION: amidated human PTH 1-40
<220> FEATURE:
<221> NAME/KEY: MOD_RES
<222> LOCATION: (40)..(40)
<223> OTHER INFORMATION: AMIDATION

<400> SEQUENCE: 105

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro
        35                  40

<210> SEQ ID NO 106
<211> LENGTH: 39
<212> TYPE: PRT
<213> ORGANISM: Artificial Sequence
<220> FEATURE:
<223> OTHER INFORMATION: amidated human PTH 1-39
<220> FEATURE:
<221> NAME/KEY: MOD_RES
<222> LOCATION: (39)..(39)
<223> OTHER INFORMATION: AMIDATION

<400> SEQUENCE: 106

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala
        35

<210> SEQ ID NO 107
<211> LENGTH: 38

```
<212> TYPE: PRT
<213> ORGANISM: Artificial Sequence
<220> FEATURE:
<223> OTHER INFORMATION: amidated human PTH 1-38
<220> FEATURE:
<221> NAME/KEY: MOD_RES
<222> LOCATION: (38)..(38)
<223> OTHER INFORMATION: AMIDATION

<400> SEQUENCE: 107

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly
            35

<210> SEQ ID NO 108
<211> LENGTH: 37
<212> TYPE: PRT
<213> ORGANISM: Artificial Sequence
<220> FEATURE:
<223> OTHER INFORMATION: amidated human PTH 1-37
<220> FEATURE:
<221> NAME/KEY: MOD_RES
<222> LOCATION: (37)..(37)
<223> OTHER INFORMATION: AMIDATION

<400> SEQUENCE: 108

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu
            35

<210> SEQ ID NO 109
<211> LENGTH: 36
<212> TYPE: PRT
<213> ORGANISM: Artificial Sequence
<220> FEATURE:
<223> OTHER INFORMATION: amidated human PTH 1-36
<220> FEATURE:
<221> NAME/KEY: MOD_RES
<222> LOCATION: (36)..(36)
<223> OTHER INFORMATION: AMIDATION

<400> SEQUENCE: 109

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala
            35

<210> SEQ ID NO 110
<211> LENGTH: 35
<212> TYPE: PRT
<213> ORGANISM: Artificial Sequence
<220> FEATURE:
<223> OTHER INFORMATION: amidated human PTH 1-35
<220> FEATURE:
<221> NAME/KEY: MOD_RES
<222> LOCATION: (35)..(35)
<223> OTHER INFORMATION: AMIDATION

<400> SEQUENCE: 110
```

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val
        35

<210> SEQ ID NO 111
<211> LENGTH: 34
<212> TYPE: PRT
<213> ORGANISM: Artificial Sequence
<220> FEATURE:
<223> OTHER INFORMATION: amidated human PTH 1-34
<220> FEATURE:
<221> NAME/KEY: MOD_RES
<222> LOCATION: (34)..(34)
<223> OTHER INFORMATION: AMIDATION

<400> SEQUENCE: 111

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 112
<211> LENGTH: 33
<212> TYPE: PRT
<213> ORGANISM: Artificial Sequence
<220> FEATURE:
<223> OTHER INFORMATION: amidated human PTH 1-33
<220> FEATURE:
<221> NAME/KEY: MOD_RES
<222> LOCATION: (33)..(33)
<223> OTHER INFORMATION: AMIDATION

<400> SEQUENCE: 112

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn

<210> SEQ ID NO 113
<211> LENGTH: 32
<212> TYPE: PRT
<213> ORGANISM: Artificial Sequence
<220> FEATURE:
<223> OTHER INFORMATION: amidated human PTH 1-32
<220> FEATURE:
<221> NAME/KEY: MOD_RES
<222> LOCATION: (32)..(32)
<223> OTHER INFORMATION: AMIDATION

<400> SEQUENCE: 113

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

<210> SEQ ID NO 114
<211> LENGTH: 31
<212> TYPE: PRT
<213> ORGANISM: Artificial Sequence

```
<220> FEATURE:
<223> OTHER INFORMATION: amidated human PTH 1-31
<220> FEATURE:
<221> NAME/KEY: MOD_RES
<222> LOCATION: (31)..(31)
<223> OTHER INFORMATION: AMIDATION

<400> SEQUENCE: 114

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
            20                  25                  30

<210> SEQ ID NO 115
<211> LENGTH: 30
<212> TYPE: PRT
<213> ORGANISM: Artificial Sequence
<220> FEATURE:
<223> OTHER INFORMATION: amidated human PTH 1-30
<220> FEATURE:
<221> NAME/KEY: MOD_RES
<222> LOCATION: (30)..(30)
<223> OTHER INFORMATION: AMIDATION

<400> SEQUENCE: 115

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp
            20                  25                  30

<210> SEQ ID NO 116
<211> LENGTH: 29
<212> TYPE: PRT
<213> ORGANISM: Artificial Sequence
<220> FEATURE:
<223> OTHER INFORMATION: amidated human PTH 1-29
<220> FEATURE:
<221> NAME/KEY: MOD_RES
<222> LOCATION: (29)..(29)
<223> OTHER INFORMATION: AMIDATION

<400> SEQUENCE: 116

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln
            20                  25

<210> SEQ ID NO 117
<211> LENGTH: 28
<212> TYPE: PRT
<213> ORGANISM: Artificial Sequence
<220> FEATURE:
<223> OTHER INFORMATION: amidated human PTH 1-28
<220> FEATURE:
<221> NAME/KEY: MOD_RES
<222> LOCATION: (28)..(28)
<223> OTHER INFORMATION: AMIDATION

<400> SEQUENCE: 117

Ser Val Ser Glu Ile Gln Leu Met His Asn Leu Gly Lys His Leu Asn
1               5                   10                  15

Ser Met Glu Arg Val Glu Trp Leu Arg Lys Lys Leu
            20                  25

<210> SEQ ID NO 118
<211> LENGTH: 27
<212> TYPE: PRT
```

```
<213> ORGANISM: Artificial Sequence
<220> FEATURE:
<223> OTHER INFORMATION: amidated human PTH 1-27
<220> FEATURE:
<221> NAME/KEY: MOD_RES
<222> LOCATION: (27)..(27)
<223> OTHER INFORMATION: AMIDATION

<400> SEQUENCE: 118

Ser Val Ser Glu Ile Gln Leu Met His Asn Leu Gly Lys His Leu Asn
1               5                   10                  15

Ser Met Glu Arg Val Glu Trp Leu Arg Lys Lys
            20                  25

<210> SEQ ID NO 119
<211> LENGTH: 26
<212> TYPE: PRT
<213> ORGANISM: Artificial Sequence
<220> FEATURE:
<223> OTHER INFORMATION: amidated human PTH 1-26
<220> FEATURE:
<221> NAME/KEY: MOD_RES
<222> LOCATION: (26)..(26)
<223> OTHER INFORMATION: AMIDATION

<400> SEQUENCE: 119

Ser Val Ser Glu Ile Gln Leu Met His Asn Leu Gly Lys His Leu Asn
1               5                   10                  15

Ser Met Glu Arg Val Glu Trp Leu Arg Lys
            20                  25

<210> SEQ ID NO 120
<211> LENGTH: 25
<212> TYPE: PRT
<213> ORGANISM: Artificial Sequence
<220> FEATURE:
<223> OTHER INFORMATION: amidated human PTH 1-25
<220> FEATURE:
<221> NAME/KEY: MOD_RES
<222> LOCATION: (25)..(25)
<223> OTHER INFORMATION: AMIDATION

<400> SEQUENCE: 120

Ser Val Ser Glu Ile Gln Leu Met His Asn Leu Gly Lys His Leu Asn
1               5                   10                  15

Ser Met Glu Arg Val Glu Trp Leu Arg
            20                  25

<210> SEQ ID NO 121
<211> LENGTH: 141
<212> TYPE: PRT
<213> ORGANISM: Homo sapiens

<400> SEQUENCE: 121

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile Arg Ala Thr Ser Glu Val Ser Pro Asn Ser Lys Pro
        35                  40                  45

Ser Pro Asn Thr Lys Asn His Pro Val Arg Phe Gly Ser Asp Asp Glu
    50                  55                  60

Gly Arg Tyr Leu Thr Gln Glu Thr Asn Lys Val Glu Thr Tyr Lys Glu
65                  70                  75                  80
```

```
Gln Pro Leu Lys Thr Pro Gly Lys Lys Lys Lys Gly Lys Pro Gly Lys
                85              90                  95

Arg Lys Glu Gln Glu Lys Lys Lys Arg Arg Thr Arg Ser Ala Trp Leu
            100             105                 110

Asp Ser Gly Val Thr Gly Ser Gly Leu Glu Gly Asp His Leu Ser Asp
        115             120                 125

Thr Ser Thr Thr Ser Leu Glu Leu Asp Ser Arg Arg His
    130             135             140

<210> SEQ ID NO 122
<211> LENGTH: 20
<212> TYPE: PRT
<213> ORGANISM: Artificial Sequence
<220> FEATURE:
<223> OTHER INFORMATION: Artificial random coil

<400> SEQUENCE: 122

Gly Gly Pro Gly Gly Pro Gly Pro Gly Gly Pro Gly Gly Pro Gly Pro
1               5                   10                  15

Gly Gly Pro Gly
            20
```